(12) United States Patent
Yang et al.

(10) Patent No.: US 11,136,320 B2
(45) Date of Patent: Oct. 5, 2021

(54) FUSED RING DERIVATIVE USED AS FGFR4 INHIBITOR

(71) Applicant: JACOBIO PHARMACEUTICALS CO., LTD., Beijing (CN)

(72) Inventors: Hongwei Yang, Beijing (CN); Rui Zhou, Beijing (CN); Liang Zhou, Beijing (CN); Xin Sun, Beijing (CN)

(73) Assignee: JACOBIO PHARMACEUTICALS CO., LTD., Beijing (CN)

( * ) Notice: Subject to any disclaimer, the term of this patent is extended or adjusted under 35 U.S.C. 154(b) by 0 days.

(21) Appl. No.: 17/315,481

(22) Filed: May 10, 2021

(65) Prior Publication Data

US 2021/0269442 A1   Sep. 2, 2021

Related U.S. Application Data

(63) Continuation of application No. 17/263,571, filed as application No. PCT/CN2019/098076 on Jul. 29, 2019.

(51) Int. Cl.
*C07D 471/04* (2006.01)
*C07D 519/00* (2006.01)
*A61P 35/00* (2006.01)

(52) U.S. Cl.
CPC ........... *C07D 471/04* (2013.01); *A61P 35/00* (2018.01); *C07D 519/00* (2013.01)

(58) Field of Classification Search
CPC ...... C07D 471/04; C07D 519/00; A61P 35/00
USPC .................................................. 514/211.03
See application file for complete search history.

(56) References Cited

U.S. PATENT DOCUMENTS 9,533,988 B2 *  1/2017  Buschmann ............ A61P 35/00

FOREIGN PATENT DOCUMENTS

| CN | 105683188 | 6/2016 |
|----|-----------|--------|
| CN | 107304210 | 10/2017 |
| CN | 107304211 | 10/2017 |
| CN | 108341815 | 7/2018 |
| WO | 2017198149 | 11/2017 |
| WO | 2017198221 | 11/2017 |
| WO | 2017202390 | 11/2017 |
| WO | 2018028664 | 2/2018 |

\* cited by examiner

*Primary Examiner* — Niloofar Rahmani
(74) *Attorney, Agent, or Firm* — Robin L. Teskin; Baker, Donelson, Bearman Caldwell & Berkowitz, PC

(57) ABSTRACT

A compound represented by formula I or a pharmaceutically acceptable salt thereof and a use thereof in preparing a drug for treating, stopping or preventing a disease or disorder mediated by FGFR4 activity.

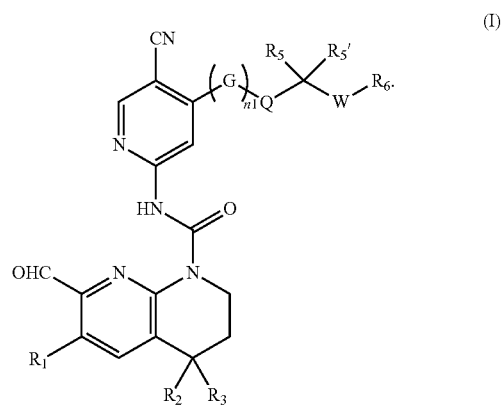

2 Claims, No Drawings

FUSED RING DERIVATIVE USED AS FGFR4 INHIBITOR

CROSS-REFERENCE TO RELATED APPLICATIONS

This application is a continuation of U.S. application Ser. No. 17/263,571, filed Jan. 27, 2021, which is a U.S. Nat'l Phase of Int'l Appl. No. PCT/CN2019/098076, filed Jul. 29, 2019, which claims priority to Int'l Appl. No. PCT/CN2018/097450, filed Jul. 27, 2018, each of which are incorporated herein by reference in their entireties.

TECHNICAL FIELD

The present invention provides fused ring derivative compound, uses for inhibiting FGFR4 and methods of treating diseases using said compound thereof.

BACKGROUND ART

Fibroblast Growth Factor Receptor (FGFR) belongs to the family of receptor protein tyrosine kinases. Many signaling pathways, including Ras-MAPK, AKT-PI3K, and phospholipase C, can be activated through the binding of FGFR and its corresponding ligands, and these pathways play an important role in cell growth, proliferation and survival.

Alterations in FGFRs are associated with many human cancers, and these alterations, including overexpression of FGF ligand, FGFR or activated FGFR mutations, can lead to tumor occurrence, development and resistance to traditional cancer treatments by activating the pathway. Large-scale DNA sequencing of thousands of tumor samples revealed that components of the FGFR pathway are the most common mutations in human cancers. FGFR4 is a tyrosine kinase receptor in the human body encoded by the gene FGFR4 and is highly conserved in evolution, and it works by combining with its specific ligand FGF19. The signaling pathway of FGFR is roughly shown as follows: activated FGFR4 causes phosphorylation of FRS2 and recruits GRB2, thus the signaling pathways of Ras-Raf-ERK1/2MAPK and PI3K-Akt are finally activated, which makes the cells proliferate and resist apoptosis. More and more researches have indicated that FGFR activation and the overexpression of FGF19 play an important role in the occurrence and development of liver cancer, and the inhibition of FGFR4 can effectively reduce the occurrence of liver cancer. FGFR4, ligand FGF19 and coreceptor KLB were highly expressed in about ⅓ of liver cancer patients. In addition, the changes of FGFR4-FGF19 signal axis are also related to the occurrence of colorectal cancer, breast cancer, pancreatic cancer, prostate cancer, lung cancer, and thyroid cancer.

According to preliminary studies, fibroblast growth factor receptor 4 (FGFR4) inhibitors have great potential for the treatment of liver cancer, and have better pertinence and effectiveness than the similar drugs. Liver cancer, the second only to lung cancer, is the most common malignant tumor and fatal disease, and china has the most liver cancer patients in the world. Sorafenib, as the only approved first-line drug for the treatment of patients with advanced liver cancer, only extends average three months survival time of the patient, and it has strong side effects because it is a multi-targeted tyrosine kinase inhibitor. Therefore, the development of more effective liver cancer drugs has become an urgent need in the world, and FGFR4 inhibitors provide a possibility for breakthroughs in this area.

At present, the inhibitor of FGFR4 is a hot research direction in the field of worldwide liver cancer therapeutic research, and the world biopharmaceutical companies are competing for a market direction of FGFR4 inhibitors. However, no one drug of FGFR4 inhibitor has been marketed currently due to the limitation of experimental methods and the period of the research and so on. China has the highest incidence of liver cancer and the most patients with liver cancer in the world, thus the breakthrough in this direction of FGFR inhibitors will have strong significance to clinical application. At present, no similar drugs of FGFR inhibitors are in clinical studies in China, and the worldwide FGFR inhibitors are all in the early clinical research stage. Therefore, the breakthrough in this direction of FGFR inhibitors will greatly enhance the international competitiveness of the new drug research and development of China.

SUMMARY OF INVENTION

The present invention relates to fused ring compound, which as an FGFR4 inhibitors use for treating diseases mediated by FGFR4. The invention first provides the compound shown in structural formula I or a pharmaceutically acceptable salt thereof:

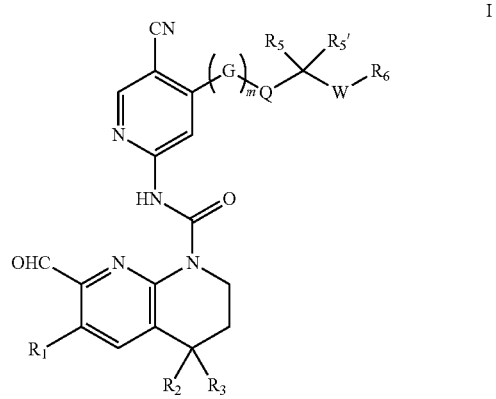

Wherein:
$R_1$ at each occurrence is independently

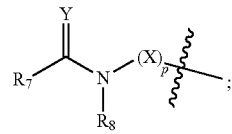

X at each occurrence is independently selected from absent, O, —$NR_{X1}$— or —$CR_{X1}R_{X2}$—; and p is 0, 1, 2 or 3;
$R_{X1}$ and $R_{X2}$ at each occurrence are independently selected from H; D; —F; —Cl; —Br; —I; —$C_{1-6}$alkyl; —$C_{1-6}$alkyl substituted with 1, 2, or 3 substituents; —$C_{1-6}$alkoxy or —$C_{1-6}$alkoxy substituted with 1, 2, or 3 substituents; each said substituent at each occurrence is independently optionally selected from D, halogen, —OH, —CN, —$NH_2$, —$NO_2$, —COOH, —$C_{1-3}$alkyl or —$C_{1-3}$alkoxy;
Y at each occurrence is independently selected from O or S;
$R_7$ at each occurrence is independently selected from H, D, —$C_{1-6}$alkyl, —$C_{1-6}$alkoxy, —$C_{3-8}$cycloalkyl or 3-8 membered heterocyclic, and $R_7$ at each occurrence is independently optionally substituted or unsubstituted with one or more substituents selected from D, —F, —Cl, —Br, —I, —OH, oxo, =O, —SH, —CN, —NO$_2$, —N$_3$, —C$_{1-3}$alkyl, —C$_{1-3}$alkoxy, —C$_{2-4}$alkenyl, —C$_{2-4}$ akynyl, —C$_{1-3}$haloalkyl, —C$_{3-6}$cycloalkyl, 3-6 membered heterocyclic, 3-6 membered heterocyclyloxy, 3-6 membered heterocyclylthio, C$_{5-8}$aryl, C$_{5-8}$aryloxy, C$_{5-8}$arylthio, 5-8 membered heteroaryl ring, 5-8 membered heteroaryloxy, 5-8 membered heteroarylthio, —S(O)$_t$R$_9$, —C$_{1-3}$alkyl-S(O)$_t$R$_9$, —O—R$_{10}$, —C$_{1-3}$alkyl-O—R$_{10}$, —C(O)OR$_{10}$, —C$_{1-3}$alkyl-C(O)OR$_{10}$, —C(O)R$_{11}$, —C$_{1-3}$alkyl-C(O)R$_1$, —O—C(O)R$_{11}$, —C$_{1-3}$alkyl-O—C(O)R$_{11}$, —NR$_{12}$R$_{13}$, —C$_{1-3}$alkyl-NR$_{12}$R$_{13}$, —C(O)NR$_{12}$R$_{13}$, —C$_{1-3}$alkyl-C(O)NR$_{12}$R$_{13}$, —N(R$_{12}$)—C(O)R$_n$ or —N(R$_{12}$)—C(O)OR$_{10}$;

R$_8$ at each occurrence is independently selected from H, D, —C$_{1-6}$alkyl, —C$_{1-6}$alkoxy, —C$_{2-6}$alkenyl, —C$_{2-6}$akynyl, —C(O)R$_{11}$, —C$_{1-6}$alkyl-C(O)R$_{11}$, —C$_{3-6}$cycloalkyl, 3-8 membered heterocyclic, and R$_8$ at each occurrence is independently optionally substituted or unsubstituted with one or more substituents selected from D, —F, —Cl, —Br, —I, —OH, oxo, =O, —SH, —CN, —NO$_2$, —N$_3$, —C$_{1-3}$alkyl, —C$_{2-4}$alkenyl, —C$_{2-4}$ akynyl, —C$_{1-3}$haloalkyl, —C$_{3-6}$cycloalkyl, 3-6 membered heterocyclic, 3-6 membered heterocyclyloxy, 3-6 membered heterocyclylthio, C$_{5-8}$ aryl, C$_{5-8}$ aryloxy, C$_{5-8}$ arylthio, 5-8 membered heteroaryl ring, 5-8 membered heteroaryloxy, 5-8 membered heteroarylthio, —S(O)$_1$R$_9$, —C$_{1-3}$alkyl-S(O)$_1$R$_9$, —O—R$_{10}$, —C$_{1-3}$alkyl-O—R$_{10}$, —C(O)OR$_{10}$, —C$_{1-3}$alkyl-C(O)OR$_{10}$, —C(O)R$_{11}$, —C$_{1-3}$alkyl-C(O)R$_n$, —O—C(O)R$_{11}$, —C$_{1-3}$alkyl-O—C(O)R$_n$, —NR$_{12}$R$_{13}$, —C$_{1-3}$alkylNR$_{12}$R$_{13}$, —C(O)NR$_{12}$R$_{13}$, —C$_{1-3}$alkyl-C(O)NR$_{12}$R$_{13}$, —N(R$_{12}$)—C(O)R$_n$ or —N(R$_{12}$)—C(O)OR$_{10}$; or R$_7$ and R$_8$ together with the carbon and nitrogen to which they are respectively attached form 5-10 membered monocyclic heterocyclic, 5-12 membered spirocyclic heterocyclic, 5-12 membered fused heterocyclic, or 5-12 membered bridged heterocyclic, and each said ring system at each occurrence is independently optionally substituted or unsubstituted with one or more substituents selected from D, —F, —Cl, —Br, —I, —OH, oxo, =O, —SH, —CN, —NO$_2$, —N$_3$, —C$_{1-3}$alkyl, —C$_{1-3}$alkoxy, —C$_{2-4}$alkenyl, —C$_{2-4}$ alkynyl, —C$_{1-3}$haloalkyl, —C$_{3-6}$cycloalkyl, substituted or unsubstituted 3-6 membered heterocyclic, 3-6 membered heterocyclyloxy, 3-6 membered heterocyclylthio, C$_{5-8}$ aryl, C$_{5-8}$ aryloxy, C$_{5-8}$ arylthio, 5-8 membered heteroaryl ring, 5-8 membered heteroaryloxy, 5-8 membered heteroarylthio, —S(O)$_1$R$_9$, —C$_{1-3}$alkyl-S(O)$_1$R$_9$, —O—R$_{10}$, —C$_{1-3}$alkyl-O—R$_{10}$, —C(O)OR$_{10}$, —C$_{1-3}$alkyl-C(O)OR$_{10}$, —C(O)R$_{11}$, —C$_{1-3}$alkyl-C(O)R$_{11}$, —O—C(O)R$_{11}$, —C$_{1-3}$alkyl-O—C(O)R$_n$, —NR$_{12}$R$_{13}$, —C$_{1-3}$alkyl-NR$_{12}$R$_{13}$, —C(O)NR$_{12}$R$_{13}$, —C$_{1-3}$alkyl-C(O)NR$_{12}$R$_{13}$, —N(R$_{12}$)—C(O)R$_n$ or —N(R$_{12}$)—C(O)OR$_{10}$;

R$_2$ and R$_3$ at each occurrence are independently selected from H; D; —F; —Cl; —Br; —I; —OH; —SH; —CN; —NH$_2$; —NO$_2$; —N$_3$; —C$_{1-6}$alkyl; —C$_{1-6}$alkyl; —C$_{1-6}$alkyl substituted with 1, 2 or 3 substituents selected from -D, —F, —Cl, —Br, —I, —OH, —CN, —NH$_2$, —NO$_2$, —COOH, —C$_{1-3}$alkyl or —C$_{1-3}$alkoxy; C$_{1-6}$alkoxy; —C$_{1-6}$ alkoxy substituted with 1, 2 or 3 substituents selected from -D, —F, —Cl, —Br, —I, —OH, —CN, —NH$_2$, —NO$_2$, —COOH, —C$_{1-3}$alkyl or —C$_{1-3}$alkoxy; substituted or unsubstituted C$_{3-8}$cycloalkyl; substituted or unsubstituted 3-8 membered heterocyclic; substituted or unsubstituted 3-8 membered heterocyclyloxy; substituted or unsubstituted 3-8 membered heterocyclylthio; —S(O)$_1$R$_9$; C$_{1-6}$alkyl-S(O)$_1$R$_9$; —O—R$_{10}$; —C$_{1-6}$alkyl-O—R$_{10}$; —C(O)OR$_{10}$; —C$_{1-6}$alkyl-C(O)OR$_{10}$; —C(O)R$_{11}$; —C$_{1-6}$alkyl-C(O)R$_{11}$; —O—C(O)R$_{11}$; —C$_{1-6}$alkyl-O—C(O)R$_n$; —NR$_{12}$R$_{13}$; —C$_{1-6}$alkyl-NR$_{12}$R$_{13}$; —C(O)NR$_{12}$R$_{13}$; —C$_{1-6}$alkyl-C(O)NR$_{12}$R$_{13}$; —N(R$_{12}$)—C(O)R$_{11}$ or —N(R$_{12}$)—C(O)OR$_{10}$;

G at each occurrence is independently selected from —CR$_{G1}$R$_{G2}$—, —S—, —SO—, —SO$_2$— or O; m is 0, 1, 2, 3 or 4;

Each R$_{G1}$ and R$_{G2}$ at each occurrence is independently selected from H; D; —C$_{1-6}$alkyl; —C$_{1-6}$alkyl substituted with 1, 2 or 3 substituents; —C$_{1-6}$alkoxy; —C$_{1-6}$alkoxy substituted with 1, 2 or 3 substituents; each said substituent is independently optionally selected from D, halogen, —OH, —CN, —NH$_2$, —NO$_2$, —COOH, —C$_{1-3}$alkyl or C$_{1-3}$alkoxy;

Q at each occurrence is independently selected from —CR$_4$R$_4$'—(CR$_4$R$_4$')$_q$— or —NR$_4$—(CR$_4$R$_4$')$_q$—, and q is selected from 0, 1, 2, 3 or 4;

R$_4$ and R$_4$' at each occurrence are independently selected from H; D; —F; —Cl; —Br; —I; —OH; —C$_{1-6}$alkyl; —C$_{1-6}$alkyl substituted with 1, 2 or 3 substituents; —C$_{1-6}$ alkoxy; —C$_{1-6}$alkoxy substituted with 1, 2 or 3 substituents; —C$_{3-8}$cycloalkyl; C$_{3-8}$cycloalkyl substituted with 1, 2 or 3 substituents; C$_{3-8}$ heterocyclic; 3-8 membered heterocyclic substituted with 1, 2 or 3 substituents; each said substituent at each occurrence is independently optionally selected from D, halogen, —OH, —CN, —NH$_2$, —NO$_2$, —COOH, —C$_{1-3}$alkyl or C$_{1-3}$alkoxy; or R$_4$ and R$_4$' together with the carbon to which they are both attached form C$_{3-8}$ carbocyclic ring, 3-8 membered heterocyclic ring or 5-10 membered heteroaryl ring, and each ring system at each occurrence is independently optionally substituted or unsubstituted with one or more substituents;

R$_5$ and R$_5$' at each occurrence are independently selected from H; D; —F; —Cl; —Br; —I; —OH; —C$_{1-6}$alkyl; —C$_{1-6}$alkyl substituted with 1, 2 or 3 substituents; —C$_{1-6}$ alkoxy; —C$_{1-6}$alkoxy substituted with 1, 2 or 3 substituents; —C$_{3-8}$cycloalkyl; C$_{3-8}$cycloalkyl substituted with 1, 2 or 3 substituents; 3-8 membered heterocyclic; 3-8 membered heterocyclic substituted with 1, 2 or 3 substituents; each said substituent is independently optionally selected from D, halogen, —OH, —CN, —NH$_2$, —NO$_2$, —COOH, —C$_{1-3}$alkyl or C$_{1-3}$alkoxy; or R$_5$ and R$_5$' together with the carbon to which they are both attached form —C$_{3-8}$ carbocyclic ring, 3-8 membered heterocyclic ring, 5-10 membered heteroaryl ring, and each said heterocyclic and each said heteroaryl at each occurrence independently optionally contains one or two heteroatoms selected from N, O or S, and each said ring system at each occurrence is independently optionally substituted or unsubstituted with one or more substituents; or R$_4$ and R$_5$ together with the atom to which they are respectively attached form 5-10 membered aromatic ring, —C$_{3-10}$ carbocyclic, 4-10 membered heterocyclic ring, each said heterocyclic at each occurrence independently optionally contains one or two heteroatoms selected from N, O or S, and each said ring system at each occurrence is independently optionally substituted or unsubstituted with one or more substituents;

W at each occurrence is independently selected from —(CR$_{w1}$R$_{w2}$)$_n$—S—, —(CR$_{w1}$R$_{w2}$)$_n$—SO— or —(CR$_{w1}$R$_{w2}$)$_n$—SO$_2$—, n is selected from 0, 1, 2, 3 or 4;

R$_{w1}$ and R$_{w2}$ at each occurrence are independently selected from H; D; —F; —Cl; —Br; —OH; methyl; ethyl; propyl; isopropyl; —C$_{1-3}$alkyl substituted with 1, 2 or 3 substituents; methoxy; ethoxy; propoxy; isopropoxy; —C$_{1-3}$ alkoxy substituted with 1, 2 or 3 substituents; cyclopropyl; cyclobutyl; cyclopentyl; cyclohexyl; —C$_{3-6}$cycloalkyl substituted with 1, 2 or 3 substituents; 3 membered heterocyclic;

4 membered heterocyclic; 5 membered heterocyclic; 6 membered heterocyclic or 3-6 membered heterocyclic substituted with 1, 2 or 3 substituents; and each said substituent at each occurrence is independently optionally selected from D, —F, —Cl, —Br, —I, —OH, —CN, —NH$_2$, —NO$_2$, —COOH, methyl, ethyl, propyl, isopropyl, methoxy, ethoxy, propoxy, or isopropoxy;

$R_6$ at each occurrence is independently selected from H; D; —F; —Cl; —Br; —I; —C$_{1-3}$alkyl; —C$_{1-3}$alkyl substituted with 1, 2 or 3 substituents; —C$_{1-3}$alkoxy; —C$_{1-3}$alkoxy substituted with 1, 2 or 3 substituents; —C$_{1-3}$alkyl-COO—C$_{1-3}$alkyl; —C$_{3-6}$cycloalkyl or —C$_{3-6}$cycloalkyl substituted with 1, 2 or 3 substituents; and each said substituent is independently optionally selected from D, halogen, —OH, —CN, —NH$_2$, —NO$_2$, —COOH, —C$_{1-3}$alkyl or C$_{1-3}$alkoxy; or Q and $R_6$ together with the carbon and W to which they are respectively attached form 4-6 membered heterocyclic ring, the heterocyclic ring is independently optionally substituted or unsubstituted with one or more substituents, and the heterocyclic ring independently optionally contains 1, 2, or 3 heteroatoms selected from N, O or S, and each said substituent is independently optionally selected from D, halogen, —OH, —CN, —NH$_2$, —NO$_2$, —COOH, —C$_{1-3}$alkyl or C$_{1-3}$alkoxy; or $R_4$ and $R_6$ together with the atom to which they are respectively attached form 5-8 membered monocyclic heterocyclic, 5-10 membered spirocyclic heterocyclic, 5-10 membered fused heterocyclic, 5-10 membered bridged heterocyclic or 5-10 membered heteroaryl ring, and each said ring system independently optionally contains 1, 2 or 3 heteroatoms selected from N, O or S, and each said ring system is independently optionally substituted or unsubstituted with 1, 2, or 3 substituents selected from D, —F, —Cl, —Br, —I, —OH, —NH$_2$, —CN, —COOH, oxo, =O, —C$_{1-3}$alkyl or C$_{1-3}$alkoxy; or $R_5$ and $R_6$ together with the carbon and W to which they are respectively attached form 4-6 membered heterocyclic ring or 5-8 membered heteroaryl ring, each said ring system independently optionally contains 1, 2 or 3 heteroatoms selected from N, O or S, and each said ring system is independently optionally substituted or unsubstituted with 1, 2, or 3 substituents selected from D, —F, —Cl, —Br, —I, —OH, —NH$_2$, —CN, —COOH, oxo, =O, —C$_{1-3}$alkyl or C$_{1-3}$alkoxy;

Each $R_9$ at each occurrence is independently selected from H, D, —C$_{1-3}$alkyl, —C$_{1-3}$alkyl C$_{1-3}$alkoxy, —C$_{2-4}$alkenyl, —C$_{3-6}$cycloalkyl, substituted or unsubstituted 3-6 membered heterocyclic, C$_{1-3}$haloalkyl, phenyl, p-methyl phenyl, amino, —NH—C$_{1-3}$alkyl, —N(C$_{1-3}$alkyl)$_2$ or C$_{1-3}$alkylamide;

Each $R_{10}$ at each occurrence is independently selected from H, D, —C$_{1-3}$alkyl, —C$_{1-3}$alkyl C$_{1-3}$alkoxy, —C$_{3-6}$cycloalkyl, —C$_{5-10}$ aryl, C$_{1-3}$haloalkyl, or C$_{1-3}$alkyl substituted with hydroxyl;

Each $R_{11}$ at each occurrence is independently selected from H, D, —C$_{1-3}$alkyl, —C$_{1-3}$alkoxy, —C$_{3-6}$cycloalkyl, —C$_{3-6}$cycloalkoxy, C$_{1-3}$haloalkyl, C$_{1-3}$haloalkoxy, C$_{1-3}$alkyl substituted with hydroxyl, or C$_{1-3}$alkoxy substituted with hydroxyl;

$R_{12}$ and $R_{13}$ at each occurrence are independently selected from H, D, —C$_{1-3}$alkyl, —C$_{1-3}$alkyl C$_{1-3}$alkoxy, —C$_{1-3}$alkoxy C$_{1-3}$alkyl, —C$_{3-6}$cycloalkyl C$_{1-3}$alkyl, —C$_{2-4}$alkenyl, —C$_{2-4}$alkynyl, —C$_{3-6}$cycloalkyl, substituted or unsubstituted C$_{5-10}$ aryl, substituted or unsubstituted 5-10 membered heteroaryl, or C$_{1-3}$alkanoyl;

t at each occurrence is independently selected from 0, 1 or 2.

In some embodiments, $R_1$ at each occurrence is independently

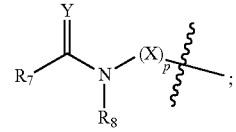

X at each occurrence is independently selected from absent, O, —NR$_{X1}$— or —CR$_{X1}$R$_{X2}$—; and p is 0, 1 or 2;

$R_{X1}$ and $R_{X2}$ at each occurrence are independently selected from H; D; —F; —Cl; —Br; —I; —C$_{1-3}$alkyl; C$_{1-3}$alkyl substituted with 1, 2 or 3 substituents; C$_{1-3}$alkoxy or C$_{1-3}$alkoxy substituted with 1, 2 or 3 substituents; each said substituent is independently optionally selected from D, —F, —Cl, —Br, —I, —OH, —CN, —NH$_2$, —NO$_2$, —COOH, —C$_{1-3}$alkyl or C$_{1-3}$alkoxy;

Y at each occurrence is independently selected from O or S;

$R_7$ at each occurrence is independently selected from H, D, —C$_{1-3}$alkyl, —C$_{1-3}$alkoxy, —C$_{3-5}$cycloalkyl or 3-8 membered heterocyclic, and the heterocyclic independently optionally contains 1, 2 or 3 heteroatoms selected from N, O or S, and $R_7$ at each occurrence is independently optionally substituted or unsubstituted with one or more substituents selected from D, —F, —Cl, —Br, —I, —OH, oxo, =O, —SH, —CN, —NO$_2$, —N$_3$, —C$_{1-3}$alkyl, —C$_{1-3}$alkoxy, —C$_{2-4}$alkenyl, —C$_{2-4}$alkynyl, C$_{1-3}$haloalkyl, C$_{3-6}$cycloalkyl, 3-6 membered heterocyclic, 3-6 membered heterocyclyloxy, 3-6 membered heterocyclylthio, C$_{5-8}$ aryl, C$_{5-8}$aryloxy, C$_{5-8}$arylthio, 5-8 membered heteroaryl ring, 5-8 membered heteroaryloxy, 5-8 membered heterocyclylthio, —S(O)$_t$R$_9$, —C$_{1-3}$alkyl-S(O)$_t$R$_9$, —C$_{1-3}$alkyl-O—R$_{10}$, —C(O)OR$_{10}$, —C$_{1-3}$alkyl-C(O)OR$_{10}$, —C(O)R$_{11}$, —C$_{1-3}$alkyl-C(O)R$_{11}$, —O—C(O)R$_{11}$, —C$_{1-3}$alkyl-O—C(O)R$_{11}$, —NR$_{12}$R$_{13}$, —C$_{1-3}$alkyl-NR$_{12}$R$_{13}$, —C(O)NR$_{12}$R$_{13}$, —C$_{1-3}$alkyl-C(O)NR$_{12}$R$_{13}$, —N(R$_{12}$)—C(O)R$_{11}$ or —N(R$_{12}$)—C(O)OR$_{10}$;

$R_8$ at each occurrence is independently selected from H, D, —C$_{1-3}$alkoxy, —C$_{2-4}$alkenyl, —C$_{2-4}$alkynyl, —C(O)R$_{11}$, —C$_{1-3}$alkyl-C(O)R$_{11}$, —C$_{3-6}$cycloalkyl, or 3-8 membered heterocyclic, R$_8$ is independently optionally substituted or unsubstituted with one or more substituents selected from D, —F, —Cl, —Br, —I, —OH, oxo, =O, —SH, —CN, —NO$_2$, —N$_3$, —C$_{1-3}$alkyl, —C$_{2-4}$alkenyl, —C$_{2-4}$alkynyl, C$_{1-3}$haloalkyl, —C$_{3-6}$cycloalkyl, 3-6 membered heterocyclic, 3-6 membered heterocyclyloxy, 3-6 membered heterocyclylthio, C$_{5-8}$ aryl, C$_{5-8}$aryloxy, C$_{5-8}$arylthio, 5-8 membered heteroaryl ring, 5-8 membered heteroaryloxy, 5-8 membered heterocyclylthio, —S(O)$_t$R$_9$, —C$_{1-3}$alkyl-S(O)$_t$R$_9$, —O—R$_{10}$, —C$_{1-3}$alkyl-O—R$_{10}$, —C(O)OR$_{10}$, —C$_{1-3}$alkyl-C(O)OR$_{10}$, —C(O)R$_{11}$, —C$_{1-3}$alkyl-C(O)R$_{11}$, —O—C(O)R$_{11}$, —C$_{1-3}$alkyl-O—C(O)R$_{11}$, —NR$_{12}$R$_{13}$, —C$_{1-3}$alkyl-NR$_{12}$R$_{13}$, —C(O)NR$_{12}$R$_{13}$, —C$_{1-3}$alkyl-C(O)NR$_{12}$R$_{13}$, —N(R$_{12}$)—C(O)R$_{11}$ or —N(R$_{12}$)—C(O)OR$_{10}$; or $R_7$ and $R_8$ together with the carbon and nitrogen to which they are respectively attached form 5-7 membered monocyclic heterocyclic, 5-10 membered spirocyclic heterocyclic, 5-10 membered fused heterocyclic or 5-10 membered bridged heterocyclic, each said ring system is independently optionally contains 1, 2 or 3 heteroatoms selected from N, O or S, and each said ring system is independently optionally substituted or unsubstituted with one or more substituents selected from D, —F, —Cl, —Br, —I, —OH, oxo, =O, —SH, —CN, —NO$_2$, —N$_3$, —C$_{1-3}$alkyl, —C$_{1-3}$alkoxy, —C$_{2-4}$alkenyl, —C$_{2-4}$alkynyl, C$_{1-3}$haloalkyl, —C$_{3-6}$cycloalkyl, substituted or unsubstituted 3-6 membered heterocyclic, 3-6 membered heterocyclyloxy, 3-6 membered heterocyclylthio, C$_{5-8}$ aryl, C$_{5-8}$aryloxy, C$_{5-8}$arylthio, 5-8 membered heteroaryl ring, 5-8 membered heteroaryloxy, 5-8 membered heterocyclylthio, —S(O)$_1$R$_9$, —C$_{1-3}$alkyl-S(O)$_1$R$_9$, —O—R$_{10}$, —C(O)OR$_{10}$, —C$_{1-3}$alkyl-C(O)OR$_{10}$, —C(O)R$_{11}$, —C$_{1-3}$alkyl-C(O)R$_{11}$, —O—C(O)R$_{11}$, —C$_{1-3}$alkyl-O—C(O)R$_{11}$, —NR$_{12}$R$_{13}$, —C$_{1-3}$alkyl-NR$_{12}$R$_{13}$, —C(O)NR$_{12}$R$_{13}$, —C$_{1-3}$alkyl-C(O)NR$_{12}$R$_{13}$, —N(R$_{12}$)—C(O)R$_{11}$ or —N(R$_{12}$)—C(O)OR$_{10}$;

In R$_7$ and R$_8$, each R$_9$ is independently optionally selected from H, D, —C$_{1-3}$alkyl C$_{1-3}$alkoxy, —C$_{2-4}$alkenyl, —C$_{3-6}$cycloalkyl, substituted or unsubstituted 3-6 membered heterocyclic, C$_{1-3}$haloalkyl, phenyl, p-methyl phenyl, amino, —NH—C$_{1-3}$alkyl, —N(C$_{1-3}$alkyl)$_2$ or C$_{1-3}$alkylamide;

In R$_7$ and R$_8$, each R$_{10}$ is independently optionally selected from H, D, —C$_{1-3}$alkyl C$_{1-3}$alkoxy, —C$_{3-6}$cycloalkyl, C$_{1-3}$haloalkyl or C$_{1-3}$alkyl substituted with hydroxyl;

In R$_7$ and R$_8$, each R$_{11}$ is independently optionally selected from H, D, —C$_{1-3}$alkoxy, —C$_{3-6}$cycloalkyl, —C$_{3-6}$cycloalkoxy, C$_{1-3}$haloalkyl, C$_{1-3}$haloalkoxy, C$_{1-3}$alkyl substituted with hydroxyl, or C$_{1-3}$alkoxy substituted with hydroxyl;

In R$_7$ and R$_8$, R$_{12}$ and R$_{13}$ are respectively independently selected from H, D, —C$_{1-3}$alkyl C$_{1-3}$alkoxy, —C$_{1-3}$alkoxy C$_{1-3}$alkyl, —C$_{3-6}$cycloalkyl C$_{1-3}$alkyl, —C$_{2-4}$alkenyl, —C$_{2-4}$alkynyl, —C$_{3-6}$cycloalkyl, substituted or unsubstituted —C$_{5-10}$aryl, substituted or unsubstituted 5-10 membered heteroaryl or —C$_{1-3}$alkanoyl;

t is 0, 1 or 2.

In some embodiments, R$_1$ at each occurrence is independently

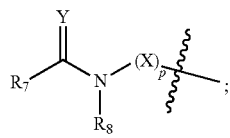

X at each occurrence is independently selected from absent, 0, —NR$_{X1}$— or —CR$_{X1}$R$_{X2}$—; and p is 0 or 1;

R$_{X1}$ and R$_{X2}$ at each occurrence are independently selected from H; D; —F; —Cl; —Br; —I; methyl; ethyl; propyl; isopropyl; C$_{1-3}$alkyl substituted with 1, 2 or 3 substituents; methoxy; ethoxy; propoxy; isopropoxy or C$_{1-3}$alkoxy substituted with 1, 2 or 3 substituents; each said substituent is independently optionally selected from D, —F, —Cl, —Br, —I, —OH, —CN, —NH$_2$, —NO$_2$, —COOH, methyl, ethyl, propyl, isopropyl, methoxy, ethoxy, propoxy, or isopropoxy;

Y at each occurrence is independently O;

R$_7$ at each occurrence is independently selected from H, D, methyl, ethyl, propyl, isopropyl, methoxy, ethoxy, propoxy, isopropoxy, cyclopropyl, cyclobutyl, cyclopentyl, cyclohexyl, 3 membered heterocyclic, 4 membered heterocyclic, 5 membered heterocyclic, 6 membered heterocyclic, 7 membered heterocyclic, 8 membered heterocyclic, and each said heterocyclic independently optionally contains one or two heteroatoms selected from N, O or S, and R$_7$ at each occurrence is independently optionally substituted or unsubstituted with substituents selected from D, —F, —Cl, —Br, —I, —OH, oxo, =O, —SH, —CN, —NO$_2$, —N$_3$, methyl, ethyl, propyl, isopropyl, methoxy, ethoxy, propoxy, isopropoxy, —C$_{2-4}$alkenyl, —C$_{2-4}$alkynyl, C$_{1-3}$alkyl substituted with halogen, C$_{3-6}$cycloalkyl, 3-6 membered heterocyclic, 3-6 membered heterocyclyloxy, 3-6 membered heterocyclylthio, C$_{5-8}$ aryl, C$_{5-8}$ aryloxy, C$_{5-8}$ arylthio, 5-8 membered heteroaryl ring, 5-8 membered heteroaryloxy, 5-8 membered heterocyclylthio, —S(O)$_1$R$_9$, -methyl-S(O)$_1$R$_9$, -ethyl-S(O)$_1$R$_9$, -propyl-S(O)$_1$R$_9$, isopropyl-S(O)$_1$R$_9$, —O—R$_{10}$, -methyl-O—R$_{10}$, -ethyl-O—R$_{10}$, -propyl-O—R$_{10}$, -isopropyl-O—R$_{10}$, —C(O)OR$_{10}$, -methyl-C(O)OR$_{10}$, -ethyl-C(O)OR$_{10}$, -propyl-C(O)OR$_{10}$, -isopropyl-C(O)OR$_{10}$, —C(O)R$_n$, -methyl-C(O)R$_{11}$, -ethyl-C(O)R$_{11}$, -propyl-C(O)R$_{11}$, -isopropyl-C(O)R$_{11}$, —O—C(O)R$_{11}$, -methyl-O—C(O)R$_{11}$, -ethyl-O—C(O)R$_{11}$, -propyl-O—C(O)R$_{11}$, -isopropyl-O—C(O)R$_{11}$, —NR$_{12}$R$_{13}$, -methyl-NR$_{12}$R$_{13}$, -ethyl-NR$_{12}$R$_{13}$, -propyl-NR$_{12}$R$_{13}$, -isopropyl-NR$_{12}$R$_{13}$, —C(O)NR$_{12}$R$_{13}$, -methyl-C(O)NR$_{12}$R$_{13}$, -ethyl-C(O)NR$_{12}$R$_{13}$, -propyl-C(O)NR$_{12}$R$_{13}$, -isopropyl-C(O)NR$_{12}$R$_{13}$, —N(R$_{12}$)—C(O)R$_n$ or —N(R$_{12}$)—C(O)OR$_{10}$;

R$_8$ at each occurrence is independently selected from H, D, methyl, ethyl, propyl, isopropyl, methoxy, ethoxy, propoxy, isopropoxy, —C$_{2-4}$alkenyl, —C$_{2-4}$alkynyl, —C(O)R$_{11}$, -methyl-C(O)R$_{11}$, -ethyl-C(O)R$_{11}$, -propyl-C(O)R$_{11}$, -isopropyl —C(O)R$_{11}$, cyclopropyl, cyclobutyl, cyclopentyl, cyclohexyl, 3 membered heterocyclic, 4 membered heterocyclic, 5 membered heterocyclic, 6 membered heterocyclic, 7 membered heterocyclic, 8 membered heterocyclic, and said heterocyclic independently optionally contains one or two heteroatoms selected from N, O or S, and R$_8$ is independently optionally substituted or unsubstituted with one or more substituents selected from D, —F, —Cl, —Br, —I, —OH, oxo, =O, —SH, —CN, —NO$_2$, —N$_3$, methyl, ethyl, propyl, isopropyl, C$_{2-4}$alkenyl, C$_{2-4}$alkynyl, C$_{1-3}$haloalkyl, C$_{3-6}$cycloalkyl, 3-6 membered heterocyclic, 3-6 membered heterocyclyloxy, 3-6 membered heterocyclylthio, C$_{5-8}$ aryl, C$_{5-8}$ aryloxy, C$_{1-8}$arylthio, 5-8 membered heteroaryl ring, 5-8 membered heteroaryloxy, 5-8 membered heterocyclylthio, —S(O)$_1$R$_9$, -methyl-S(O)$_1$R$_9$, -ethyl-S(O)$_1$ R$_9$, -propyl-S(O)$_1$R$_9$, isopropyl-S(O)$_1$R$_9$, —O—R$_{10}$, -methyl-O—R$_{10}$, -ethyl-O—R$_{10}$, -propyl-O—R$_{10}$, -isopropyl-O—R$_{10}$, —C(O)OR$_{10}$, -methyl-C(O)OR$_{10}$, -ethyl-C(O)OR$_{10}$, -propyl-C(O)OR$_{10}$, -isopropyl-C(O)OR$_{10}$, —C(O)R$_{11}$, -methyl-C(O)R$_{11}$, -ethyl-C(O)R$_{11}$, -propyl-C(O)R$_{11}$, -isopropyl-C(O)R$_{11}$, —O—C(O)R$_{11}$, -methyl-O—C(O)R$_{11}$, -ethyl-O—C(O)R$_{11}$, -propyl-O—C(O)R$_{11}$, -isopropyl-O—C(O)R$_{11}$, —NR$_{12}$R$_{13}$, -methyl-NR$_{12}$R$_{13}$, -ethyl —NR$_{12}$R$_{13}$, -propyl-NR$_{12}$R$_{13}$, -isopropyl-NR$_{12}$R$_{13}$, —C(O)NR$_{12}$R$_{13}$, -methyl-C(O)NR$_{12}$R$_{13}$, -ethyl-C(O)NR$_{12}$R$_{13}$, -propyl-C(O)NR$_{12}$R$_{13}$, -isopropyl-C(O)NR$_{12}$R$_{13}$, —N(R$_{12}$)—C(O)R$_{11}$ or —N(R$_{12}$)—C(O)OR$_{10}$; or R$_7$ and R$_8$ together with the carbon and nitrogen to which they are respectively attached form 5 membered monocyclic heterocyclic, 6 membered monocyclic heterocyclic, 7 membered monocyclic heterocyclic, 5 membered spirocyclic heterocyclic, 6 membered spirocyclic heterocyclic, 7 membered spirocyclic heterocyclic, 8 membered spirocyclic heterocyclic, 9 membered spirocyclic heterocyclic, 10 membered spirocyclic heterocyclic, 5 membered fused heterocyclic, 6 membered fused heterocyclic, 7 membered fused heterocyclic, 8 membered fused heterocyclic, 9 membered fused heterocyclic, 10 membered fused heterocyclic, 5 membered bridged heterocyclic, 6 membered bridged heterocyclic, 7 membered bridged heterocyclic, 8 membered bridged heterocyclic, 9 membered bridged heterocyclic, or 10 membered bridged heterocyclic, each said ring system independently optionally contains 1, 2 or 3 heteroatoms selected from N, O or S, and each said ring system is independently optionally substituted or unsubstituted with one or more substituents selected from D, —F, —Cl, —Br, —I, —OH, oxo, =O, —SH, —CN, —NO$_2$, —N$_3$, methyl, ethyl, propyl, isopropyl, methoxy, ethoxy, propoxy, isopropoxy, C$_{2-4}$alkenyl, C$_{2-4}$alkynyl, C$_{1-3}$ haloalkyl, cyclopropyl, cyclobutyl, cyclopentyl, cyclohexyl, substituted or unsubstituted 3-6 membered heterocyclic, 3-6 membered heterocyclyloxy, 3-6 membered heterocyclylthio, C$_{5-8}$ aryl, C$_{5-8}$ aryloxy, C$_{5-8}$arylthio, 5-8 membered heteroaryl ring, 5-8 membered heteroaryloxy, 5-8 membered heterocyclylthio, —S(O)$_1$R$_9$, -methyl-S(O)$_1$R$_9$, -ethyl-S(O)$_1$R$_9$, -propyl-S(O)$_1$R$_9$, -isopropyl-S(O)$_1$R$_9$, —O—R$_{10}$, -methyl-O—R$_{10}$, -ethyl-O—R$_{10}$, -propyl-O—R$_{10}$, -isopropyl-O—R$_{10}$, —C(O)OR$_{10}$, -methyl-C(O)OR$_{10}$, -ethyl-C(O)OR$_{10}$, -propyl-C(O)OR$_{10}$, -isopropyl-C(O)OR$_{10}$, —C(O)R$_{11}$, -methyl-C(O)R$_{11}$, -ethyl-C(O)R$_{11}$, -propyl-C(O)R$_{11}$, -isopropyl-C(O)R$_{11}$, —O—C(O)R$_{11}$, -methyl-O—C(O)R$_{11}$, -ethyl-O—C(O)R$_{11}$, -propyl-O—C(O)R$_{11}$, -isopropyl-O—C(O)R$_{11}$, —NR$_{12}$R$_{13}$, -methyl-NR$_{12}$R$_{13}$, -ethyl-NR$_{12}$R$_{13}$, -propyl-NR$_{12}$R$_{13}$, -isopropyl-NR$_{12}$R$_{13}$, —C(O)NR$_{12}$R$_{13}$, -methyl-C(O)NR$_{12}$R$_{13}$, -ethyl-C(O)NR$_{12}$R$_{13}$, -propyl-C(O)NR$_{12}$R$_{13}$, -isopropyl-C(O)NR$_{12}$R$_{13}$, —N(R$_{12}$)—C(O)R$_{11}$ or —N(R$_{12}$)—C(O)OR$_{10}$;

In R$_7$ and R$_8$, each R$_9$ is independently optionally selected from H, D, methyl, ethyl, propyl, isopropyl, —C$_{1-3}$alkylC$_{1-3}$alkoxy, —C$_{2-4}$alkenyl, cyclopropyl, cyclobutyl, cyclopentyl, cyclohexyl, substituted or unsubstituted 3-6 membered heterocyclic, C$_{1-3}$haloalkyl, phenyl, p-methyl phenyl, amino, —NH—C$_{1-3}$alkyl, —N(C$_{1-3}$alkyl)$_2$ or C$_{1-3}$alkylamide;

In R$_7$ and R$_8$, each R$_{10}$ is independently optionally selected from H, D, methyl, ethyl, propyl, isopropyl, —C$_{1-3}$alkylC$_{1-3}$alkoxy, —C$_{3-6}$cycloalkyl, —C$_{5-10}$ aryl, C$_{1-3}$haloalkyl or C$_{1-3}$alkyl substituted with hydroxyl;

In R$_7$ and R$_8$, each R$_{11}$ is independently optionally selected from H, D, methyl, ethyl, propyl, isopropyl, methoxy, ethoxy, propoxy, isopropoxy, cyclopropyl, cyclobutyl, cyclopentyl, cyclohexyl, C$_{3-6}$ membered cycloalkoxy, C$_{1-3}$haloalkyl, C$_{1-3}$haloalkoxy, C$_{1-3}$alkyl substituted with hydroxyl, or C$_{1-3}$alkoxy substituted with hydroxyl;

In R$_7$ and R$_8$, R$_{12}$ and R$_{13}$ are respectively independently selected from H, D, methyl, ethyl, propyl, isopropyl, —C$_{1-3}$alkylC$_{1-3}$alkoxy, —C$_{1-3}$alkoxy C$_{1-3}$alkyl, —C$_{3-6}$cycloalkyl C$_{1-3}$alkyl, —C$_{2-4}$alkenyl, —C$_{2-4}$alkynyl, cyclopropyl, cyclobutyl, cyclopentyl, cyclohexyl, substituted or unsubstituted C$_{5-10}$ aryl, substituted or unsubstituted 5-10 membered heteroaryl or —C$_{1-3}$alkylamide;

t is 0, 1 or 2.

In some embodiments, R$_1$ at each occurrence is independently

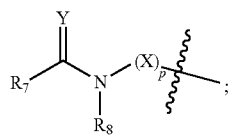

X at each occurrence is independently selected from —CH2-, —CHD-, —CD$_2$-, —CH(CH$_3$)—, —C(CH$_3$)$_2$—, —CHF—, —CHBr— or —CH(OH)—; and p is 0 or 1;

Y at each occurrence is independently 0;

R$_7$ at each occurrence is independently selected from H, D, methyl, ethyl, propyl, isopropyl, methoxy, ethoxy, propoxy, isopropoxy, cyclopropyl, cyclobutyl, cyclopentyl, cyclohexyl, dioxolane, azacyclobutyl, piperidyl, piperazinyl, oxopiperazinyl, oxypiperidyl, tetrahydrofuranyl, tetrahydroimidazolyl, tetrahydrothiazolyl, tetrahydrooxazolyl, tetrahydropyranyl, morpholinyl, thiomorpholinyl or oxadiazole, R$_7$ at each occurrence is independently optionally substituted or unsubstituted with one or more substituents selected from D, —F, —Cl, —Br, —I, —OH, oxo, =O, —SH, —CN, —NO$_2$, —N$_3$, methyl, ethyl, propyl, isopropyl, methoxy, ethoxy, propoxy, isopropoxy, —C$_{2-4}$alkenyl, —C$_{2-4}$alkynyl, C$_{1-3}$haloalkyl, C$_{3-6}$cycloalkyl, 3-6 membered heterocyclic, 3-6 membered heterocyclyloxy, 3-6 membered heterocyclylthio, C$_{5-8}$ aryl, C$_{5-8}$aryloxy, C$_{1-8}$arylthio, 5-8 membered heteroaryl ring, 5-8 membered heteroaryloxy, 5-8 membered heterocyclylthio, —S(O)H, —S(O)CH$_3$, -methyl-S(O)H, -methyl-S(O)CH$_3$, -ethyl-S(O)H, -ethyl-S(O)CH$_3$, -propyl-S(O)H, -propyl-S(O)CH$_3$, -isopropyl-S(O)H, -isopropyl-S(O)CH$_3$, -methyl-OH, -methyl-OCH$_3$, -ethyl-OH, -ethyl-OCH$_3$, -propyl-OH, -propyl-OCH$_3$, -isopropyl-OH, -isopropyl-OCH$_3$, —C(O)OH, —C(O)OCH$_3$, -methylC(O)OH, -methyl-C(O)OCH$_3$, -ethyl-C(O)OH, -ethyl-C(O)OCH$_3$, -propyl-C(O)OH, -propyl-C(O)OCH$_3$, -isopropyl-C(O)OH, -isopropyl-C(O)OCH$_3$, —C(O)H, —C(O)CH$_3$, -methyl-C(O)H, -methyl-C(O)CH$_3$, -ethyl-C(O)H, -ethyl-C(O)CH$_3$, -propyl-C(O)H, -propyl-C(O)CH$_3$, -isopropyl-C(O)H, -isopropyl-C(O)CH$_3$, —O—C(O)H, —O—C(O)CH$_3$, -methyl-O—C(O)H, -methyl-O—C(O)CH$_3$, -ethyl-O—C(O)H, -ethyl-O—C(O)CH$_3$, -propyl-O—C(O)H, -propyl-O—C(O)CH$_3$, -isopropyl-O—C(O)H, -isopropyl-O—C(O)CH$_3$, —NH$_2$, —N(CH$_3$)$_2$, -methyl-NH$_2$, -methyl-N(CH$_3$)$_2$, -ethyl-NH$_2$, -ethyl-N(CH$_3$)$_2$, -propyl-NH$_2$, -propyl-N(CH$_3$)$_2$, -isopropyl-NH$_2$, -isopropyl-N(CH$_3$)$_2$, —C(O)NH$_2$, —C(O)N(CH$_3$)$_2$, -methyl-C(O)NH$_2$, -methyl-C(O)N(CH$_3$)$_2$, -ethyl-C(O)NH$_2$, -ethyl-C(O)N(CH$_3$)$_2$, -propyl-C(O)NH$_2$, -propyl-C(O)N(CH$_3$)$_2$, -isopropyl-C(O)NH$_2$, -isopropyl-C(O)N(CH$_3$)$_2$, —NH—C(O)H or —NH—C(O)OH;

R$_8$ at each occurrence is independently selected from H, D, methyl, ethyl, propyl, isopropyl, methoxy, ethoxy, propoxy, isopropoxy, —C$_{2-4}$alkenyl, —C$_{2-4}$alkynyl, —C(O)H, -methyl-C(O)H, -ethyl-C(O)H, -propyl-C(O)H, -isopropyl-C(O)H, —C(O)-methyl, -methyl-C(O)-methyl, -ethyl-C(O)-methyl, -propoxy-C(O)methyl, -isopropoxy-C(O)-methyl, cyclopropyl, cyclobutyl, cyclopentyl, cyclohexyl, 3 membered heterocyclic, 4 membered heterocyclic, 5 membered heterocyclic, 6 membered heterocyclic, 7 membered heterocyclic, 8 membered heterocyclic, and said heterocyclic independently optionally contains 1 or 2 heteroatoms selected from N, O or S, and R$_8$ is independently optionally substituted or unsubstituted with one or more substituents selected from D, —F, —Cl, —Br, —I, —OH, oxo, =O, —SH, —CN, —NO$_2$, —N$_3$, methyl, ethyl, propyl, isopropyl, C$_{2-4}$alkenyl, C$_{2-4}$alkynyl, C$_{1-3}$haloalkyl, C$_{3-6}$cycloalkyl, 3-6 membered heterocyclic, 3-6 membered heterocyclyloxy, 3-6 membered heterocyclylthio, C$_{5-8}$ aryl, C$_{5-8}$ aryloxy, C$_{5-8}$ arylthio, 5-8 membered heteroaryl ring, 5-8 membered heteroaryloxy, 5-8 membered heterocyclylthio, —S(O)H, —S(O)CH$_3$, -methyl-S(O)H, -methyl-S(O)CH$_3$, -ethyl-S(O)H, -ethyl-S(O)CH$_3$, -propyl-S(O)H, -propyl-S(O)CH$_3$, -isopropyl-S(O)H, -isopropyl-S(O)CH$_3$, -methyl-OH, -methyl-OCH$_3$, -ethyl-OH, -ethyl-OCH$_3$, -propyl-OH, -propyl-OCH$_3$, -isopropyl-OH, -isopropyl-OCH$_3$, —C(O)OH, —C(O)OCH$_3$, -methyl-C(O)OH, -methylC(O)OCH$_3$, -ethyl-C(O)OH, -ethyl-C(O)OCH$_3$, -propyl-C(O)OH, -propyl-C(O)OCH$_3$, -isopropyl-C(O)OH, -isopropyl-C(O)OCH$_3$, —C(O)H, —C(O)CH$_3$, -methyl-C(O)H, -methyl-C(O)CH$_3$, -ethyl-C(O)H, -ethyl-C(O)CH$_3$, -propyl-C(O)H, -propyl-C(O)CH₃, -isopropyl-C(O)H, -isopropyl-C(O)CH₃, —O—C(O)H, —O—C(O)CH₃, -methyl-O—C(O)H, -methyl-O—C(O)CH₃, -ethyl-O—C(O)H, -ethyl-O—C(O)CH₃, -propyl-O—C(O)H, -propyl-O—C(O)CH₃, -isopropyl-O—C(O)H, -isopropyl-O—C(O)CH₃, —NH₂, —N(CH₃)₂, -methyl-NH₂, -methyl-N(CH₃)₂, -ethyl-NH₂, -ethyl-N(CH₃)₂, -propyl-NH₂, -propyl-N(CH₃)₂, -isopropyl-NH₂, -isopropyl-N(CH₃)₂, —C(O)NH₂, —C(O)N(CH₃)₂, -methyl-C(O)NH₂, -methyl-C(O)N(CH₃)₂, -ethyl-C(O)NH₂, -ethyl-C(O)N(CH₃)₂, -propyl-C(O)NH₂, -propyl-C(O)N(CH₃)₂, -isopropyl-C(O)NH₂, -isopropyl-C(O)N(CH₃)₂, —NH—C(O)H or —NH—C(O)OH;

R₇ and R₈ together with the carbon and nitrogen to which they are respectively attached form dioxolane, azetidine, piperidine, piperazine, oxopiperazine, oxopiperidine, tetrahydrofuran, tetrahydroimidazole, tetrahydrothiazole, tetrahydrooxazole, tetrahydropyran, tetrahydropyrrole, azapentyl ring, morpholinyl, thiomorpholinyl, 7-membered oxazacyclo or 7-membered oxazacyclospiro, each said ring system is independently optionally substituted or unsubstituted with one or more substituents selected from D, —F; —Cl; —Br; —I; —OH; oxo; =O; —SH; —CN; —NO₂; —N₃; methyl; ethyl; propyl; isopropyl; methoxy; ethoxy; propoxy; isopropoxy; C₂₋₄alkenyl; C₂₋₄alkynyl; C₁₋₃alkyl substituted with halogen; cyclopropyl; cyclobutyl; cyclopentyl; cyclohexyl; piperazinyl; piperazinyl substituted with 1, 2 or 3 substituents selected from F, Cl, Br, I, —OH, —CH₃, or 3-6 membered heterocyclyloxy; 3-6 membered heterocyclylthio; C₅₋₈ aryl, C₅₋₈ aryloxy; C₅₋₈ arylthio; 5-8 membered heteroaryl ring; 5-8 membered heteroaryloxy; 5-8 membered heterocyclylthio; —S(O)H; —S(O)CH₃; -methyl-S(O)H; -methyl-S(O)CH₃; -ethyl-S(O)H; -ethyl-S(O)CH₃; -propyl-S(O)H; -propyl-S(O)CH₃; -isopropyl-S(O)H; -isopropyl-S(O)CH₃; -methyl-OH; -methyl-OCH₃; -ethyl-OH; -ethyl-OCH₃; -propyl-OH; -propyl-OCH₃; -isopropyl-OH; -isopropyl-OCH₃; —C(O)OH; —C(O)OCH₃; -methyl-C(O)OH; -methyl-C(O)OCH₃; -ethyl-C(O)OH; -ethyl-C(O)OCH₃; -propyl-C(O)OH; -propyl-C(O)OCH₃; -isopropyl-C(O)OH; -isopropyl-C(O)OCH₃; —C(O)H; —C(O)CH₃; -methyl-C(O)H; -methyl-C(O)CH₃; -ethyl-C(O)H; -ethyl-C(O)CH₃; -propyl-C(O)H; -propyl-C(O)CH₃; -isopropyl-C(O)H; -isopropyl-C(O)CH₃; —O—C(O)H; —O—C(O)CH₃; -methyl-O—C(O)H; -methyl-O—C(O)CH₃; -ethyl-O—C(O)H; -ethyl-O—C(O)CH₃; -propyl-O—C(O)H; -propyl-O—C(O)CH₃; -isopropyl-O—C(O)H; -isopropyl-O—C(O)CH₃; —NH₂; —N(CH₃)₂; -methyl-NH₂; -methyl-N(CH₃)₂; -ethyl-NH₂; -ethyl-N(CH₃)₂; -propyl-NH₂; -propyl-N(CH₃)₂; -isopropyl-NH₂; -isopropyl-N(CH₃)₂; —C(O)NH₂; —C(O)N(CH₃)₂; -methyl-C(O)NH₂; -methylC(O)N(CH₃)₂; -ethyl-C(O)NH₂; -ethyl-C(O)N(CH₃)₂; -propyl-C(O)NH₂; -propyl-C(O)N(CH₃)₂; -isopropyl-C(O)NH₂; -isopropyl-C(O)N(CH₃)₂; —NH—C(O)H or —NH—C(O)OH.

In some embodiments, R₁ is selected from:

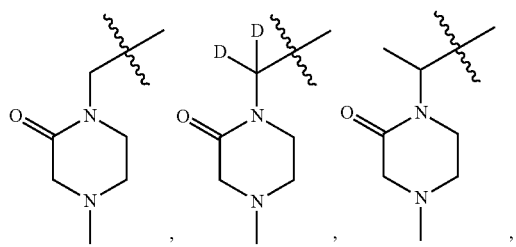

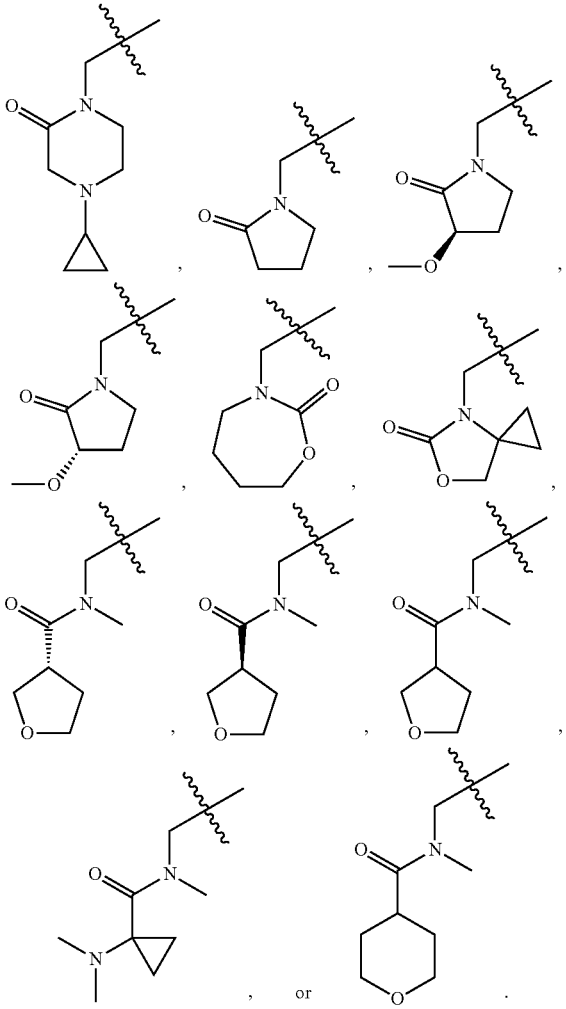

In some embodiments, R₁ is selected from:

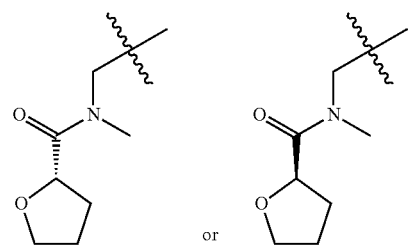

In some embodiments, R₂ and R₃ are respectively independently selected from H; D; —F; —Cl; —Br; —I; —OH; —SH; —CN; —NH₂; —NO₂; —N₃; —C₁₋₃alkyl; —C₁₋₃alkyl substituted with 1, 2 or 3 substituents selected from -D, —F, —Cl, —Br, —I, —OH, —CN, —NH₂, —NO₂, —COOH, —C₁₋₃alkyl or C₁₋₃alkoxy; —C₁₋₃alkoxy; C₁₋₃alkoxy substituted with 1, 2 or 3 substituents selected from -D, —F, —Cl, —Br, —I, —OH, —CN, —NH₂, —NO₂, —COOH, —C₁₋₃alkyl or C₁₋₃alkoxy; substituted or unsubstituted C₃₋₆cycloalkyl; substituted or unsubstituted C₃₋₆ heterocyclic; substituted or unsubstituted 3-6 membered heterocyclyloxy; substituted or unsubstituted 3-6 membered heterocyclylthio; —S(O)₁R₉; —C₁₋₃alkyl-S(O)₁

$R_9$; —O—$R_{10}$; —$C_{1-3}$alkyl-O—$R_{10}$; —C(O)O$R_{10}$; —$C_{1-3}$alkyl-C(O)O$R_{10}$; —C(O)$R_{11}$; —$C_{1-3}$alkyl-C(O)$R_{11}$; —O—C(O)$R_{11}$; —$C_{1-3}$alkyl-O—C(O)$R_{11}$; —N$R_{12}R_{13}$; —$C_{1-3}$alkylN$R_{12}R_{13}$; —C(O)N$R_{12}R_{13}$; —$C_{1-3}$alkyl-C(O)N$R_{12}R_{13}$; —N($R_{12}$)—C(O)$R_{11}$ or —N($R_{12}$)—C(O)O$R_{10}$;

In $R_2$ and $R_3$, each $R_9$ is independently optionally selected from H, D, —$C_{1-3}$alkyl $C_{1-3}$alkoxy, —$C_{2-4}$alkenyl, —$C_{3-6}$cycloalkyl, substituted or unsubstituted 3-6 membered heterocyclic, $C_{1-3}$haloalkyl, phenyl, p-methyl phenyl, amino, —NH—$C_{1-3}$alkyl, —N($C_{1-3}$alkyl)$_2$ or $C_{1-3}$alkylamide;

In $R_2$ and $R_3$, each $R_{10}$ is independently optionally selected from H, D, —$C_{1-3}$alkyl $C_{1-3}$alkoxy, —$C_{3-6}$cycloalkyl, —$C_{5-8}$aryl, $C_{1-3}$haloalkyl or $C_{1-3}$alkyl substituted with hydroxyl;

In $R_2$ and $R_3$, each $R_{11}$ is independently optionally selected from H, D, —$C_{1-3}$alkoxy, —$C_{3-6}$cycloalkyl, —$C_{3-6}$cycloalkoxy, $C_{1-3}$haloalkoxy, $C_{1-3}$alkyl substituted with hydroxyl, or $C_{1-3}$alkoxy substituted with hydroxyl;

In $R_2$ and $R_3$, each $R_{12}$ and $R_{13}$ is respectively independently optionally selected from H, D, —$C_{1-3}$alkyl $C_{1-3}$alkoxy, —$C_{1-3}$alkoxy —$C_{3-6}$cycloalkyl —$C_{2-4}$alkenyl, —$C_{2-4}$alkynyl, —$C_{3-6}$cycloalkyl, substituted or unsubstituted $C_{5-8}$ aryl, substituted or unsubstituted 5-8 membered heteroaryl or $C_{1-3}$alkanoyl;

t is 0, 1 or 2.

In some embodiments, $R_2$ and $R_3$ are respectively independently selected from H; D; —F; —Cl; —Br; —I; —OH; —SH; —CN; —NO$_2$; —N$_3$; methyl; ethyl; propyl; isopropyl; —$C_{1-3}$alkyl substituted with 1, 2 or 3 substituents selected from -D, —F, —Cl, —Br, —I, —OH, —CN, —NH$_2$, —NO$_2$, —COOH, —$C_{1-3}$alkyl or $C_{1-3}$alkoxy; methoxy; ethoxy; propoxy; isopropoxy; $C_{1-3}$alkoxy substituted with 1, 2 or 3 substituents selected from -D, —F, —Cl, —Br, —I, —OH, —CN, —NH$_2$, —NO$_2$, —COOH, —$C_{1-3}$alkyl or $C_{1-3}$alkoxy; substituted or unsubstituted $C_{3-6}$cycloalkyl; substituted or unsubstituted $C_{3-6}$ heterocyclic; substituted or unsubstituted 3-6 membered heterocyclyloxy; substituted or unsubstituted 3-6 membered heterocyclylthio; —S(O)$_t$$R_9$; —$C_{1-3}$alkyl-S(O)$_t$$R_9$; O—$R_{10}$; —$C_{1-3}$alkyl-O—$R_{10}$; —C(O)O$R_{10}$; —$C_{1-3}$alkyl-C(O)O$R_{10}$; —C(O)$R_{11}$; —$C_{1-3}$alkyl-C(O)$R_{11}$; —O—C(O)$R_{11}$; —$C_{1-3}$alkyl-O—C(O)$R_{11}$; —N$R_{12}R_{13}$; —$C_{1-3}$alkyl-N$R_{12}R_{13}$; —C(O)N$R_{12}R_{13}$; —$C_{1-3}$alkyl-C(O)N$R_{12}R_{13}$; —N($R_{12}$)—C(O)$R_{11}$ or —N($R_{12}$)—C(O)O$R_{10}$;

In $R_2$ and $R_3$, each $R_9$ is independently optionally selected from H, D, methyl, ethyl, propyl, isopropyl, —$C_{1-3}$alkyl $C_{1-3}$alkoxy, —$C_{2-4}$alkenyl, cyclopropyl, cyclobutyl, cyclopentyl, cyclohexyl, substituted or unsubstituted 3-6 membered heterocyclic, $C_{1-3}$haloalkyl, phenyl, p-methyl phenyl, amino, —NH—$C_{1-3}$alkyl, —N($C_{1-3}$alkyl)$_2$ or $C_{1-3}$alkylamide;

In $R_2$ and $R_3$, each $R_{10}$ is independently optionally selected from H, D, methyl, ethyl, propyl, isopropyl, —$C_{1-3}$alkyl $C_{1-3}$alkoxy, cyclopropyl, cyclobutyl, cyclopentyl, cyclohexyl, —$C_{5-8}$aryl, $C_{1-3}$haloalkyl or $C_{1-3}$alkyl substituted with hydroxyl;

In $R_2$ and $R_3$, each $R_{11}$ is independently optionally selected from H, D, methyl, ethyl, propyl, isopropyl, methoxy, ethoxy, propoxy, isopropoxy, cyclopropyl, cyclobutyl, cyclopentyl, cyclohexyl, —$C_{3-6}$cycloalkoxy, $C_{1-3}$haloalkyl, $C_{1-3}$haloalkoxy, $C_{1-3}$alkyl substituted with hydroxyl, or $C_{1-3}$alkoxy substituted with hydroxyl;

In $R_2$ and $R_3$, each $R_{12}$ and $R_{13}$ is respectively independently optionally selected from H, D, methyl, ethyl, propyl, isopropyl, —$C_{1-3}$alkyl $C_{1-3}$alkoxy, —$C_{1-3}$alkoxy $C_{1-3}$alkyl, —$C_{3-6}$cycloalkyl $C_{1-3}$alkyl, —$C_{2-4}$alkenyl, —$C_{2-4}$alkynyl, cyclopropyl, cyclobutyl, cyclopentyl, cyclohexyl, substituted or unsubstituted $C_{5-8}$ aryl, substituted or unsubstituted 5-8 membered heteroaryl or $C_{1-3}$alkanoyl;

t is 0 or 1.

In some embodiments, $R_2$ and $R_3$ are respectively independently selected from H; D; —F; —Cl; —Br; —I; —OH; —SH; —CN; —NO$_2$; —N$_3$; methyl; ethyl; propyl; isopropyl; —$C_{1-3}$alkyl substituted with 1, 2 or 3 substituents selected from -D, —F, —Cl, —Br, —I, —OH, —CN, —NH$_2$, —NO$_2$, —COOH, —$C_{1-3}$alkyl or $C_{1-3}$alkoxy; methoxy, ethoxy, propoxy, isopropoxy; $C_{1-3}$alkoxy substituted with 1, 2 or 3 substituents selected from -D, —F, —Cl, —Br, —I, —OH, —CN, —NH$_2$, —NO$_2$, —COOH, —$C_{1-3}$alkyl or $C_{1-3}$alkoxy; substituted or unsubstituted $C_{3-6}$cycloalkyl; substituted or unsubstituted 3-6 membered heterocyclic; substituted or unsubstituted 3-6 membered heterocyclyloxy; substituted or unsubstituted 3-6 membered heterocyclylthio; —S(O)H; —S(O)CH$_3$; -methyl-S(O)H; -methyl-S(O)CH$_3$; -ethyl-S(O)H; -ethyl-S(O)CH$_3$; -propyl-S(O)H; -propyl-S(O)CH$_3$; -isopropyl-S(O)H; -isopropyl-S(O)CH$_3$; -methyl-OH; -methyl-OCH$_3$; -ethyl-OH; -ethyl-OCH$_3$; -propyl-OH; -propyl-OCH$_3$; -isopropyl-OH; -isopropyl-OCH$_3$; —C(O)OH; —C(O)OCH$_3$; -methyl-C(O)OH; -methyl-C(O)OCH$_3$; -ethyl-C(O)OH; -ethyl-C(O)OCH$_3$; -propyl-C(O)OH; -propyl-C(O)OCH$_3$; -isopropyl-C(O)OH; -isopropyl-C(O)OCH$_3$; —C(O)H; —C(O)CH$_3$; -methyl-C(O)H; -methyl-C(O)CH$_3$; -ethyl-C(O)H; -ethyl-C(O)CH$_3$; -propyl-C(O)H; -propyl-C(O)CH$_3$; -isopropyl-C(O)H; -isopropyl-C(O)CH$_3$; —O—C(O)H; —O—C(O)CH$_3$; -methyl-O—C(O)H; -methyl-O—C(O)CH$_3$; -ethyl-O—C(O)H; -ethyl-O—C(O)CH$_3$; -propyl-O—C(O)H; -propyl-O—C(O)CH$_3$; -isopropyl-O—C(O)H; -isopropyl-O—C(O)CH$_3$; —NH$_2$; —N(CH$_3$)$_2$; -methyl-NH$_2$; -methyl-N(CH$_3$)$_2$; -ethyl-NH$_2$; -ethyl-N(CH$_3$)$_2$; -propyl-NH$_2$; -propyl-N(CH$_3$)$_2$; -isopropyl-NH$_2$; -isopropyl-N(CH$_3$)$_2$; —C(O)NH$_2$; —C(O)N(CH$_3$)$_2$; -methyl-C(O)NH$_2$; -methyl-C(O)N(CH$_3$)$_2$; -ethyl-C(O)NH$_2$; -ethyl-C(O)N(CH$_3$)$_2$; -propyl-C(O)NH$_2$; -propyl-C(O)N(CH$_3$)$_2$; -isopropyl-C(O)NH$_2$; -isopropyl-C(O)N(CH$_3$)$_2$; —NH—C(O)H or —NH—C(O)OH.

In some embodiments, $R_2$ and $R_3$ are respectively independently selected from H, D, —F, —Cl, —Br, —I, —OH, —SH, —CN, —NO$_2$, —N$_3$, methyl, ethyl, propyl, isopropyl, methoxy, ethoxy, propoxy or isopropoxy.

In some embodiments, $R_2$ and $R_3$ are respectively independently selected from H, D, —F or methyl.

In some embodiments, G at each occurrence is independently selected from —CR$_{G1}$R$_{G2}$—, —S—, —SO—, —SO$_2$— or O; m is 0, 1, 2, 3 or 4;

each R$_{G1}$ and R$_{G2}$ is independently selected from H, D, —$C_{1-3}$alkyl, —$C_{1-3}$alkyl substituted with 1, 2 or 3 substituents; —$C_{1-3}$alkoxy; —$C_{1-3}$alkoxy substituted with 1, 2 or 3 substituents; each said substituent is independently optionally selected from D, halogen, —OH, —CN, —NH$_2$, —NO$_2$, —COOH, —$C_{1-3}$alkyl or $C_{1-3}$alkoxy.

In some embodiments, G at each occurrence is independently selected from —CR$_{G1}$R$_{G2}$—, —S—, —SO—, —SO$_2$— or O; m is 0, 1, 2 or 3;

each R$_{G1}$ and R$_{G2}$ is independently selected from H; D; —$C_{1-3}$alkyl; —$C_{1-3}$alkyl substituted with 1, 2 or 3 substituents; —$C_{1-3}$alkoxy; or —$C_{1-3}$alkoxy substituted with 1, 2 or 3 substituents; each said substituent is independently optionally selected from D, —F, —Cl, —Br, —I, —OH, —CN, —NH$_2$, —NO$_2$, —COOH, methyl, ethyl, propyl, isopropyl, methoxy, ethoxy, propoxy or isopropoxy.

In some embodiments, G at each occurrence is independently selected from —CR$_{G1}$R$_{G2}$—, —S—, —SO—, —SO$_2$— or O; m is 0, 1, 2, or 3;

each $R_{G1}$ and $R_{G2}$ is independently selected from H; D; methyl; ethyl; propyl; isopropyl; —$C_{1-3}$alkyl substituted with 1, 2 or 3 substituents; methoxy, ethoxy, propoxy; isopropoxy; —$C_{1-3}$alkoxy substituted with 1, 2 or 3 substituents; each said substituent is independently optionally selected from D, —F, —Cl, —Br, —I, —OH, —CN, —$NH_2$, —$NO_2$, —COOH, methyl, ethyl, propyl, isopropyl, methoxy, ethoxy, propoxy or isopropoxy.

In some embodiments, G at each occurrence is independently selected from —$CH_2$—, —CHD-, —$CD_2$-, —NH—, —S—, —SO—, —$SO_2$— or O; m is 0, for 2.

In some embodiments, G at each occurrence is independently selected from —$CH_2$—, —CHD-, —$CD_2$-, —NH—, —S—, —SO—, —$SO_2$— or O; m is 0 or 1.

In some embodiments, G at each occurrence is independently selected from —NH— or O; m is 0 or 1.

In some embodiments, G at each occurrence is independently selected from —NH— or O; m is 1.

In some embodiments, G at each occurrence is independently selected from —NH—; m is 0 or 1.

In some embodiments, G at each occurrence is independently selected from —NH—; m is 1.

In some embodiments, m is 0.

In some embodiments, Q at each occurrence is independently selected from —$CR_4R_4'$—$(CR_4R_4')$q-;

Both $R_4$ and $R_4'$ are independently selected from H; D; —F; —Cl; —Br; —I; —OH; —$C_{1-6}$alkyl; $C_{1-6}$alkyl substituted with 1, 2 or 3 substituents; —$C_{1-6}$alkoxy; $C_{1-6}$alkoxy substituted with 1, 2 or 3 substituents; —$C_{3-8}$cycloalkyl; $C_{3-8}$cycloalkyl substituted with 1, 2 or 3 substituents; 3-8 membered heterocyclic; 3-8 membered heterocyclic substituted with 1, 2 or 3 substituents; each said substituent is independently optionally selected from D, halogen, —OH, —CN, —$NH_2$, —$NO_2$, —COOH, —$C_{1-3}$alkyl or $C_{1-3}$alkoxy; or $R_4$ and $R_4'$ together with the carbon to which they are both attached form —$C_{3-8}$ carbocyclic ring, -3-8 membered heterocyclic ring or —S-10 membered heteroaryl ring, each ring system is independently optionally substituted or unsubstituted with one or more substituents.

In some embodiments, Q is —$NR_4$—$(CR_4R_4')_q$—;

Both $R_4$ and $R_4'$ are independently selected from H; D; —F; —Cl; —Br; —I; —OH; —$C_{1-6}$alkyl; $C_{1-6}$alkyl substituted with 1, 2 or 3 substituents; —$C_{1-6}$alkoxy; $C_{1-6}$alkoxy substituted with 1, 2 or 3 substituents; —$C_{3-8}$cycloalkyl; $C_{3-8}$cycloalkyl substituted with 1, 2 or 3 substituents; 3-8 membered heterocyclic; 3-8 membered heterocyclic substituted with 1, 2 or 3 substituents; each said substituent is independently optionally selected from D, halogen, —OH, —CN, —$NH_2$, —$NO_2$, —COOH, —$C_{1-3}$alkyl or $C_{1-3}$alkoxy; or $R_4$ and $R_4'$ together with the carbon to which they are both attached form —$C_{3-8}$ carbocyclic ring, -3-8 membered heterocyclic ring or -5-10 membered heteroaryl ring, each ring system is independently optionally substituted or unsubstituted with one or more substituents.

In some embodiments, Q is —$CR_4R_4'$—$(CR_4R_4')_q$— or —$NR_4$—$(CR_4R_4')_q$—, and q is selected from 0, 1, 2, 3 or 4;
Both $R_4$ and $R_4'$ are independently selected from H; D; —F; —Cl; —Br; —I; —OH; —$C_{1-3}$alkyl; $C_{1-3}$alkyl substituted with 1, 2 or 3 substituents; —$C_{1-3}$alkoxy; $C_{1-3}$alkoxy substituted with 1, 2 or 3 substituents; —$C_{3-6}$cycloalkyl; $C_{3-6}$cycloalkyl substituted with 1, 2 or 3 substituents; 3-6 membered heterocyclic; 3-6 membered heterocyclic substituted with 1, 2 or 3 substituents; each said substituent is independently optionally selected from D, halogen, —OH, —CN, —$NH_2$, —$NO_2$, —COOH, —$C_{1-3}$alkyl or $C_{1-3}$alkoxy; or $R_4$ and $R_4'$ together with the carbon to which they are both attached form —$C_{3-6}$ carbocyclic ring, -3-6 membered heterocyclic ring or 5-8 membered heteroaryl ring, and each ring system is independently optionally substituted or unsubstituted with one or more substituents.

In some embodiments, Q is —$CR_4R_4'$—$(CR_4R_4')_q$—;
Both $R_4$ and $R_4'$ are independently selected from H; D; —F; —Cl; —Br; —I; —OH; —$C_{1-3}$alkyl; $C_{1-3}$alkyl substituted with 1, 2 or 3 substituents; —$C_{1-3}$alkoxy; $C_{1-3}$alkoxy substituted with 1, 2 or 3 substituents; —$C_{3-6}$cycloalkyl; $C_{3-6}$cycloalkyl substituted with 1, 2 or 3 substituents; 3-6 membered heterocyclic; 3-6 membered heterocyclic substituted with 1, 2 or 3 substituents; each said substituent is independently optionally selected from D, halogen, —OH, —CN, —$NH_2$, —$NO_2$, —COOH, —$C_{1-3}$alkyl or $C_{1-3}$alkoxy; or $R_4$ and $R_4'$ together with the carbon to which they are both attached form —$C_{3-6}$ carbocyclic ring, -3-6 membered heterocyclic ring or 5-8 membered heteroaryl ring, and each ring system is independently optionally substituted or unsubstituted with one or more substituents.

In some embodiments, Q is —$NR_4$—$(CR_4R_4')_q$—;
Both $R_4$ and $R_4'$ are independently selected from H; D; —F; —Cl; —Br; —I; —OH; —$C_{1-3}$alkyl; $C_{1-3}$alkyl substituted with 1, 2 or 3 substituents; —$C_{1-3}$alkoxy; $C_{1-3}$alkoxy substituted with 1, 2 or 3 substituents; —$C_{3-6}$cycloalkyl; $C_{3-6}$cycloalkyl substituted with 1, 2 or 3 substituents; 3-6 membered heterocyclic; 3-6 membered heterocyclic substituted with 1, 2 or 3 substituents; each said substituent is independently optionally selected from D, halogen, —OH, —CN, —$NH_2$, —$NO_2$, —COOH, —$C_{1-3}$alkyl or $C_{1-3}$alkoxy; or $R_4$ and $R_4'$ together with the carbon to which they are both attached form —$C_{3-6}$ carbocyclic ring, -3-6 membered heterocyclic ring or 5-8 membered heteroaryl ring, each ring system is independently optionally substituted or unsubstituted with one or more substituents.

In some embodiments, Q is —$CR_4R_4'$—$(CR_4R_4')_q$— or —$NR_4$—$(CR_4R_4')_q$—, and q is selected from 0, 1, 2, 3 or 4;
Both $R_4$ and $R_4'$ are independently selected from H; D; —F; —Cl; —Br; —I; —OH; —$C_{1-3}$alkyl; $C_{1-3}$alkyl substituted with 1, 2 or 3 substituents; —$C_{1-3}$alkoxy; $C_{1-3}$alkoxy substituted with 1, 2 or 3 substituents; —$C_{3-6}$cycloalkyl; $C_{3-6}$cycloalkyl substituted with 1, 2 or 3 substituents; 3-6 membered heterocyclic; 3-6 membered heterocyclic substituted with 1, 2 or 3 substituents; each said substituent is independently optionally selected from D, —F, —Cl, —Br, —I, —OH, —CN, —$NH_2$, —$NO_2$, —COOH, methyl, ethyl, propyl, isopropyl, methoxy, ethoxy, propoxy or isopropoxy; or $R_4$ and $R_4'$ together with the carbon to which they are both attached form —$C_{3-6}$ carbocyclic ring, -3-6 membered heterocyclic ring or 5-8 membered heteroaryl ring, said each heterocyclic ring and each heteroaryl ring independently optionally contains 1 or 2 heteroatoms selected from N, O or S, and each ring system is independently optionally substituted or unsubstituted with one or more substituents.

In some embodiments, Q is —$CR_4R_4'$—$(CR_4R_4')_q$—;
Both $R_4$ and are independently selected from H; D; —F; —Cl; —Br; —I; —OH; —$C_{1-3}$alkyl; $C_{1-3}$alkyl substituted with 1, 2 or 3 substituents; —$C_{1-3}$alkoxy; $C_{1-3}$alkoxy substituted with 1, 2 or 3 substituents; —$C_{3-6}$cycloalkyl; $C_{3-6}$cycloalkyl substituted with 1, 2 or 3 substituents; 3-6 membered heterocyclic; 3-6 membered heterocyclic substituted with 1, 2 or 3 substituents; each said substituent is independently optionally selected from D, —F, —Cl, —Br, —I, —OH, —CN, —NH$_2$, —NO$_2$, —COOH, methyl, ethyl, propyl, isopropyl, methoxy, ethoxy, propoxy or isopropoxy; or R$_4$ and R$_4$' together with the carbon to which they are both attached form —C$_{3-6}$ carbocyclic ring, -3-6 membered heterocyclic ring or —S-8 membered heteroaryl ring, said each heterocyclic ring and each heteroaryl ring independently optionally contains 1 or 2 heteroatoms selected from N, O or S, and each ring system is independently optionally substituted or unsubstituted with one or more substituents.

In some embodiments, Q is —NR$_4$—(CR$_4$R$_4$')$_q$—;

Both R$_4$ and are independently selected from H; D; —F; —Cl; —Br; —I; —OH; —C$_{1-3}$alkyl; C$_{1-3}$alkyl substituted with 1, 2 or 3 substituents; —C$_{1-3}$alkoxy; C$_{1-3}$alkoxy substituted with 1, 2 or 3 substituents; —C$_{3-6}$cycloalkyl; C$_{3-6}$cycloalkyl substituted with 1, 2 or 3 substituents; 3-6 membered heterocyclic; 3-6 membered heterocyclic substituted with 1, 2 or 3 substituents; each said substituent is independently optionally selected from D, —F, —Cl, —Br, —I, —OH, —CN, —NH$_2$, —NO$_2$, —COOH, methyl, ethyl, propyl, isopropyl, methoxy, ethoxy, propoxy or isopropoxy; or R$_4$ and R$_4$' together with the carbon to which they are both attached form —C$_{3-6}$carbocyclic ring, -3-6 membered heterocyclic ring or —S-8 membered heteroaryl ring, said each heterocyclic ring and each heteroaryl ring independently optionally contains 1 or 2 heteroatoms selected from N, O or S, and each ring system is independently optionally substituted or unsubstituted with one or more substituents.

In some embodiments, Q is —CR$_4$R$_4$'—(CR$_4$R$_4$')$_q$— or —NR$_4$—(CR$_4$R$_4$')$_q$—, and q is selected from 0, 1, 2, 3 or 4;

Both R$_4$ and R$_4$' are independently selected from H; D; —F; —Cl; —Br; —I; —OH; methyl; ethyl; propyl; isopropyl; —C$_{1-3}$alkyl substituted with 1, 2 or 3 substituents; methoxy; ethoxy; propoxy; isopropoxy; or —C$_{1-3}$alkoxy substituted with 1, 2 or 3 substituents; cyclopropyl; cyclobutyl; cyclopentyl; cyclohexyl; C$_{3-6}$ cycloalkyl substituted with 1, 2 or 3 substituents; 3-6 membered heterocyclic; or 3-6 membered heterocyclic substituted with 1, 2 or 3 substituents; each said substituent is independently optionally selected from D, —F, —Cl, —Br, —I, —OH, —CN, —NH$_2$, —NO$_2$, —COOH, methyl, ethyl, propyl, isopropyl, methoxy, ethoxy, propoxy or isopropoxy; or R$_4$ and R$_4$' together with the carbon to which they are both attached form 3 membered carbocyclic ring; 4 membered carbocyclic ring; 5 membered carbocyclic ring; 6 membered carbocyclic ring; 3 membered heterocyclic ring; 4 membered heterocyclic ring; 5 membered heterocyclic ring; 6 membered heterocyclic ring; 5 membered heteroaryl ring; 6 membered heteroaryl ring; 7 membered heteroaryl ring; 8 membered heteroaryl ring; said each heterocyclic ring and each heteroaryl ring independently optionally contains 1 or 2 heteroatoms selected from N, O or S, and said each carbocyclic ring, each heterocyclic ring, and heteroaryl ring is independently optionally substituted or unsubstituted with 1, 2 or 3 substituents.

In some embodiments, Q is —CR$_4$R$_4$'—(CR$_4$R$_4$')$_q$—;

Both R$_4$ and R$_4$' are independently selected from H; D; —F; —Cl; —Br; —I; —OH; methyl; ethyl; propyl; isopropyl; —C$_{1-3}$alkyl substituted with 1, 2 or 3 substituents; methoxy; ethoxy; propoxy; isopropoxy; —C$_{1-3}$alkoxy substituted with 1, 2 or 3 substituents; cyclopropyl; cyclobutyl; cyclopentyl; cyclohexyl; C$_{3-6}$cycloalkyl substituted with 1, 2 or 3 substituents; 3-6 membered heterocyclic; 3-6 membered heterocyclic substituted with 1, 2 or 3 substituents; each said substituent is independently optionally selected from D, —F, —Cl, —Br, —I, —OH, —CN, —NH$_2$, —NO$_2$, —COOH, methyl, ethyl, propyl, isopropyl, methoxy, propoxy or isopropoxy; or R$_4$ and R$_4$' together with the carbon to which they are both attached form 3 membered carbocyclic ring; 4 membered carbocyclic ring; 5 membered carbocyclic ring; 6 membered carbocyclic ring; 3 membered heterocyclic ring; 4 membered heterocyclic ring; 5 membered heterocyclic ring; 6 membered heterocyclic ring; 5 membered heteroaryl ring; 6 membered heteroaryl ring; 7 membered heteroaryl ring; 8 membered heteroaryl ring; said each heterocyclic ring and each heteroaryl ring independently optionally contains 1 or 2 heteroatoms selected from N, O or S, and said each carbocyclic ring, each heterocyclic ring, each heteroaryl ring is independently optionally substituted or unsubstituted with 1, 2 or 3 substituents.

In some embodiments, Q is —NR$_4$—(CR$_4$R$_4$')$_q$—;

Both R$_4$ and R$_4$' are independently selected from H; D; —F; —Cl; —Br; —I; —OH; methyl; ethyl; propyl; isopropyl; —C$_{1-3}$alkyl substituted with 1, 2 or 3 substituents; methoxy; ethoxy; propoxy; isopropoxy; —C$_{1-3}$alkoxy substituted with 1, 2 or 3 substituents; cyclopropyl; cyclobutyl; cyclopentyl; cyclohexyl; C$_{3-6}$cycloalkyl substituted with 1, 2 or 3 substituents; 3-6 membered heterocyclic; 3-6 membered heterocyclic substituted with 1, 2 or 3 substituents; each said substituent is independently optionally selected from D, —F, —Cl, —Br, —I, —OH, —CN, —NH$_2$, —NO$_2$, —COOH, methyl, ethyl, propyl, isopropyl, methoxy, ethoxy, propoxy or isopropoxy; or R$_4$ and R$_4$' together with the carbon to which they are both attached form 3 membered carbocyclic ring; 4 membered carbocyclic ring; 5 membered carbocyclic ring; 6 membered carbocyclic ring; 3 membered heterocyclic ring; 4 membered heterocyclic ring; 5 membered heterocyclic ring; 6 membered heterocyclic ring; 5 membered heteroaryl ring; 6 membered heteroaryl ring; 7 membered heteroaryl ring; 8 membered heteroaryl ring; said each heterocyclic ring and heteroaryl ring independently optionally contains 1 or 2 heteroatoms selected from N, O or S, and said each carbocyclic ring, each heterocyclic ring, and each heteroaryl ring is independently optionally substituted or unsubstituted with 1, 2 or 3 substituents.

In some embodiments, Both R$_5$ and R$_5$' are independently selected from H; D; —F; —Cl; —Br; —I; —OH; —C$_{1-3}$alkyl; —C$_{1-3}$alkyl substituted with 1, 2 or 3 substituents; —C$_{1-3}$alkoxy; —C$_{1-3}$alkoxy substituted with 1, 2 or 3 substituents; —C$_{3-6}$cycloalkyl; —C$_{3-6}$cycloalkyl substituted with 1, 2 or 3 substituents; 3-6 membered heterocyclic; 3-6 membered heterocyclic substituted with 1, 2 or 3 substituents; each said substituent is independently optionally selected from D, halogen, —OH, —CN, —NH$_2$, —NO$_2$, —COOH, —C$_{1-3}$alkyl or C$_{1-3}$alkoxy; or R$_5$ and R$_5$' together with the carbon to which they are both attached to form —C$_{3-6}$ carbocyclic ring, 3-6 membered heterocyclic ring, 5-8 membered heteroaryl ring, said each heterocyclic ring and each heteroaryl ring independently optionally contains 1 or 2 heteroatoms selected from N, O or S, and said ring system is independently optionally substituted or unsubstituted with one or more substituents; or R$_4$ and R$_5$ together with the atom to which they are respectively attached form 5-10 membered aromatic ring, —C$_{3-8}$ carbocyclic ring, 4-8 membered heterocyclic ring, each said heterocyclic independently optionally contains 1 or 2 substituents selected from N, O or S, and each said ring system is dependently optionally substituted or unsubstituted with one or more substituents.

In some embodiments, Both $R_5$ and $R_5'$ are independently selected from H; D; —F; —Cl; —Br; —I; —OH; methyl; ethyl; propyl; isopropyl; —$C_{1-3}$alkyl substituted with 1, 2 or 3 substituents; methoxy; ethoxy; propoxy; isopropoxy; —$C_{1-3}$alkoxy substituted with 1, 2 or 3 substituents; cyclopropyl; cyclobutyl; cyclopentyl; cyclohexyl; —$C_{3-6}$cycloalkyl substituted with 1, 2 or 3 substituents; 3 membered heterocyclic; 4 membered heterocyclic; 5 membered heterocyclic; 6 membered heterocyclic; 3-6 membered heterocyclic substituted with 1, 2 or 3 substituents; each said heterocyclic dependently optionally contains 1 or 2 substituents selected from N, O or S; each said substituent is independently optionally selected from D, —F, —Cl, —Br, —I, —OH, —CN, —NH$_2$, —NO$_2$, —COOH, methyl, ethyl, propyl, isopropyl, methoxy, ethoxy, propoxy or isopropoxy; or $R_5$ and $R_5'$ together with the carbon to which they are both attached to form 3 membered carbocyclic ring, 4 membered carbocyclic ring, 5 membered carbocyclic ring, 6 membered carbocyclic ring, 3 membered heterocyclic ring, 4 membered heterocyclic ring, 5 membered heterocyclic ring, 6 membered heterocyclic ring, 5 membered heteroaryl ring, 6 membered heteroaryl ring, 7 membered heteroaryl ring or 8 membered heteroaryl ring, said each heterocyclic ring and each heteroaryl ring independently optionally contains 1 or 2 heteroatoms selected from N, O or S, and said each ring system is independently optionally substituted or unsubstituted with 1, 2 or 3 substituents; or $R_4$ and $R_5$ together with the atom to which they are respectively attached form 5 membered aromatic ring, 6 membered aromatic ring, 7 membered aromatic ring, 8 membered aromatic ring, 9 membered aromatic ring, 10 membered aromatic ring, 4 membered carbocyclic ring, 5 membered carbocyclic ring, 6 membered carbocyclic ring, 7 membered carbocyclic ring, 8 membered carbocyclic ring, 4 membered heterocyclic ring, 5 membered heterocyclic ring, 6 membered heterocyclic ring, 7 membered heterocyclic ring, 8 membered heterocyclic ring, the each heterocyclic independently optionally contains 1 or 2 heteroatoms selected from N, O or S, and said each ring system is independently optionally substituted or unsubstituted with 1, 2 or 3 substituents.

In some embodiments, Both $R_5$ and $R_5'$ are independently selected from H; D; —F; —Cl; —Br; —I; —OH; methyl; ethyl; propyl; isopropyl; —$C_{1-3}$alkyl substituted with 1, 2 or 3 substituents; methoxy; ethoxy; propoxy; isopropoxy; —$C_{1-3}$alkoxy substituted with 1, 2 or 3 substituents; cyclopropyl; cyclobutyl; cyclopentyl; cyclohexyl; —$C_{3-6}$cycloalkyl substituted with 1, 2 or 3 substituents; 3 membered heterocyclic; 4 membered heterocyclic; 5 membered heterocyclic; 6 membered heterocyclic; 3-6 membered heterocyclic substituted with 1, 2 or 3 substituents; each said heterocyclic independently optionally contains 1 or 2 heteroatoms selected from N, O or S; each said substituent is independently optionally selected from D, —F, —Cl, —Br, —I, —OH, —CN, —NH$_2$, —NO$_2$, —COOH, methyl, ethyl, propyl, isopropyl, methoxy, ethoxy, propoxy or isopropoxy; or $R_5$ and $R_5'$ together with the carbon to which they are both attached form 3 membered carbocyclic ring, 4 membered carbocyclic ring, 5 membered carbocyclic ring, 6 membered carbocyclic ring, 3 membered heterocyclic ring, 4 membered heterocyclic ring, 5 membered heterocyclic ring, 6 membered heterocyclic ring, 5 membered heteroaryl ring, 6 membered heteroaryl ring, 7 membered heteroaryl ring, 8 membered heteroaryl ring; said each heterocyclic ring and each heteroaryl ring independently optionally contains 1 or 2 heteroatoms selected from N, O or S, and said each ring system is independently optionally substituted or unsubstituted with 1, 2 or 3 substituents selected from D, —F, —Cl, —Br, —I, —OH, oxo, =O, —NH$_2$, —CN, —COOH, —NO$_2$, methyl, ethyl, propyl, isopropyl, methoxy, ethoxy, propoxy or isopropoxy; or $R_4$ and $R_5$ together with the atom to which they are respectively attached form benzene, naphthalene, 3 membered carbocyclic ring, 4 membered carbocyclic ring, 5 membered carbocyclic ring, 6 membered carbocyclic ring, piperidine, piperazine, oxopiperazine, oxopiperidine, tetrahydrofuran, tetrahydroimidazole, tetrahydrothiazole, tetrahydrooxazole, tetrahydropyran, tetrahydropyrrole or azapentyl ring, and said each ring system is independently optionally substituted or unsubstituted with 1, 2 or 3 substituents selected from D, —F, —Cl, —Br, —I, —OH, NH$_2$, —CN, —COOH, —NO$_2$, methyl, ethyl, propyl, isopropyl, methoxy, ethoxy, propoxy or isopropoxy.

In some embodiments, $R_6$ at each occurrence is independently selected from H; D; —F; —Cl; —Br; —I; methyl; ethyl; propyl; isopropyl; —$C_{1-3}$alkyl substituted with 1, 2 or 3 substituents; methoxy; ethoxy; propoxy; isopropoxy; —$C_{1-3}$alkoxy substituted with 1, 2 or 3 substituents; -methyl-COO-methyl; -ethyl-COO-ethyl; -propyl-COO-propyl; -isopropyl-COO-isopropyl; cyclopropyl; cyclobutyl; cyclopentyl; cyclohexyl; —$C_{3-6}$ carbocyclic substituted with 1, 2 or 3 substituents; each said substituent is independently optionally selected from D, —F, —Cl, —Br, —I, —OH, —NH$_2$, —CN, —COOH, methyl, ethyl, propyl, isopropyl, methoxy, ethoxy, propoxy or isopropoxy; or Q and $R_6$ together with the carbon and W to which they are respectively attached form 4 membered heterocyclic ring, 5 membered heterocyclic ring, 6 membered heterocyclic ring or 7 membered heterocyclic ring, said heterocyclic ring is independently optionally substituted or unsubstituted with one or more substituents, said heterocyclic ring is independently optionally contains 1, 2 or 3 heteroatoms selected from N, O or S, said each substituent is independently optionally selected from D, —F, —Cl, —Br, —I, —OH, —CN, —NH$_2$, —NO$_2$, —COOH, —$C_{1-3}$alkyl or $C_{1-3}$alkoxy; or $R_4$ and $R_6$ together with the atom to which they are respectively attached form 5 membered monocyclic heterocyclic, 6 membered monocyclic heterocyclic, 7 membered monocyclic heterocyclic, 8 membered monocyclic heterocyclic, 5 membered spirocyclic heterocyclic, 6 membered spirocyclic heterocyclic, 7 membered spirocyclic heterocyclic, 8 membered spirocyclic heterocyclic, 9 membered spirocyclic heterocyclic, 10 membered spirocyclic heterocyclic, 5 membered fused heterocyclic, 6 membered fused heterocyclic, 7 membered fused heterocyclic, 8 membered fused heterocyclic, 9 membered fused heterocyclic, 10 membered fused heterocyclic, 5 membered bridged heterocyclic, 6 membered bridged heterocyclic, 7 membered bridged heterocyclic, 8 membered bridged heterocyclic, 9 membered bridged heterocyclic, 10 membered bridged heterocyclic, 5 membered heteroaryl ring, 6 membered heteroaryl ring, 7 membered heteroaryl ring, 8 membered heteroaryl ring, 9 membered heteroaryl ring or 10 membered heteroaryl ring, the each ring system is independently optionally contains 1, 2 or 3 heteroatoms which are selected from N, O or S, and each said ring system is independently optionally substituted or unsubstituted with 1, 2 or 3 substituents selected from D, —F, —Cl, —Br, —I, —OH, —NH$_2$, —CN, —COOH, oxo, =O, —$C_{1-3}$alkyl or —$C_{1-3}$alkoxy; or $R_5$ and $R_6$ together with the carbon and W to which they are respectively attached form 4 membered heterocyclic ring, 5 membered heterocyclic ring, 6 membered heterocyclic ring, 5 membered heteroaryl ring, 6 membered heteroaryl ring, 7 membered heteroaryl ring, 8 membered heteroaryl ring, the each ring system independently optionally contains 1, 2 or 3 heteroatoms selected from N, O or S, and each said ring system is independently optionally substituted or unsubstituted with 1, 2 or 3 substituents selected from D, —F, —Cl, —Br, —I, —OH, —NH₂, —CN, —COOH, oxo, =O, Methyl, ethyl, propyl, isopropyl, methoxy, ethoxy, propoxy or isopropoxy.

In some embodiments

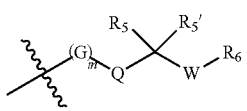

is selected from:

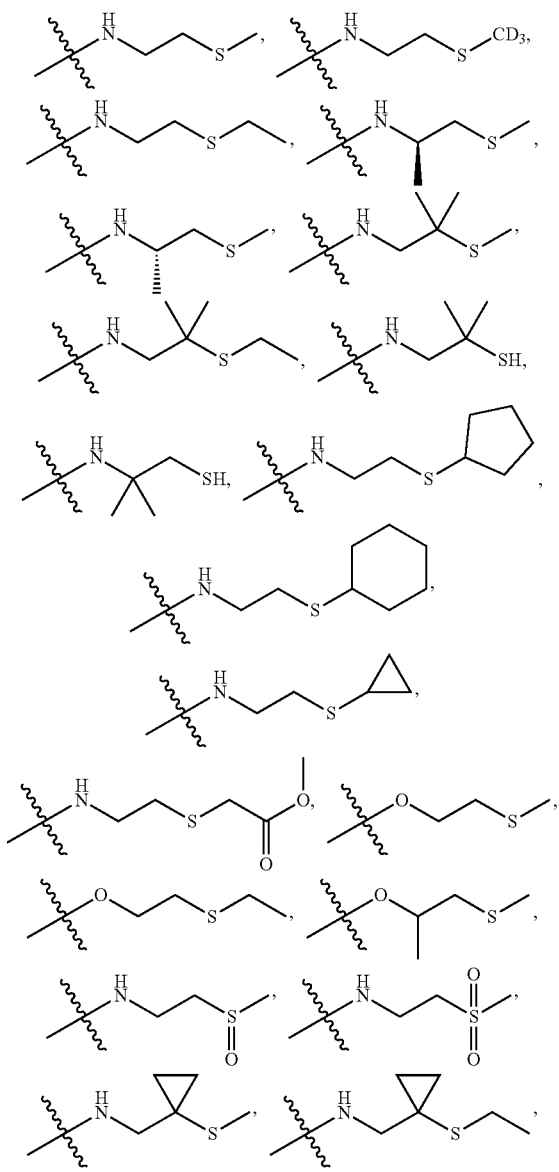

-continued

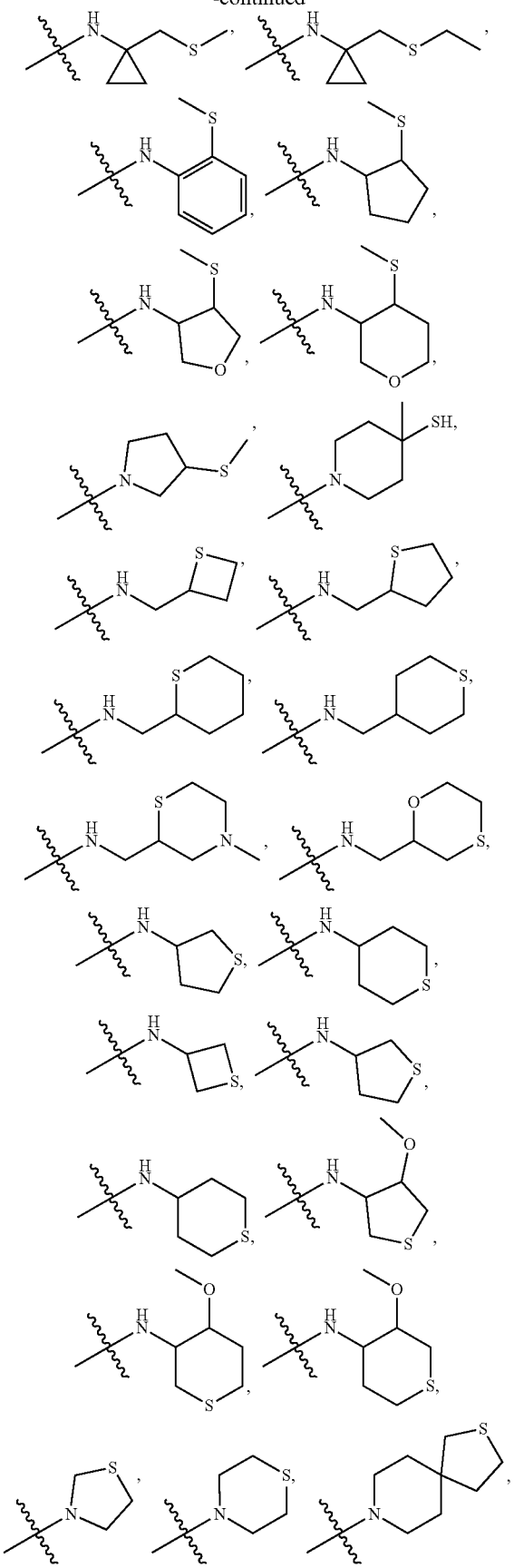

-continued is selected from:

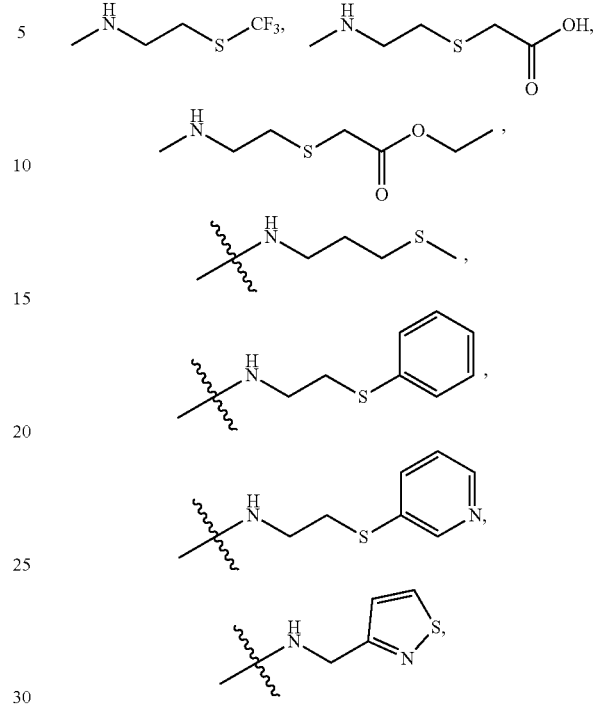

In some embodiments,

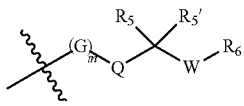

In some embodiments, the compound is selected from:

1. N-(5-cyano-4-((2-(methylthio)ethyl)amino)pyridin-2-yl)-7-formyl-6-((4-methyl-2-oxopiperazin-1-yl)methyl)-3,4-dihydro-1,8-naphthyridine-1(2H)-carboxamide;
2. N-(5-cyano-4-(2-(methylthio)ethoxy)pyridin-2-yl)-7-formyl-6-((4-methyl-2-oxopiperazin-1-yl)methyl)-3,4-dihydro-1,8-naphthyridine-1(2H)-carboxamide;
3. N-(5-cyano-4-thiomorpholinopyridin-2-yl)-7-formyl-6-((4-methyl-2-oxopiperazin-1-yl)methyl)-3,4-dihydro-1,8-naphthyridine-1(2H)-carboxamide;
4. (R)-N-(5-cyano-4-((1-(methylthio)propan-2-yl)amino)pyridin-2-yl)-7-formyl-6-((4-methyl-2-oxopiperazin-1-yl)methyl)-3,4-dihydro-1,8-naphthyridine-1(2H)-carboxamide;
5. N-(5-cyano-4-((tetrahydrothiophen-3-yl)amino)pyridin-2-yl)-7-formyl-6-((4-methyl-2-oxopiperazin-1-yl)methyl)-3,4-dihydro-1,8-naphthyridine-1(2H)-carboxamide;
6. (R)-N-(5-cyano-4-((2-(methylthio)ethyl)amino)pyridin-2-yl)-7-formyl-6-((3-methoxy-2-oxopyrrolidin-1-yl)methyl)-3,4-dihydro-1,8-naphthyridine-1(2H)-carboxamide;
7. N-(5-Cyano-4-(((R)-1-(methylthio)propan-2-yl)amino)pyridin-2-yl)-7-formyl-6-(((R)-3-methoxy-2-oxopyrrolidin-1-yl)methyl)-3,4-dihydro-1,8-naphthyridine-1(2H)-carboxamide;
8. (R)-N-(5-cyano-4-((1-(methylthio)propan-2-yl)amino)pyridin-2-yl)-7-formyl-6-((2-oxopyrrolidin-1-yl)methyl)-3,4-dihydro-1,8-naphthyridine-1(2H)-carboxamide;
9. N-(5-cyano-4-((2-methyl-2-(methylthio)propyl)amino)pyridin-2-yl)-7-formyl-6-((4-methyl-2-oxopiperazin-1-yl)methyl)-3,4-dihydro-1,8-naphthyridine-1(2H)-carboxamide;
10. N-(5-cyano-4-((2-(methylthio)phenyl)amino)pyridin-2-yl)-7-formyl-6-((4-methyl-2-oxopiperazin-1-yl)methyl)-3,4-dihydro-1,8-naphthyridine-1(2H)-carboxamide;
11. (S)-N-(5-cyano-4-((1-(methylthio)propan-2-yl)amino)pyridin-2-yl)-7-formyl-6-((4-methyl-2-oxopiperazin-1-yl)methyl)-3,4-dihydro-1,8-naphthyridine-1(2H)-carboxamide;
12. N-(5-cyano-4-((2-(cyclohexylthio)ethyl)amino)pyridin-2-yl)-7-formyl-6-((4-methyl-2-oxopiperazin-1-yl)methyl)-3,4-dihydro-1,8-naphthyridine-1(2H)-carboxamide;
13. (S)-N-(5-cyano-4-((2-(methylthio)ethyl)amino)pyridin-2-yl)-7-formyl-6-((3-methoxy-2-oxopyrrolidin-1-yl)methyl)-3,4-dihydro-1,8-naphthyridine-1(2H)-carboxamide;
14. N-(5-cyano-4-((2-(methylthio)ethyl)amino)pyridin-2-yl)-7-formyl-6-((5-oxo-6-oxa-4-azaspiro+2.4+heptan-4-yl)methyl)-3,4-dihydro-1,8-naphthyridine-1(2H)-carboxamide;
15. N-(5-cyano-4-((2-(methylthio)ethyl)amino)pyridin-2-yl)-6-((4-cyclopropyl-2-oxopiperazin-1-yl)methyl)-7-formyl-3,4-dihydro-1,8-naphthyridine-1(2H)-carboxamide;

16. N-(5-cyano-4-((2-(methylthio)ethyl)amino)pyridin-2-yl)-7-formyl-6-((2-oxo-1,3-oxazepan-3-yl)methyl)-3,4-dihydro-1,8-naphthyridine-1(2H)-carboxamide;
17. N-(5-cyano-4-((2-(ethylthio)-2-methylpropyl)amino)pyridin-2-yl)-7-formyl-6-((4-methyl-2-oxopiperazin-1-yl)methyl)-3,4-dihydro-1,8-naphthyridine-1(2H)-carboxamide;
18. N-(5-Cyano-4-((2-(methylthio)ethyl)amino)pyridin-2-yl)-4,4-difluoro-7-formyl-6-((4-methyl-2-oxopiperazin-1-yl)methyl)-3,4-dihydro-1,8-naphthyridine-1(2H)-carboxamide;
19. N-(5-Cyano-4-((2-((methyl-d3)thio)ethyl)amino)pyridin-2-yl)-7-formyl-6-((4-methyl-2-oxopiperazin-1-yl)methyl)-3,4-dihydro-1,8-naphthyridine-1(2H)-carboxamide;
20. N-(5-cyano-4-((tetrahydro-2H-thiopyran-4-yl)amino)pyridin-2-yl)-7-formyl-6-((4-methyl-2-oxopiperazin-1-yl)methyl)-3,4-dihydro-1,8-naphthyridine-1(2H)-carboxamide;
21. N-(5-Cyano-4-(thiazolidin-3-yppyridin-2-yl)-7-formyl-6-((4-methyl-2-oxopiperazin-1-yl)methyl)-3,4-dihydro-1,8-naphthyridine-1(2H)-carboxamide;
22. N-(5-cyano-4-((2-(methylthio)-propyl)amino)pyridin-2-yl)-7-formyl-6-((4-methyl-2-oxopiperazin-1-yl)methyl)-3,4-dihydro-1,8-naphthyridine-1(2H)-carboxamide;
23. N-(5-cyano-4-((2-(methylthio)ethyl)amino)pyridin-2-yl)-7-formyl-6-((2-oxopyrrolidin-1-yl)methyl)-3,4-dihydro-1,8-naphthyridine-1(2H)-carboxamide;
24. N-(5-cyano-4-((2-(methylthio)ethyl)amino)pyridin-2-yl)-6-((1-(dimethylamino)-N-methylcyclopropane-1-carboxamido)methyl)-7-formyl-3,4-dihydro-1,8-naphthyridine-1(2H)-carboxamide;
25. N-(5-cyano-4-((2-(methylthio)ethyl)amino)pyridin-2-yl)-7-formyl-6-((4-methyl-2-oxopiperazin-1-yl)methyl)-3,4-dihydro-1,8-naphthyridine-4,4-d2-1(2H)-carboxamide;
26. N-(5-cyano-4-((2-(cyclopropylthio)ethyl)amino)pyridin-2-yl)-7-formyl-6-((4-methyl-2-oxopiperazin-1-yl)methyl)-3,4-dihydro-1,8-naphthyridine-1(2H)-carboxamide;
27. N-(5-cyano-4-((2-(methylsulfinyl)ethyl)amino)pyridin-2-yl)-7-formyl-6-((4-methyl-2-oxopiperazin-1-yl)methyl)-3,4-dihydro-1,8-naphthyridine-1(2H)-carboxamide;
28. N-(5-cyano-4-((2-(cyclopentylthio)ethypamino)pyridin-2-yl)-7-formyl-6-((4-methyl-2-oxopiperazin-1-yl)methyl)-3,4-dihydro-1,8-naphthyridine-1(2H)-carboxamide;
29. Methyl-2-((2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl)thio)acetate;
30. N-(5-Cyano-4-((2-(methylthio)ethyl)amino)pyridin-2-yl)-7-formyl-4,4-dimethyl-6-((4-methyl-2-oxopiperazin-l-yl)methyl)-3,4-dihydro-1,8-naphthyridine-1(2H)-carboxamide;
31. N-(5-cyano-4-((2-(methylthio)ethyl)amino)pyridin-2-yl)-7-formyl-6-((4-methyl-2-oxopiperazin-1-yl)methyl-d2)-3,4-dihydro-1,8-naphthyridine-1(2H)-carboxamide;
32. N-(5-cyano-4-((2-(methylthio)ethyl)amino)pyridin-2-yl)-7-formyl-6-(1-(4-methyl-2-oxopiperazin-1-yl)ethyl)-3,4-dihydro-1,8-naphthyridine-1(2H)-carboxamide;
33. N-(5-cyano-4-(((tetrahydrothiophen-2-yl)methyl)amino)pyridin-2-yl)-7-formyl-6-((4-methyl-2-oxopiperazin-1-yl)methyl)-3,4-dihydro-1,8-naphthyridine-1(2H)-carboxamide;
34. N-(5-cyano-4-((thietan-2-yl-methyl)amino)pyridin-2-yl)-7-formyl-6-((4-methyl-2-oxopiperazin-1-yl)methyl)-3,4-dihydro-1,8-naphthyridine-1(2H)-carboxamide;
35. N-(5-cyano-4-(((tetrahydro-2H-thiopyran-2-yl)methyl)amino)pyridin-2-yl)-7-formyl-6-((4-methyl-2-oxopiperazin1-yl)methyl)-3,4-dihydro-1,8-naphthyridine-1(2H)-carboxamide;
36. N-(5-cyano-4-(1-thia-8-azaspiro+4.5+decan-8-yl)pyridin-2-yl)-7-formyl-6-((4-methyl-2-oxopiperazin-1-yl)methyl)-3,4-dihydro-1,8-naphthyridine-1(2H)-carboxamide;
37. N-(5-cyano-4-(((tetrahydro-2H-thiopyran-4-yl)methyl)amino)pyridin-2-yl)-7-formyl-6-((4-methyl-2-oxopiperazin-1-yl)methyl)-3,4-dihydro-1,8-naphthyridine-1(2H)-carboxamide;
38. N-(5-cyano-4-(((4-methylthiomorpholin-2-yl)methyl)amino)pyridin-2-yl)-7-formyl-6-((4-methyl-2-oxopiperazin-1-yl)methyl)-3,4-dihydro-1,8-naphthyridine-1(2H)-carboxamide;
39. N-(4-(((1,4-oxathian-2-yl)methyl)amino)-5-cyanopyridin-2-yl)-7-formyl-6-((4-methyl-2-oxopiperazin-1-yl)methyl)-3,4-dihydro-1,8-naphthyridine-1(2H)-carboxamide;
40. N-(5-cyano-4-((2-(methylthio)cyclopentyl)amino)pyridin-2-yl)-7-formyl-6-((4-methyl-2-oxopiperazin-1-yl)methyl)-3,4-dihydro-1,8-naphthyridine-1(2H)-carboxamide;
41. N-(5-cyano-4-((4-(methylthio)tetrahydrofuran-3-yl)amino)pyridin-2-yl)-7-formyl-6-((4-methyl-2-oxopiperazin-1-yl)methyl)-3,4-dihydro-1,8-naphthyridine-1(2H)-carboxamide;
42. N-(5-cyano-4-(3-(methylthio)pyrrolidin-1-yl)pyridin-2-yl)-7-formyl-6-((4-methyl-2-oxopiperazin-1-yl)methyl)-3,4-dihydro-1,8-naphthyridine-1(2H)-carboxamide;
43. N-(5-cyano-4-(((1-(methylthio)cyclopropyl)methyl)amino)pyridin-2-yl)-7-formyl-6-((4-methyl-2-oxopiperazin-1-yl)methyl)-3,4-dihydro-1,8-naphthyridine-1(2H)-carboxamide;
44. N-(5-cyano-4-((1-((methylthio)methyl)cyclopropyl)amino)pyridin-2-yl)-7-formyl-6-((4-methyl-2-oxopiperazin-1-yl)methyl)-3,4-dihydro-1,8-naphthyridine-1(2H)-carboxamide;
45. N-(5-cyano-4-((4-(methylthio)tetrahydro-2H-pyran-3-yl)amino)pyridin-2-yl)-7-formyl-6-((4-methyl-2-oxopiperazin-1-yl)methyl)-3,4-dihydro-1,8-naphthyridine-1(2H)-carboxamide;
46. N-(5-cyano-4-((3-(methylthio)tetrahydro-2H-pyran-4-yl)amino)pyridin-2-yl)-7-formyl-6-((4-methyl-2-oxopiperazin-1-yl)methyl)-3,4-dihydro-1,8-naphthyridine-1(2H)-carboxamide;
47. N-(5-cyano-4-(thietan-3-yl-amino)pyridin-2-yl)-7-formyl-6-((4-methyl-2-oxopiperazin-1-yOmethyl)-3,4-dihydro-1,8-naphthyridine-1(2H)-carboxamide;
48. N-(5-cyano-4-(((1-(ethylthio)cyclopropyl)methyl)amino)pyridin-2-yl)-7-formyl-6-((4-methyl-2-oxopiperazin-1-yl)methyl)-3,4-dihydro-1,8-naphthyridine-1(2H)-carboxamide;
49. N-(5-cyano-4-((1-((ethylthio)methyl)cyclopropyl)amino)pyridin-2-yl)-7-formyl-6-((4-methyl-2-oxopiperazin-1-yl)methyl)-3,4-dihydro-1,8-naphthyridine-1(2H)-carboxamide;
50. N-(5-Cyano-4-((4-((4methoxytetrahydrothiophen-3-yl)amino)pyridin-2-yl)-7-formyl-6-((4-methyl-2-oxopiperazin-1-yl)methyl)-3,4-dihydro-1,8-naphthyridine-1(2H)-carboxamide;
51. N-(5-Cyano-4-((4-methoxytetrahydro-2H-thiopyran-3-yl)amino)pyridin-2-yl)-7-formyl-6-((4-methyl-2-oxopiperazin-1-y1)methyl)-3,4-dihydro-1,8-naphthyridine-1(2H)-carboxamide;
52. N-(5-Cyano-44(3-((3-methoxytetrahydro-2H-thiopyran-4-yl)amino)pyridin-2-yl)-7-formyl-6-((4-methyl-2-oxopiperazin-1-yl)methyl)-3,4-dihydro-1,8-naphthyridine-1(2H)-carboxamide;
53. N-(5-cyano-4-(2-(ethylthio)ethoxy)pyridin-2-yl)-7-formyl-6-((4-methyl-2-oxopiperazin-1-yl)methyl)-3,4-dihydro-1,8-naphthyridine-1(2H)-carboxamide;
54. N-(5-cyano-4-((1-(methylthio)propan-2-yl)oxy)pyridin-2-yl)-7-formyl-6-((4-methyl-2-oxopiperazin-1-yl)methyl)-3,4-dihydro-1,8-naphthyridine-1(2H)-carboxamide;

55. N-(5-Cyano-4-((thiazol-5-yl-methyl)amino)pyridin-2-yl)-7-formyl-6-((4-methyl-2-oxopiperazin-1-yl)methyl)-3,4-dihydro-1,8-naphthyridine-1(2H)-carboxamide;
56. N-(5-Cyano-4-((thiazol-2-yl-methyl)amino)pyridin-2-yl)-7-formyl-6-((4-methyl-2-oxopiperazin-1-yl)methyl)-3,4-dihydro-1,8-naphthyridine-1(2H)-carboxamide;
57. N-(5-Cyano-4-((isothiazol-5-yl-methyl)amino)pyridin-2-yl)-7-formyl-6-((4-methyl-2-oxopiperazin-1-yl)methyl)-3,4-dihydro-1,8-naphthyridine-1(2H)-carboxamide;
58. N-(5-Cyano-4-(((5-methylthiophen-2-yl)methyl)amino)pyridin-2-yl)-7-formyl-6-((4-methyl-2-oxopiperazin-1-yl)methyl)-3,4-dihydro-1,8-naphthyridine-1(2H)-carboxamide;
59. N-(5-Cyano-4-((thiazol-4-ylmethyl)amino)pyridin-2-yl)-7-formyl-6-((4-methyl-2-oxopiperazin-1-yl)methyl)-3,4-dihydro-1,8-naphthyridine-1(2H)-carboxamide;
60. N-(5-cyano-4-((1-(thiazol-2-yl)ethyl)amino)pyridin-2-yl)-7-formyl-6-((4-methyl-2-oxopiperazin-1-yl)methyl)-3,4-dihydro-1,8-naphthyridine-1(2H)-carboxamide;
61. N-(5-cyano-4-((1-(5-methylthiophen-2-ypethyl)amino)pyridin-2-l1)-7-formyl-6-((4-methyl-2-oxopiperazin-1-yl)methyl)-3,4-dihydro-1,8-naphthyridine-1(2H)-carboxamide;
62. N-(5-cyano-4-((2-(ethylthio)ethyl)amino)pyridin-2-yl)-7-formyl-6-((4-methyl-2-oxopiperazin-1-yl)methyl)-3,4-dihydro-1,8-naphthyridine-1(2H)-carboxamide;
63. N-(5-cyano-4-((2-(methylsulfonyl)ethyl)amino)pyridin-2-yl)-7-formyl-6-((4-methyl-2-oxopiperazin-1-yl)methyl)-3,4-dihydro-1,8-naphthyridine-1(2H)-carboxamide;
64. N-(5-cyano-4-((2-(methylthio)ethyl)amino)pyridin-2-yl)-7-formyl-6-((N-methyltetrahydro-2H-pyran-4-carboxamido)methyl)-3,4-dihydro-1,8-naphthyridine-1(2H)-carboxamide;
65. (R)-N-(5-cyano-4-((2-(methylthio)ethyl)amino)pyridin-2-yl)-7-formyl-6-((N-methyltetrahydrofuran-2-carboxamido)methyl)-3,4-dihydro-1,8-naphthyridine-1(2H)-carboxamide;
66. (S)-N-(5-cyano-4-((2-(methylthio)ethyl)amino)pyridin-2-yl)-7-formyl-6-((N-methyltetrahydrofuran-2-carboxamido)methyl)-3,4-dihydro-1,8-naphthyridine-1(2H)-carboxamide;
67. N-(5-cyano-4-((2-(methylthio)ethyl)amino)pyridin-2-yl)-7-formyl-6-((N-methyltetrahydrofuran-3-carboxamido)methyl)-3,4-dihydro-1,8-naphthyridine-1(2H)-carboxamide;
68. N-(5-cyano-4-((1-mercapto-2-methylpropan-2-yl)amino)pyridin-2-yl)-7-formyl-6-((N-methyl-2-oxopiperazin-1-yl)methyl)-3,4-dihydro-1,8-naphthyridine-1(2H)-carboxamide;
69. N-(5-cyano-4-(4-mercapto-4-methylpiperidin-1-yl)pyridin-2-yl)-7-formyl-6-((methyl-2-oxopiperazin-1-yl)methyl)-3,4-dihydro-1,8-naphthyridine-1(2H)-carboxamide;
70. N-(5-cyano-4-((2-mercapto-2-methylpropyl)amino)pyridin-2-yl)-7-formyl-6-((4-methyl-2-oxopiperazin-1-yl)methyl)-3,4-dihydro-1,8-naphthyridine-1(2H)-carboxamide; or
71. N-(5-cyano-4-(3,6-dihydro-2H-thiopyran-4-yl)pyridin-2-yl)-7-formyl-6-((4-methyl-2-oxopiperazin-1-yl)methyl)-3,4-dihydro-1,8-naphthyridine-1(2H)-carboxamide.

In some embodiments, the compound is selected from:

72. N-(5-cyano-4-((2-((trifluoromethyl)thio)ethyl)amino)pyridin-2-yl)-7-formyl-6-((4-methyl-2-oxopiperazin-1-yl)methyl)-3,4-dihydro-1,8-naphthyridine-1(2H)-carboxamide;
73. 2-((2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl)thio)acetic acid;
74. N-(5-cyano-4-((3-(methylthio)propyl)amino)pyridin-2-yl)-7-formyl-6-((4-methyl-2-oxopiperazin-1-yl)methyl)-3,4-dihydro-1,8-naphthyridine-1(2H)-carboxamide;
75. N-(5-cyano-4-((1,1-dioxidotetrahydrothiophen-3-yl)amino)pyridin-2-yl)-7-formyl-6-((4-methyl-2-oxopiperazin-1-yl)methyl)-3,4-dihydro-1,8-naphthyridine-1(2H)-carboxamide;
76. N-(5-cyano-4-((2-(phenylthio)ethyl)amino)pyridin-2-yl)-7-formyl-6-((4-methyl-2-oxopiperazin-1-yl)methyl)-3,4-dihydro-1,8-naphthyridine-1(2H)-carboxamide;
77. N-(5-cyano-4-((2-(pyridin-3-yl-thio)ethyl)amino)pyridin-2-yl)-7-formyl-6-((4-methyl-2-oxopiperazin-1-yl)methyl)-3,4-dihydro-1,8-naphthyridine-1(2H)-carboxamide;
78. N-(5-cyano-4-((isothiazol-3-yl-methyl)amino)pyridin-2-yl)-7-formyl-6-((4-methyl-2-oxopiperazin-1-yl)methyl)-3,4-dihydro-1,8-naphthyridine-1(2H)-carboxamide;
79. N-(5-cyano-4-(((2R)-1-(methylsulfinyl)propan-2-yl)amino)pyridin-2-yl)-7-formyl-6-((4-methyl-2-oxopiperazin-1-yl)methyl)-3,4-dihydro-1,8-naphthyridine-1(2H)-carboxamide;
80. (R)-N-(5-cyano-4-((1-(methylthio)propan-2-yl)amino)pyridin-2-yl)-7-formyl-6-((2-oxo-1,3-oxazepan-3-yl)methyl)-3,4-dihydro-1,8-naphthyridine-1(2H)-carboxamide;
81. Ethyl-2-((2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl)thio)acetate;
82. N-(5-cyano-4-((1-(methylthio)propan-2-yl)amino)pyridin-2-yl)-7-formyl-6-((4-methyl-2-oxopiperazin-1-yl)methyl)-3,4-dihydro-1,8-naphthyridine-1(2H)-carboxamide; or
83. N-(5-cyano-4-(((2R)-1-(methylsulfonyl)propan-2-yl)amino)pyridin-2-yl)-7-formyl-6-((4-methyl-2-oxopiperazin-1-yl)methyl)-3,4-dihydro-1,8-naphthyridine-1(2H)-carboxamide.

In another aspect, the present invention provided a pharmaceutical composition comprising at least one compound of formula I or a pharmaceutically acceptable salt thereof, and at least one pharmaceutically acceptable excipient.

In another aspect, the present invention provided a pharmaceutical composition comprising at least one compound of formula I of the invention or a pharmaceutically acceptable salt thereof, and at least one pharmaceutically acceptable excipient.

In another aspect, the present invention provided the use of the compound of formula I or a pharmaceutically acceptable salt thereof, or pharmaceutical composition for the manufacture of a medicament. In some embodiments, the said medicament is used for the treatment, prevention or precaution of diseases or conditions mediated by FGFR4 activity.

In some embodiments, the diseases or conditions mediated by FGFR4 activity are cancer and/or cancerometastasis.

In some embodiments, the diseases mediated by FGFR4 activity are selected from one or more of the following diseases: liver cancer, head and neck cancer, esophageal cancer, stomach cancer, prostate cancer, ovarian cancer, lung cancer, breast cancer, colorectal cancer, rhabdomyoma and combinations thereof.

In another aspect, the present invention provides a method for the treatment, prevention or precaution of the diseases or conditions mediated by FGFR4 activity, said method comprises administering to the subject a therapeutically effective amount of compound of formula I or the pharmaceutically acceptable salt thereof, or the pharmaceutical composition thereof.

In some embodiments, the diseases or conditions mediated by FGFR4 activity are cancer and/or cancerometastasis.

In some embodiments, the diseases mediated by FGFR4 activity are selected from one or more following diseases: liver cancer, head and neck cancer, esophageal cancer, stomach cancer, prostate cancer, ovarian cancer, lung cancer, breast cancer, colorectal cancer, rhabdomyoma and combinations thereof.

In another aspect, the present invention provides the compound of formula I or the pharmaceutically acceptable salt thereof, or the pharmaceutical composition thereof for use in the treatment, prevention or precaution of the diseases or conditions mediated by FGFR4 activity.

In some embodiments, the diseases or conditions mediated by FGFR4 activity are cancer and/or cancerometastasis.

In some embodiments, the diseases mediated by FGFR4 activity are selected from one or more following diseases: liver cancer, head and neck cancer, esophageal cancer, stomach cancer, prostate cancer, ovarian cancer, lung cancer, breast cancer, colorectal cancer, rhabdomyoma and combinations thereof.

In the present invention, unless otherwise indicated, the term "halogen" refers to fluorine, chlorine, bromine and iodine. The preferred halogen group refers to fluorine, chlorine and bromine. The term "$C_{1-6}$alkyl substituted with halogen", "$C_{2-6}$alkenyl substituted with halogen", "$C_{2-6}$alkynyl substituted with halogen" and "$C_{1-6}$alkoxy substituted with halogen" refer to one or more (especially 1, 2 or 3) hydrogen atoms of them substituted by halogen atoms, especially fluorine or chlorine atoms. In some embodiments, $C_{1-6}$alkyl substituted with fluorine, $C_{2-6}$alkenyl substituted with fluorine, $C_{2-6}$alkynyl substituted with fluorine and $C_{1-6}$alkoxy substituted with fluorine are preferred, especially $C_{1-6}$alkyl substituted with fluorine, for example —$CF_3$, —$CHF_2$, —$CH_2F$, —$CH_2CH_2F$, —$CH_2CHF_2$, —$CH_2CF_3$; $C_{1-6}$alkyl substituted with fluorine, for example —$OCF_3$, —$OCHF_2$, —$OCH_2F$, —$OCH_2CH_2F$, —$OCH_2CHF_2$ or —$OCH_2CF_3$; especially —$CF_3$, —$OCF_3$ and —$OCHF_2$.

In the present invention, unless otherwise indicated, the term "alkyl" includes saturated monovalent hydrocarbon radicals having straight, branched or cyclic moieties. For example, alkyl radicals include methyl, ethyl, propyl, isopropyl, cyclopropyl, n-butyl, isobutyl, sec-butyl, t-butyl, cyclobutyl, n-pentyl, 3-(2-methyl) butyl, 2-pentyl, 2-methylbutyl, neopentyl, cyclopentyl, n-hexyl, 2-hexyl and 2-methylpentyl and cyclohexyl. Similarly, the $C_{1-8}$ alkyl in the present invention is defined as a group with 1, 2, 3, 4, 5, 6, 7 or 8 carbon atoms arranged in straight chain or branched chain.

The term "alkylene" means a difunctional group obtained by removal of hydrogen atom from an alkyl that is defined above. For example, methylene (i.e., —$CH_2$—), ethylene (i.e., —$CH_2$—$CH_2$— or —$CH(CH_3)$—) and propylene (i.e., —$CH_2$—$CH_2$— $CH_2$—, —$CH(-CH_2-CH_3)$— or —$CH_2$—$CH(CH_3)$—).

In the present invention, unless otherwise indicated, the term "alkoxy" refers to straight or branched chain alkoxy group containing specific number of carbon atoms. For example, "$C_{1-6}$alkoxy" refers to straight or branched chain alkoxy group containing at least one, at most six carbon atoms, including but not limited to, methoxy, ethoxy, propoxy, prop-2-oxy, butoxy, but-2-oxy, 2-methyl prop-1-oxy, 2-methyl prop-2-oxy, pentyloxy, hexyloxy, cyclopentyloxy or methylcyclopropoxy and so on.

Unless otherwise indicated, the term "alkenyl" refers to an alkyl as defined above consisting of at least two carbons and at least one carbon-carbon double bonds, "$C_{2-8}$alkenyl" refers to a straight or branched alkenyl containing 2-8 carbons. For example, ethyl, 1-propenyl, 2-propenyl, 1-, 2- or 3-butenyl, etc.

Unless otherwise indicated, the term "alkynyl" refers to alkyl as defined above consisting of at least two carbons and at least one carbon-carbon triple bonds, "$C_{2-8}$alkynyl" refers to a straight or branched alkenyl containing 2-8 carbons. For example, ethynyl, 1-propynyl, 2-propynyl, 1-, 2- or 3-butynyl, etc.

Unless otherwise indicated, the term "aryl" as used in the present invention by itself or as part of another substituent refers to a monocyclic or polycyclic aromatic hydrocarbon. Phenyl and naphthyl are preferred aryl. The most preferred aryl is phenyl.

Unless otherwise indicated, the term "heterocyclic" as used in the present invention by itself or as part of another substituent refers to a monocyclic or polycyclic non-aromatic family containing one or more heteroatoms, partially unsaturated or completely saturated ring system. Preferred heteroatoms include N, O and S, including N-oxides, sulfur oxides and dioxides. Preferably the ring is three to eight membered and is either fully saturated or has one or more degrees of unsaturation. Multiple degrees of substitution, preferably 1, 2 or 3, are included within the present definition.

Examples of such heterocyclic include but are not limited to azacyclobutyl, pyrrolidinyl, piperidinyl, piperazinyl, oxopiperazinyl, oxopiperidinyl, azacycloheptyl, tetrahydrofuranyl, dioxolanyl, tetrahydroimidazolyl, tetrahydrothiazolyl, tetrahydrooxazolyl, tetrahydropyranyl, morpholino, thiomorpholino, thiomorpholino sulfoxide, oxadiazole, nitroxanyl, pyridazinyl, indolyl, pyrimidinyl, pyrazinyl, isothiazolyl, diazanonaphthyl or indolazinyl.

"Heterocyclic" includes but is not limited to monocyclic heterocyclic and/or polycyclic heterocyclic.

Monocyclic heterocyclic includes but is not limited to pyrrolidinyl, tetrahydrofuranyl, piperidinyl, pyranyl, piperazinyl, morpholinyl, thiomorpholinyl or homopiperazinyl, etc., preferably pyrrolidinyl, tetrahydrofuranyl or pyranyl.

Polycyclic heterocyclic includes but is not limited to spirocyclic, fused ring and bridged-ring heterocyclic. "Spirocyclic heterocyclic" refers to polycyclic heterocyclic atom sharing a single atom (abbreviated spiroatom) between single rings, wherein one or more ring atom selected from heteroatoms of nitrogen, oxygen, S(O)r (wherein r is an integer of 0, 1, 2), and the remaining ring atoms are carbon. These can contain one or more double bonds, but none of the rings has a fully conjugated π-electron system. Spirocycloalkyl is classified as monospiroheterocyclyl, dispiroheterocyclyl or polyspiroheterocyclyl according to the number of spiroatoms shared between the rings. Spirocycloalkyl includes but is not limited to:

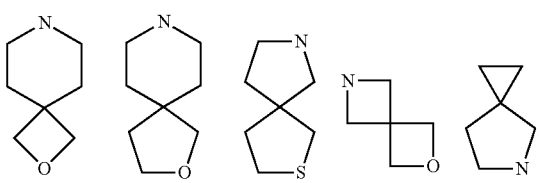

"Fused ring heterocyclic" refers to a polycyclic heterocyclic in which each ring in the system shares an adjacent pair of atoms with other rings in the system. One or more rings may contain one or more double bonds, but none of the ring has a fully conjugated π-electron system, wherein one or more ring atoms are selected from heteroatoms of nitrogen, oxygen, and S(O)r (wherein r is an integer of 0, 1, 2), and the remaining ring atoms are carbon. According to the number of constituent rings, it can be classified as bicyclic, tricyclic, tetracyclic or polycyclic fused heterocycloalkyl. The fused heterocyclic includes but is not limited to:

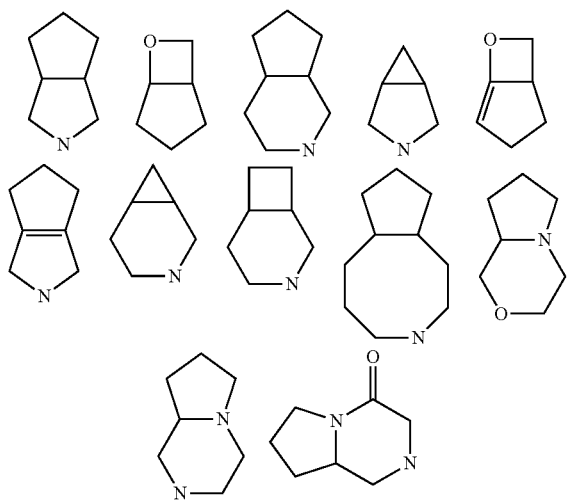

"Bridged heterocyclic group" refers to a polycyclic heterocyclic group in which any two rings share two atoms that are not directly connected. These may contain one or more double bonds, but none of the rings has a fully conjugated n-electron system. One or more ring atoms are selected from nitrogen, oxygen, and S(O)r (wherein r is an integer of 0, 1, 2) heteroatoms, and the remaining ring atoms are carbon. According to the number of constituent rings, it can be divided into bicyclic, tricyclic, tetracyclic or polycyclic bridged cycloalkyls. Bridged cycloalkyl includes but are not limited to:

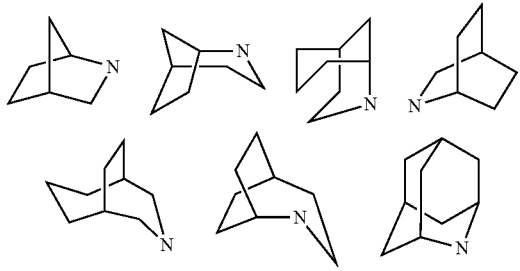

Unless otherwise indicated, otherwise the term "heteroaryl" used in the present invention by itself or as part of another substituent refers to an aromatic ring system containing carbon and at least one heteroatom. The heteroaryl can be monocyclic or polycyclic, substituted or unsubstituted. Monocyclic heteroaryl can have one to four heteroatoms in the ring, while polycyclic heteroaryl can have one to ten heteroatoms. The polycyclic heteroaryl ring may contain a fused spiroring or bridged ring, e.g., the cyclic heteroaryl is a polycyclic heteroaryl. The bicyclic heteroaryl ring may contain 8 to 12 member atoms. Monocyclic heteroaryl rings can contain 5 to 8 member atoms (number of carbon and heteroatoms). Examples of heteroaryl include but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzothiazolyl, benzothiadiazolyl, benzotriazolyl adenine, quinolinyl or isoquinolinyl.

Unless otherwise indicated, otherwise the term "cycloalkyl" used in the present invention by itself or as part of another substituent refers to monocyclic, bicyclic or polycyclic of non-aromatic family saturated or partially unsubstituted hydrocarbyl, and optionally includes alkylene linker through which cycloalkyl can be connected. Exemplary "cycloalkyl" group includes but is not limited to cyclopropyl, cyclobutyl, cyclopentyl, cyclohexyl and so on.

The term "oxo" refers to the group

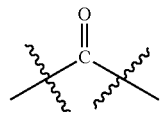 [SMILES: *C(*)=O]

which is formed by oxygen together with the attached carbon atom.

Whenever the term "alkyl" or "aryl" or any prefix roots thereof appears in the name of a substituent (for example, aralkyl or dialkylamino), unless otherwise specified, either by itself or as a part of another substituent should be construed as inclusion of the limitations of "alkyl" and "aryl" above mentioned. The designated number of carbon atoms (for example, $C_{1-6}$) shall independently refer to the number of carbon atoms in the alkyl moiety or the number of carbon atoms in the alkyl moiety of a larger substituent with an alkyl group as its prefix.

The compounds described herein, when specifically designated as R- or S-isomers by chemical names, should be understood as the main configuration as R-isomer or S-isomer, respectively. For example, in any of the embodiments described herein, such R- or S-designated isomers may be substantially free (as determined by chiral HPLC, less than 5%, less than 1%, or undetectable) of the other isomer of the chiral center. The R- or S-isomer can be prepared by the methods exemplified in this application, for example, by using a chiral auxiliary such as R- or S-tert-butylsulfinamide in the synthesis process. Other methods for preparing R- or S-isomers of the dominant configuration herein include, but are not limited to, chiral HPLC purification of mixtures of stereoisomers (such as racemic mixtures). General methods for separating stereoisomers (e.g., enantiomers and/or diastereomers) using HPLC are known in the art.

The compounds described herein may exist in an isotope-labeled or enriched form, which contains one or more atoms with atomic mass or mass number different from the most abundant atomic mass or mass number in nature. Isotopes can be radioactive or non-radioactive isotopes. Isotopes of atoms such as hydrogen, carbon, phosphorus, sulfur, fluorine, chlorine, and iodine include but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds containing other isotopes of these and/or other atoms are within the scope of the present invention. In some embodiments, one or more hydrogen atoms of any compound described herein can be replaced with deuterium to provide a corresponding labeled or enriched compound.

As used herein, the term "subject" (optionally referred to as "patient" in the present invention) refers to an animal that has become a subject of treatment, observation or experiment, preferably a mammal, and most preferably a human.

Unless otherwise specified, the term "ring system" (which may also be referred to as a "ring system") as used herein includes, but is not limited to, carbon rings, heterocycles, heteroaryl rings, etc., and may include only heterocycles and/or heteroaryl rings, and includes determining which rings are needed based on the context.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalene sulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula is shown without a definitive stereochemistry at certain positions. The present invention includes all stereoisomers of the compound of Formula (I) and pharmaceutically acceptable salts thereof. Further, mixtures of stereoisomers as well as isolated specific stereoisomers are also included. During the course of the synthetic procedures used to prepare such compounds or in using racemization or epimerization procedures known to those skilled in the art, the products of such procedures can be a mixture of stereoisomers.

When a tautomer of the compound of Formula (I) exists, unless otherwise stated, the present invention includes any possible tautomers and pharmaceutically acceptable salts thereof, and mixtures thereof.

When the compound of Formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from inorganic bases include aluminum, ammonium, calcium, copper (high and low value), trivalent iron, ferrous iron, lithium, magnesium, manganese (high and low value), potassium, sodium, zinc and the like. Salts of ammonium, calcium, magnesium, potassium, and sodium are particularly preferred. Non-toxic organic bases that can be derived into pharmaceutically acceptable salts include primary, secondary, and tertiary amines, as well as cyclic amines and substituent-containing amines, such as naturally occurring and synthetic substituent-containing amines Other pharmaceutically acceptable non-toxic organic bases capable of forming salts, Including ion exchange resins and arginine, betaine, caffeine, choline, N',N'-dibenzylethylenediamine, diethylamine, 2-diethylaminoethanol, 2-dimethylaminoethanol, ethanolamine, ethylenediamine, N-ethylmorphanol, N-ethylpiperidine, reduced glucosamine, glucosamine, histidine, haemamine, isopropylamine, lysine, methylglucosamine, morpholine, piperazine, piperidine, polyamine resins, procaine, purine, theobromine, triethylamine, trimethylamine, tripropylamine, aminobutriol etc.

When the compound of the present invention is basic, its corresponding salt can be conveniently prepared from pharmaceutically acceptable non-toxic acids, including inorganic and organic acids. Such acids include, e.g., acetic acid, benzenesulfonic acid, benzoic acid, camphorsulfonic acid, citric acid, ethanesulfonic acid, formic acid, fumaric acid, gluconic acid, glutamic acid, hydrobromic acid, hydrochloric acid, hydroxyethanesulfonic acid, lactic acid, maleic acid, malic acid, mandelic acid, methanesulfonic acid, mucic acid, nitric acid, pteric acid, pantothenic acid, phosphoric acid, succinic acid, sulfuric acid, tartaric acid, and p-toluenesulfonic acid. Preferably, citric acid, hydrobromic acid, formic acid, hydrochloric acid, maleic acid, phosphoric acid, sulfuric acid, and tartaric acid. Most preferably, formic acid and hydrochloric acid. Since the compounds are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound of formula I (or a pharmaceutically acceptable salt thereof) as an active ingredient, a pharmaceutically acceptable excipient and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds or prodrugs or metabolites or pharmaceutically acceptable salts thereof of this invention as the active ingredient can be admixed with a pharmaceutical carrier to form a pharmaceutical composition according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound of formula I or a pharmaceutically acceptable salt. The compounds of formula I or pharmaceutically acceptable salts thereof, can also be included in pharmaceutical compositions in combination with one or more other therapeutically active compounds.

The pharmaceutical carrier used in the present invention can be, for example, solid carrier, liquid carrier or gas carrier. Solid carrier includes lactose, terra alba, sucrose, talc, gelatin, agar, pectin, acacia, magnesium stearate, and stearic acid. Liquid carriers include sugar syrup, peanut oil, olive oil, and water. Gas carrier includes carbon dioxide and nitrogen. In preparing the compositions for oral dosage form, any convenient pharmaceutical media may be used. For example, water, glycols, oils, alcohols, flavoring agents, preservatives, coloring agents, and the like may be used to form oral liquid formulations such as suspensions, elixirs and solutions; while carriers such as starches, sugars, microcrystalline cellulose, diluents, granulating agents, lubricants, binders, disintegrating agents, and the like may be used to form oral solid formulations such as powders, capsules and tablets. Consider the ease of administration, tablets and capsules are preferred for oral formulations. Optionally, tablets may be coated by standard aqueous or nonaqueous techniques.

A tablet containing the compound or pharmaceutical composition of this invention may be prepared by compression or molding, optionally with one or more accessory ingredients or adjuvants. Compressed tablets may be prepared by compressing, in a suitable machine, the active ingredient in a free-flowing form such as powder or granules, mixed with a lubricant, inert diluent, surface active or dispersing agent. The powdered compound or pharmaceutical composition is wetted with an inert liquid diluent and then the molded tablets may be made by molding in a suitable machine. Each tablet preferably contains from about 0.05 mg to about 5 g of the active ingredient, each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of supplementary materials which may vary from about 0.05 to about 95 percent of the total composition. Unit dosage forms generally contain from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included, such as, hydroxypropylcellulose. Dispersions can also be prepared in glycerol, liquid polyethylene glycols, and mixtures thereof in oils. Further, a preservative can be included in the pharmaceutical composition of the present invention to prevent the detrimental growth of microorganisms.

The present invention provides the pharmaceutical compositions suitable for injection, including sterile aqueous solutions or dispersions. Furthermore, the pharmaceutical compositions can be prepared in the form of sterile powders for the extemporaneous preparation of sterile injectable solutions or dispersions. In any cases, the final injectable form must be sterile and must be easily flowable for ease of injection. The pharmaceutical compositions must be stable under the conditions of manufacture and storage. Thus, preferably should be preserved against the contaminating action of microorganisms such as bacteria and fungi. The carrier can be a solvent or dispersion medium, for example, water, ethanol, polyol (e.g., glycerol, propylene glycol and liquid polyethylene glycol), vegetable oils, and suitable mixtures thereof.

The pharmaceutical compositions provided by the present invention can be in a form suitable for topical use, such as, an aerosol, cream, ointment, lotion, dusting powder or other similar formulations. Further, the pharmaceutical compositions provided by the present invention can be in a form suitable for use in transdermal devices. These formulations may be prepared, via conventional processing methods, utilizing the compound of formula (I) of this invention or a pharmaceutically acceptable salt thereof. As an example, a cream or ointment is prepared by admixing hydrophilic material and water, together with about 5 wt % to about 10 wt % of the compound, to produce a cream or ointment having a desired consistency.

The pharmaceutical compositions provided by the present invention can be in a form suitable for rectal administration wherein the carrier is a solid. The preferred dosage form is a mixture forming a unit dose of suppository. Suitable ingredients include cocoa butter and other materials commonly used in the art. The suppositories may be conveniently formed by first admixing the pharmaceutical composition with the softened or melted excipients followed by chilling and shaping in molds.

In addition to the aforementioned carrier components, the above-mentioned pharmaceutical formulations may also include, as appropriate, one or more additional excipients components, such as diluents, buffers, flavoring agents, binders, surface-active agents, thickeners, lubricants, preservatives (including antioxidants) and the like. Furthermore, other adjuvants can also include penetration enhancers that regulate the isotonic pressure of the drug and blood. A compound of formula (I) or a pharmaceutical composition including a pharmaceutically acceptable salts thereof, may also be prepared in the form of powder or concentrated solution.

Generally, in order to treat the conditions or discomforts shown above, the dosage level of the drug is approximately 0.01 mg/kg to about 150 mg/kg of body weight per day, or 0.5 mg to 7 g per patient per day. The effective dosage level of the drug for disease and discomforts, such as inflammation, cancer, psoriasis, allergy/asthma, disease and discomforts of the immune system, disease and discomforts of the central nervous system (CNS), is 0.01 mg/kg to 50 mg/kg of body weight per day, or 0.5 mg to 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

EXAMPLES

The following intermediates and examples are provided to illustrate the present invention. Unless expressly stated otherwise, all parts and percentages are by weight, and all temperatures are in degrees Celsius. The following abbreviations are used in the examples:

| | |
|---|---|
| DCM | Dichloromethane |
| EtOAc | Ethyl acetate |
| EtOH | Ethanol |
| THF | Tetrahydrofuran |
| DMF | N, N-dimethylformamide |
| $CH_3CN$ | Acetonitrile |
| TFA | Trifluoroacetic acid |
| $MnO_2$ | Manganese dioxide |
| DPPF | 1,1'-bis(diphenylphosphine)ferrocene |
| DIEA/DIPEA | N, N-diisopropyl ethylamine |
| $Pd_2(dba)_3$ | Tri-dibenzyl acetone dipalladium |
| $Zn(CN)_2$ | zinc cyanide |
| NIS | Iodosuccinimide |
| Na | sodium |
| $Na_2SO_4$ | Sodium sulfate |
| NaCl | Sodium chloride |
| HATU | 2-(7-azobenzotriazole)-N,N,N',N'-tetramethylurea hexafluorophosphate |
| $Boc_2O$ | Di-tert butyl dicarbonate |

Preparation of Intermediate A1

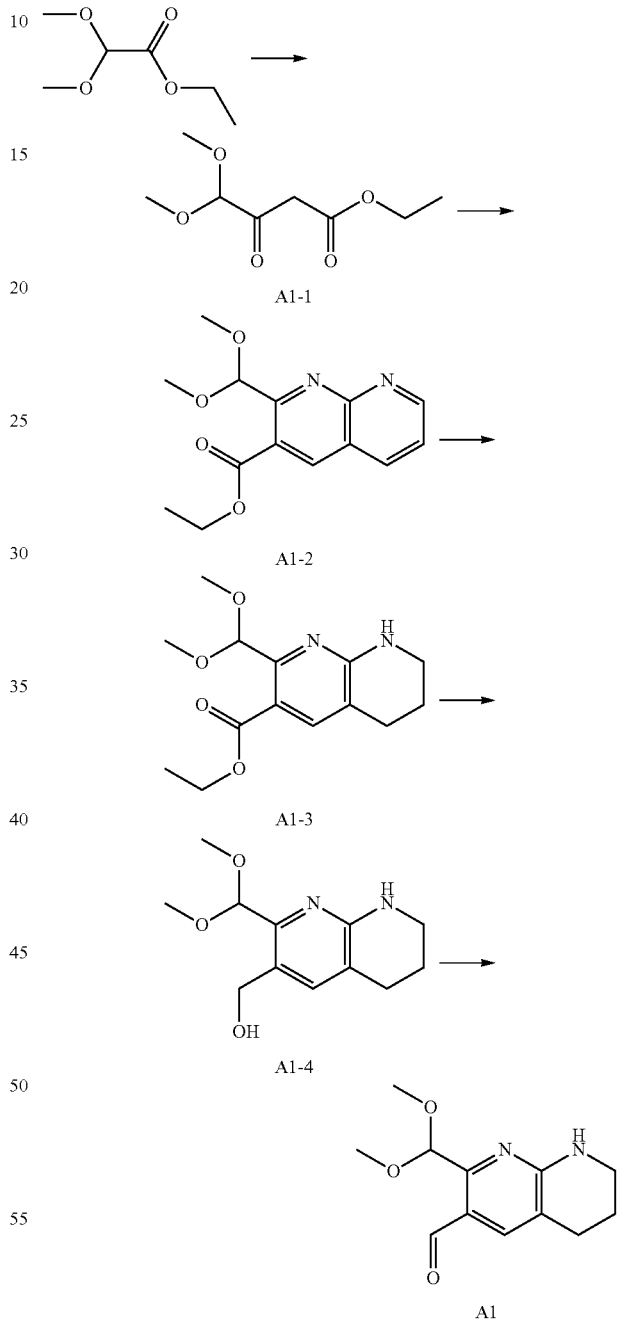

Ethyl dimethoxyacetate (147.59 g, 1.00 mol) was dissolved in EtOAc (150.23 g, 1.71 mol), and Na (33.42 g, 1.45 mol) was added at 60° C. The reaction mixture was refluxed and stirred overnight, cooled to room temperature, diluted with EtOAc (500 mL), and concentrated under reduced pressure. The residue was purified by a silica gel column to afford the compound A1-1 (135.47 g, 0.71 mol).

The compound A1-1 (83.64 g, 0.44 mol), 2-Amino-3-pyridine carboxaldehyde (45.11 g, 0.37 mol) and L-Proline (42.92 g, 0.37 mol) were mixed with anhydrous EtOH (400 mL). The reaction mixture was stirred overnight at 90° C., cooled to room temperature, and concentrated under reduced pressure. The concentrate was diluted with EtOAc (1 L), filtered and washed with EtOAc (200 mL), and the filtrate was concentrated under reduced pressure. The residue was purified by a silica gel column to afford compound A1-2 (102.05 g, 0.37 mol).

The compound A1-2 (102.05 g, 0.37 mol) was dissolved in EtOAc (800 mL), and palladium on carbon (6.49 g) was added. The reaction mixture was purged with hydrogen three times, and stirred overnight at room temperature. The resulting mixture was filtered, and the filtrate was concentrated under reduced pressure to afford the compound A1-3 (99.83 g, 0.36 mol).

The compound A1-3 (21.97 g, 78.37 mmol) was dissolved in THF (50 mL), and lithium borohydride (1 mol/L in THF, 200 mL, 0.20 mol) was added dropwise. The reaction mixture was stirred overnight at 65° C., cooled to 0° C., quenched with $H_2O$ (150 mL), and the THF was evaporated. EtOAc (500 mL) and $H_2O$ (100 mL) was added into the concentrate, and the liquids was separated. The organic phase was dried over anhydrous $Na_2SO_4$, filtered, and the filtrate was concentrated under reduced pressure to afford the compound A1-4 (19.58 g, 82.17 mmol). MS m/z (ESI): 239 (M+H)$^+$.

The compound A1-4 (9.88 g, 41.46 mmol) was dissolved in DCM (300 mL), and $MnO_2$ (73.38 g, 844.03 mmol) was added. The reaction mixture was stirred overnight at 40° C., then filtered and washed with DCM. The filtrate was concentrated under reduced pressure to afford compound A1 (8.91 g, 37.71 mmol). MS m/z (ESI): 237 (M+H)$^+$.

The following intermediates A2-A5 were synthesized with appropriate raw materials:

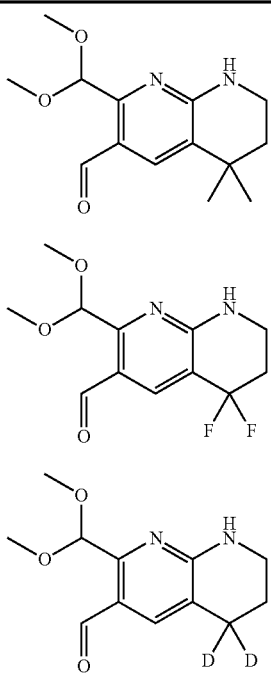

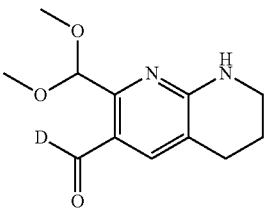 [SMILES: [2H]C(=O)c1cc2c(nc1C(OC)OC)NCCC2]

Preparation of Intermediate B1

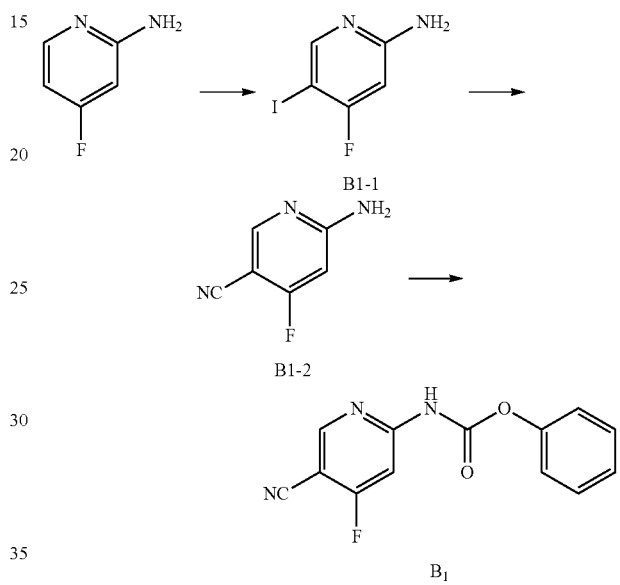

2-amino-4-fluoropyridine (6.44 g, 57.44 mmol), NIS (15.58 g, 69.25 mmol) and TFA (3.55 g, 31.13 mmol) were dissolved in acetonitrile (250 mL). The reaction mixture was stirred for 2 hrs at room temperature, and then the acetonitrile was evaporated. The concentrate was diluted with EtOAc (500 mL), washed with saturated sodium carbonate solution (300 mL×1), and washed with saturated NaCl aqueous solution (500 mL×1). The organic phase was dried with anhydrous $Na_2SO_4$ and filtered. The filtrate was concentrated under reduced pressure to obtain compound B1-1 (12.31 g, 51.72 mmol). MS m/z (ESI): 239 (M+H)$^+$.

The Compound B1-1 (12.31 g, 51.72 mmol), Zn(CN)2 (6.35 g, 54.08 mmol), Zn (1.01 g, 15.45 mmol), $Pd_2(dba)_3$ (5.04 g, 5.50 mmol) and DPPF (5.97 g, 10.77 mmol) were mixed with N,N-dimethylformamide (200 mL) under the protection of nitrogen. The reaction mixture was stirred for 2.5 hrs at 110° C., cooled to room temperature, diluted with EtOAc (500 mL), and washed with saturated NaCl aqueous solution (500 mL×3). The organic phase was dried over anhydrous $Na_2SO_4$, and concentrated under reduced pressure. The residue was purified by a silica gel column to afford the compound B1-2 (5.22 g, 38.07 mmol). MS m/z (ESI): 138 (M+H)$^+$.

The B1-2 (5.22 g, 38.07 mmol) and pyridine (15.52 g, 196.21 mmol) were dissolved in DCM (160 mL), and phenyl chloroformate (9.32 g, 59.53 mmol) was added. The reaction mixture was stirred for 1.5 hrs at room temperature, and then filtered to obtain the compound B1 as a solid. The filtrate was concentrated under reduced pressure, and the residue was purified by a silica gel column to afford the purified product. The purified product was combined with the filter cake to obtain the compound B1 (8.52 g, 33.12 mmol). MS m/z (ESI): 258 (M+H)+.

Preparation of Intermediate C1

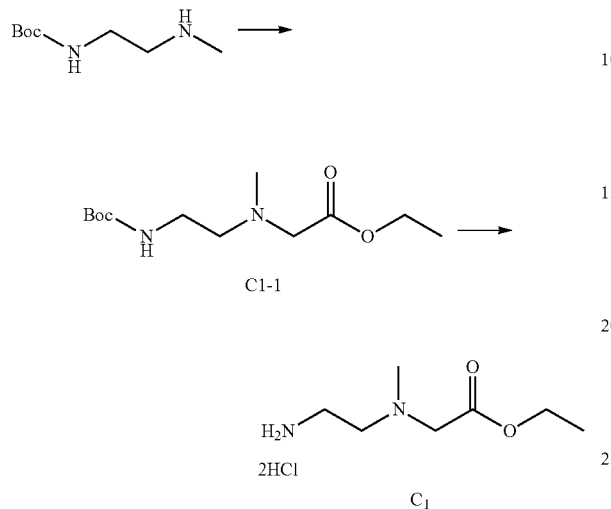

2-(methylamino)ethylcarbamic acid tert-butyl ester (69.54 g, 0.40 mol) and DIPEA (156.21 g, 1.21 mol) was dissolved in DCM (500 mL), and ethyl 2-bromoacetate (69.23 g, 0.41 mol) was added at 0-5° C. The reaction mixture was stirred for 6.5 hrs at room temperature, and concentrated under reduced pressure. The concentrate was diluted with EtOAc (1000 mL), stirred for 10 mins at room temperature, filtrated and washed with EtOAc (1000 mL). The filtrate was concentrated under reduced pressure. The residue was purified by a silica gel column to afford the compound C1-1 (106.41 g, 0.41 mol). MS m/z (ESI): 261 (M+H)+.

The compound C1-1 (3.35 g, 12.87 mmol) was dissolved in DCM (10 mL), and 1,4-dioxane solution of hydrochloric acid (4 mol/L, 20 mL, 80 mmol) was added dropwise. The reaction mixture was stirred for 2 hrs at room temperature, and concentrated under reduced pressure to afford the compound C1 (2.93 g, 12.57 mmol). MS m/z (ESI): 161 (M+H)+.

The following intermediates C2-C3 were synthesized with appropriate raw materials:

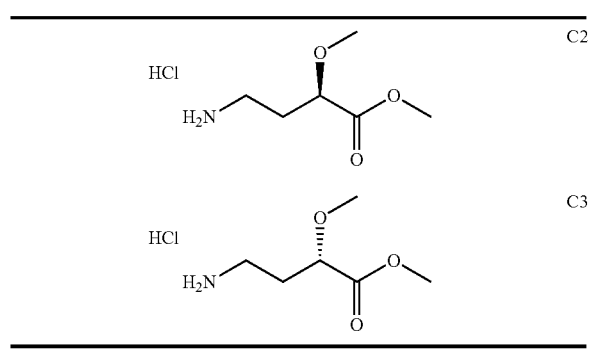

Preparation of Intermediate D1

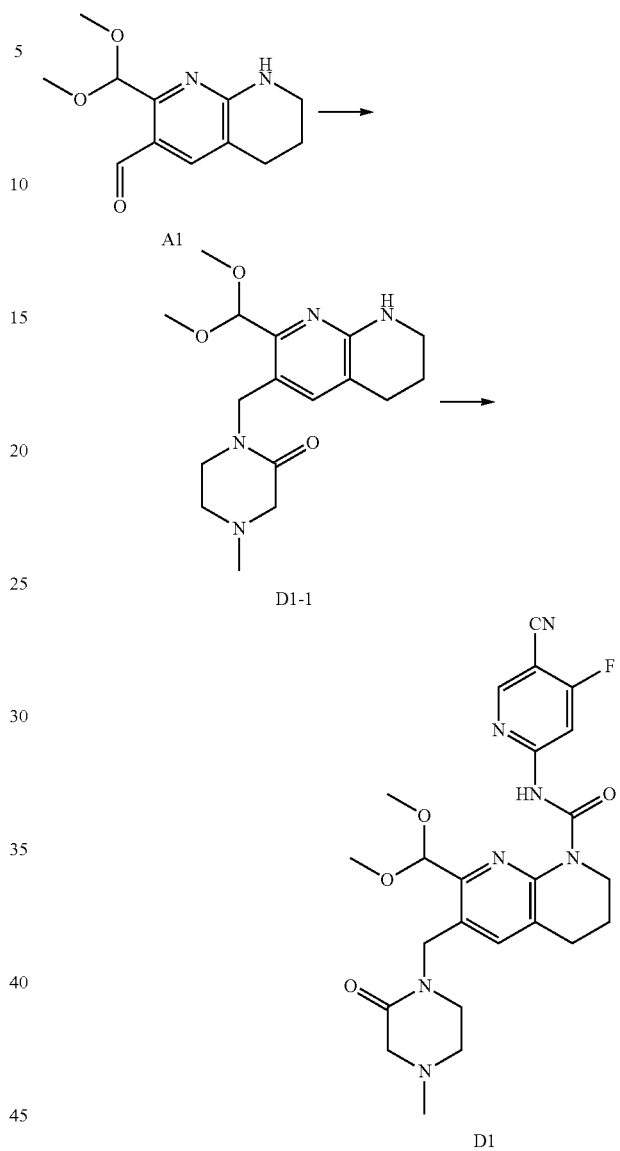

The intermediate C1 (11.49 g, 48.63 mmol) was dissolved in DCM (1000 mL), and triethylamine (16.22 g, 160.29 mmol) was added dropwise. The resulting solution was stirred for 15 mins at room temperature, then Intermediate A1 (8.91 g, 38.22 mmol) and sodium triacetoxyborohydride (23.76 g, 112.11 mmol) were added successively. The reaction mixture was stirred at room temperature overnight, quenched with H2O (200 mL), and the liquids was separated. The organic phase was washed with saturated NaCl aqueous solution (200 mL×1). The organic phase was collected and concentrated under reduced pressure. The residue was purified by a silica gel column to afford the compound D1-1 (6.24 g, 18.66 mmol). MS m/z (ESI): 335 (M+H)+.

The compound D1-1 (2.48 g, 7.42 mmol), intermediate B1 (2.98 g, 11.59 mmol) and DIEA (5.21 g, 40.31 mmol) were mixed with acetonitrile (50 mL). The reaction mixture was stirred for 2.5 hrs at 65° C., cooled to room temperature, and concentrated under reduced pressure. The residue was purified by a silica gel column to afford a light yellow solid compound D1 (1.38 g, 2.77 mmol). Ms m/z (ESI): 498 (M+H)+.

The following intermediates D2-D9 were synthesized according to the synthesis method of intermediate D1:
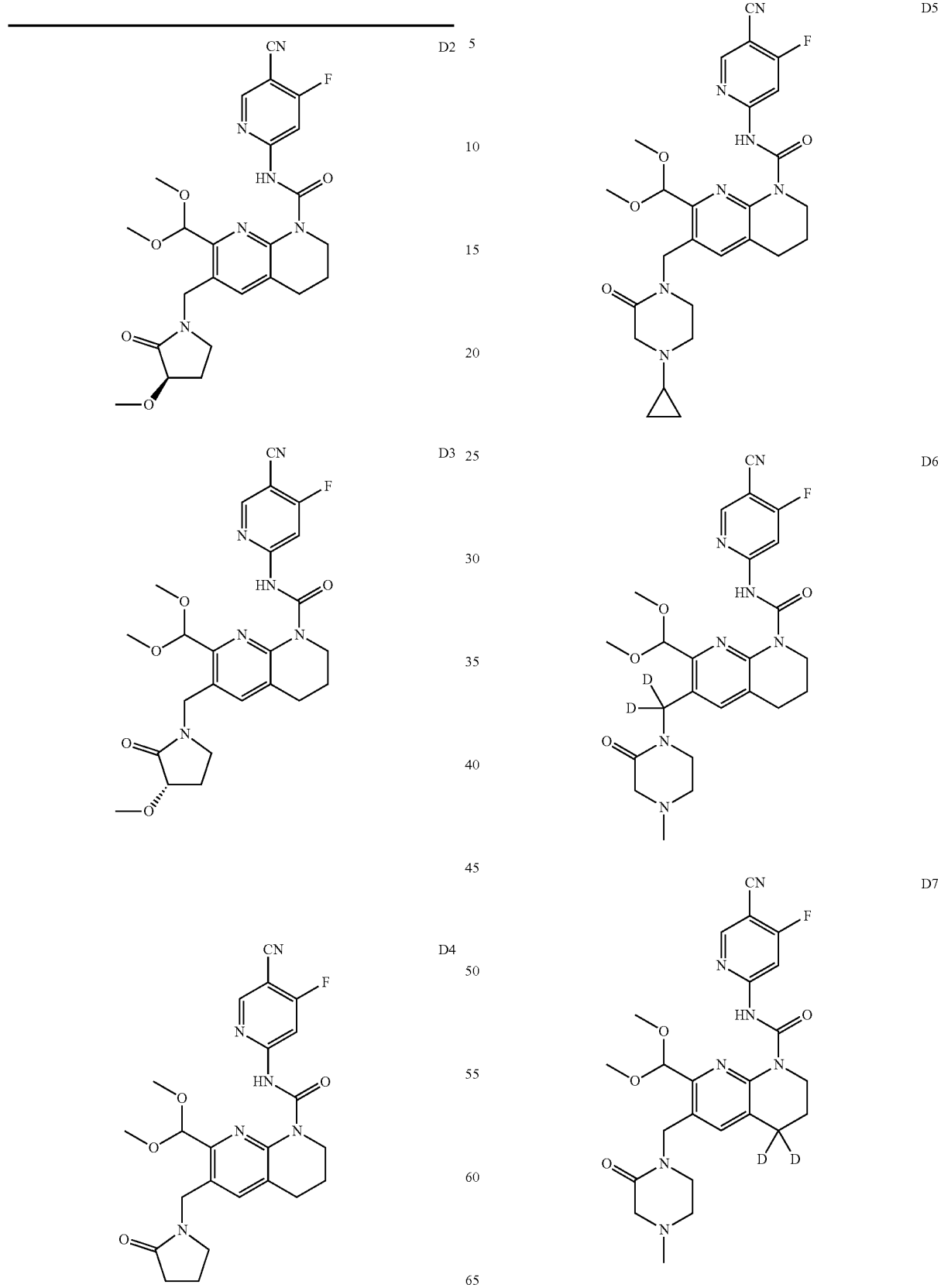

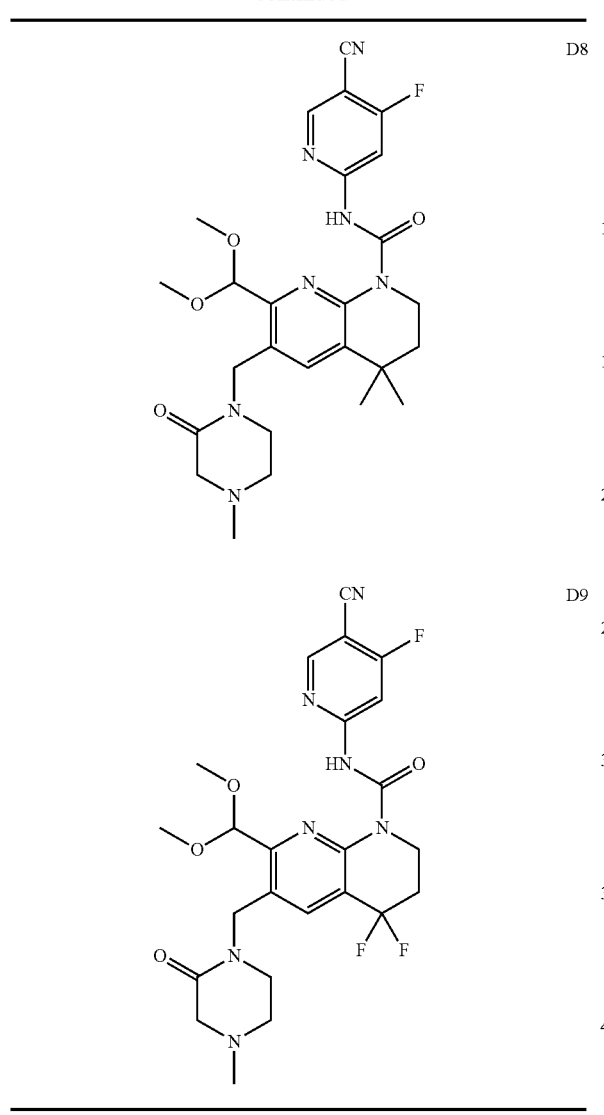
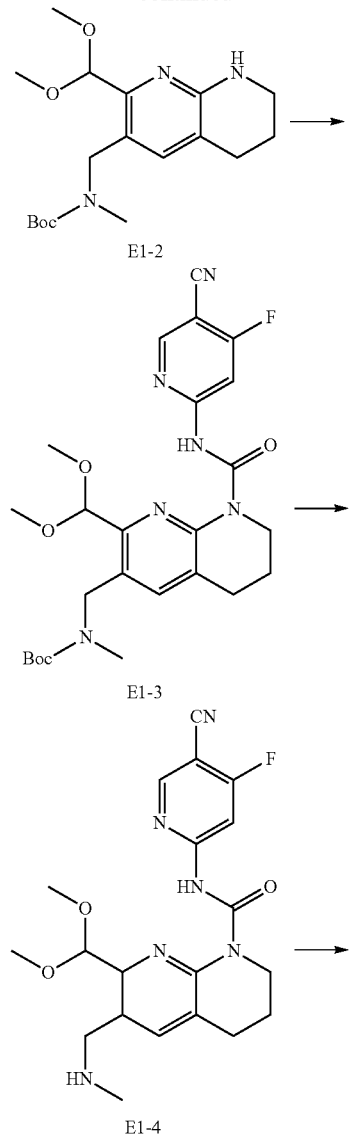
Preparation of Intermediate E1
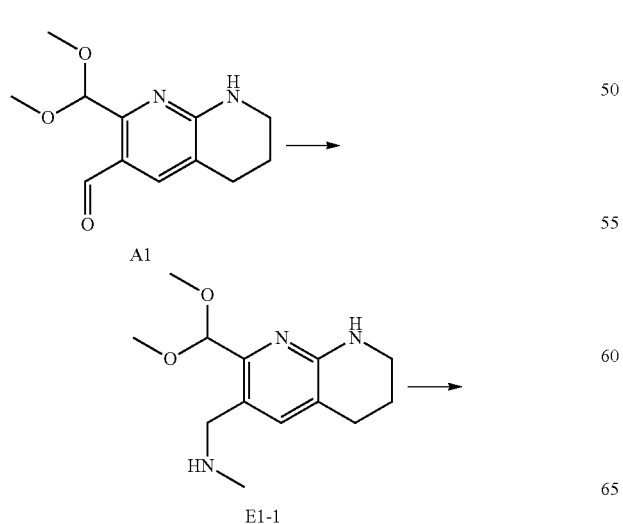
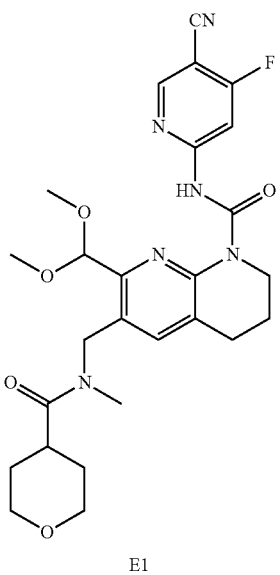 [SMILES: COC(OC)c1nc2c(cc1CN(C)C(=O)C1CCOCC1)CCCN2C(=O)Nc1cc(F)c(C#N)cn1 ; "E1"]

The preparation method of compound E1-1 was according to the synthetic procedure of preparing D1-1 in intermediate D1.

The compound E1-1 (1.02 g, 4.06 mmol), DIEA (0.93 g, 7.20 mmol) and Boc$_2$O (0.89 g, 4.08 mmol) were dissolved in DCM (30 mL). The reaction mixture was stirred for 2.5 hrs at room temperature, and concentrated under reduced pressure, and the residue was purified by a silica gel column to afford the compound E1-2 (1.31 g, 3.73 mmol). MS m/z (ESI): 352 (M+H)$^+$.

The compound E1-2 (1.31 g, 3.73 mmol), the intermediate B1 (1.27 g, 4.94 mmol) and TEA (1.5 mL) were mixed with acetonitrile (30 mL). The reaction mixture was stirred for 4 hours at 70° C., cooled to room temperature, and concentrated under reduced pressure. The residue was purified by a silica gel column to afford the compound E1-3 (0.84 g, 1.63 mmol). MS m/z (ESI): 515 (M+H)$^+$.

The compound E1-3 (0.80 g, 1.55 mmol) and TFA (4 mL) were dissolved in DCM (10 mL) to obtain a solution. The solution was stirred for 5 mins at room temperature, cooled in ice-water bath, then added dropwise into TEA/DCM (8 mL/15 mL) cooled in ice-water bath. The liquids were separated. The organic phase was washed with saturated NaCl aqueous solution (100 mL×1). The organic phase was collected, and concentrated under reduced pressure. The residue was purified by a silica gel column to afford the compound E1-4 (0.57 g, 1.38 mmol). MS m/z (ESI): 415 (M+H)$^+$.

The compound E1-4 (115 mg, 0.28 mmol), tetrahydropyrane-4-formic acid (46 mg, 0.35 mmol), HATU (129 mg, 0.34 mmol), and K$_2$CO$_3$ (82 mg, 0.59 mmol) were mixed with DMF (3 mL). The reaction mixture was stirred for 0.5 h at room temperature, diluted with DCM (20 mL), and washed with saturated NaCl aqueous solution (30 mL×1). The organic phase was collected, and concentrated under reduced pressure. The residue was purified by TLC plate to obtain the compound E1 (62 mg, 0.12 mmol). MS m/z (ESI): 527 (M+H)$^+$.

The following intermediates E2-E4 were synthesized according to the synthesis method of intermediate E1:

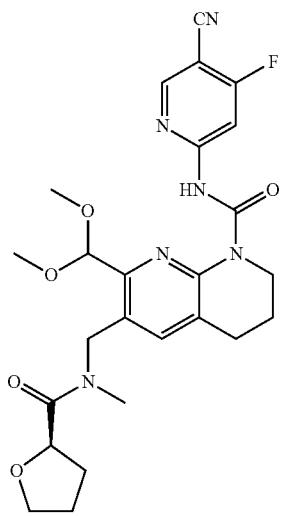 [SMILES: COC(OC)c1nc2c(cc1CN(C)C(=O)[C@H]1CCCO1)CCCN2C(=O)Nc1cc(F)c(C#N)cn1]

E2

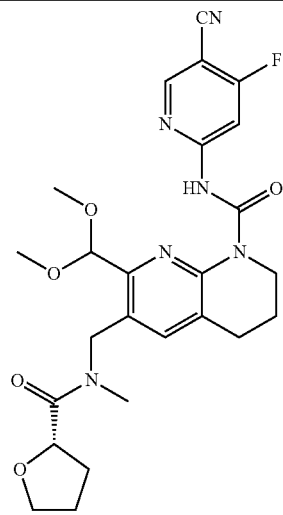

E3

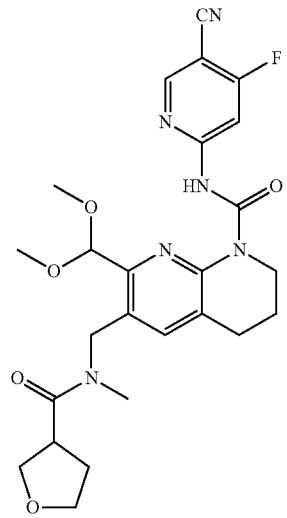 [SMILES: COC(OC)c1nc2c(cc1CN(C)C(=O)C1CCOC1)CCCN2C(=O)Nc1cc(F)c(C#N)cn1]

E4

Preparation of Intermediate F1

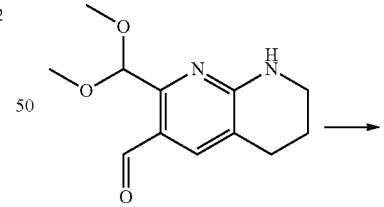

A1

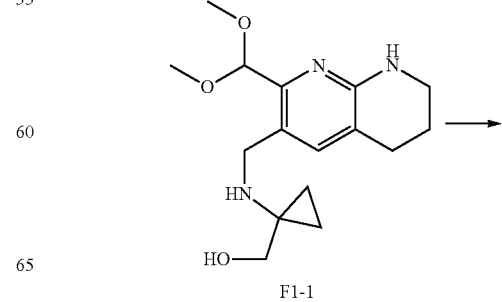

F1-1

-continued

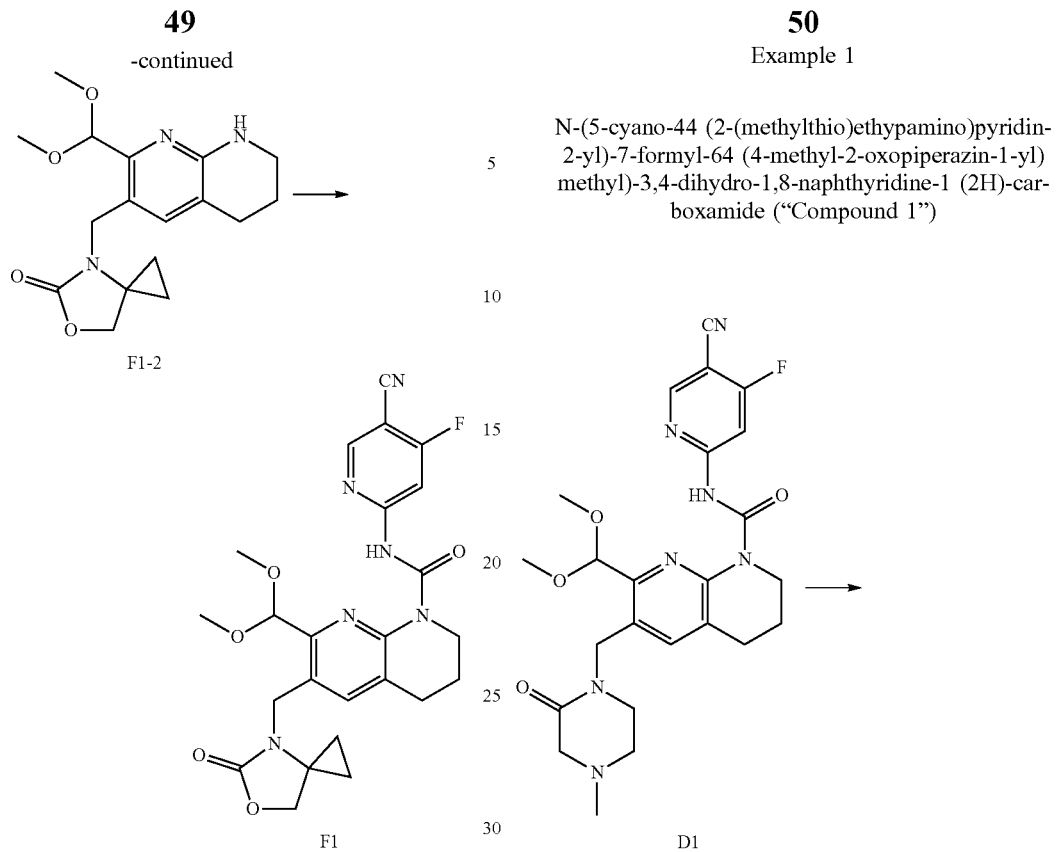

F1-2

F1

The preparation method of compound F1-1 was according to the synthetic procedure of preparing D1-1 in intermediate D1.

The compound F1-1 (0.30 g, 0.98 mmol) and carbonyl diimidazole (0.24 g, 1.48 mmol) were mixed with DCM (10 mL). The reaction mixture was stirred for 2 hrs at 45° C., and purified by a silica gel column to obtain the compound F1-2 (87 mg, 0.26 mmol).

The preparation method of compound F1 was according to the synthetic procedure of preparing E1-3 in intermediate E1. MS m/z (ESI): 497 (M+H)$^+$.

The following intermediates F2 were synthesized according to the synthesis method of intermediate F1:

F2

Example 1

N-(5-cyano-44 (2-(methylthio)ethypamino)pyridin-2-yl)-7-formyl-64 (4-methyl-2-oxopiperazin-1-yl) methyl)-3,4-dihydro-1,8-naphthyridine-1 (2H)-carboxamide ("Compound 1")

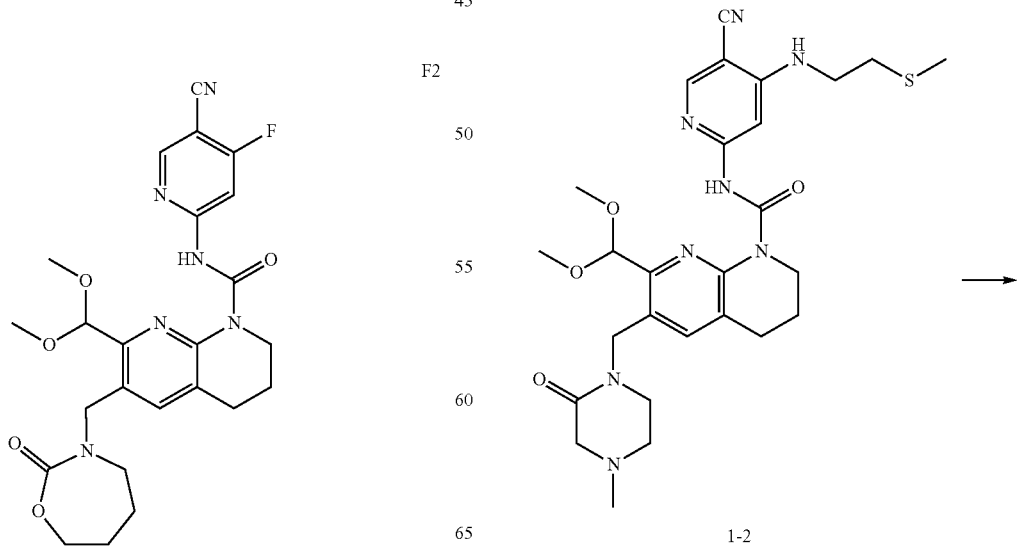

D1

1-2

51
-continued

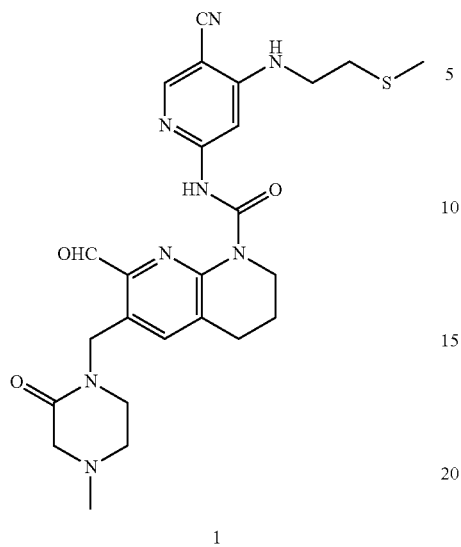

1

The compound D1 (2.04 g, 4.10 mmol), 2-(methioyl) ethylamine hydrochloride (0.83 g, 6.50 mmol) and K₂CO₃ (2.09 g, 15.12 mmol) were mixed with DMF (30 mL). The reaction mixture was stirred at room temperature overnight, diluted with EtOAc (200 mL), and washed with saturated NaCl aqueous solution (150 mL×3). The organic phase was dried with anhydrous Na₂SO₄, and concentrated under reduced pressure. The residue was purified by a silica gel column to afford compound 1-2 (2.08 g, 3.66 mmol). MS m/z (ESI): 569 (M+H)⁺.

The compound 1-2 (1.04 g, 1.83 mmol) was dissolved in H₂O/THF (V/V=1:3, 8 mL), and concentrated hydrochloric acid (2 mL) was added dropwise. The reaction mixture was stirred for 0.5 h at room temperature, and saturated sodium bicarbonate aqueous solution was added to adjust the pH of the reaction mixture to 8. The solid was precipitated, filtered and washed with H₂O (3 mL×2). The filter cake was dispersed in CH₃CN (30 mL) and DCM (2 mL), filtered, and washed with acetonitrile (3 mL×1) to obtain the compound 1 (695 mg, 1.33 mmol). MS m/z (ESI): 523 (M+H)⁺.

$^{1}$H NMR (400 MHz, DMSO-d₆) δ 13.49 (s, 1H), 10.07 (s, 1H), 8.27 (s, 1H), 7.52 (s, 1H), 7.51 (s, 1H), 7.15 (s, 1H), 4.89 (s, 2H), 3.96 (m, 2H), 3.43-3.41 (m, 2H), 3.28-3.27 (m, 2H), 3.05 (s, 2H), 2.93 (m, 2H), 2.72-2.70 (m, 2H), 2.63-2.62 (m, 2H), 2.24 (s, 3H), 2.15 (s, 3H), 1.93 (m, 2H).

52

Example 2

N-(5-cyano-4-(2-(methylthio)ethoxy)pyridin-2-yl)-7-formyl-64 (4-methyl-2-oxopiperazin-1-yl) methyl)-3,4-dihydro-1,8-naphthyridine-1 (2H)-carboxamide ("Compound 2")

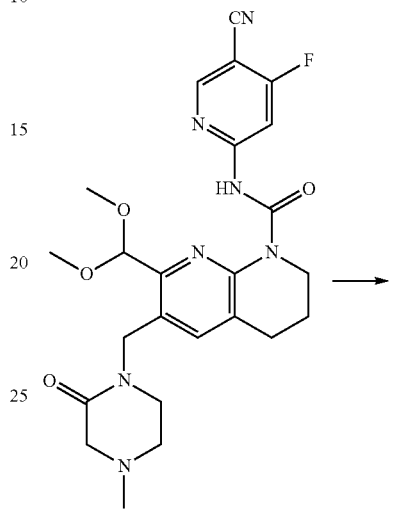

D-1

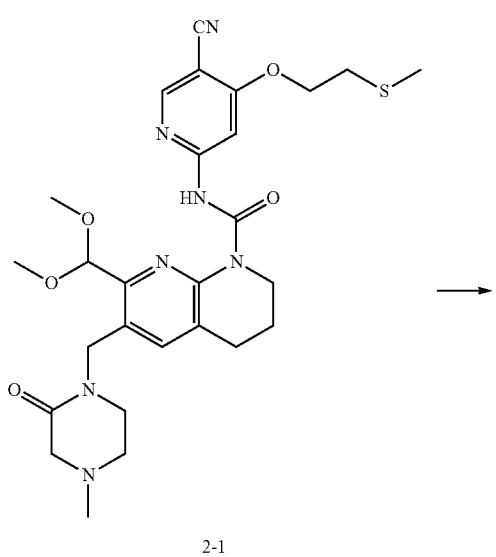

2-1

53
-continued

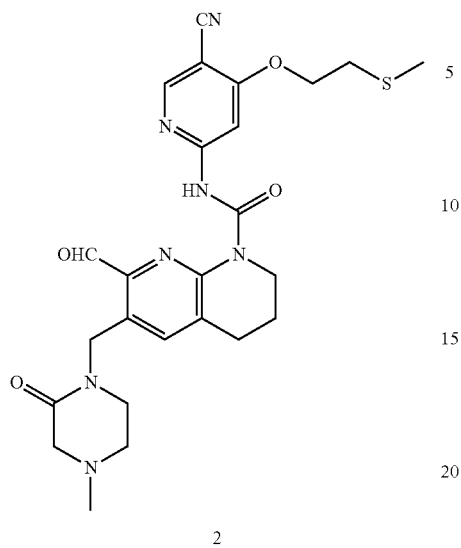

2

The compound D-1 (48 mg, 0.10 mmol), 2-(ethylthio) ethanol (162 mg, 1.76 mmol) and K$_2$CO$_3$ (51 mg, 0.37 mmol) were mixed with DMF (3 mL). The reaction mixture was stirred at 60° C. overnight, diluted with EtOAc (20 mL), and washed with saturated NaCl aqueous solution (20 mL×3). The organic phase was evaporated, and the residue was purified by TLC plate eluted with DCM/MeOH=10/1 (v/v) to obtain the compound 2-1 (46 mg, 0.08 mmol). MS m/z (ESI): 570 (M+H)$^+$.

The compound 2-1 (46 mg, 0.08 mmol) was dissolved in H$_2$O/THF (V/V=1:4, 2.5 mL), and concentrated hydrochloric acid was dropwise added (0.5 mL). The reaction mixture was stirred for 0.5 h at room temperature. Saturated sodium bicarbonate aqueous solution was added to adjust the pH of the reaction mixture to 8. The resulting mixture was extracted with DCM (15 mL×2). The organic phase was dried with anhydrous Na$_2$SO$_4$, and concentrated under reduced pressure to obtain the purified compound 2 (12 mg, 0.02 mmol). MS m/z (ESI): 524 (M+H)$^+$.

$^1$H NMR (400 MHz, DMSO-d$_6$) δ 13.90 (m, 1H), 10.11 (s, 1H), 8.62-8.60 (m, 1H), 7.92 (s, 1H), 7.56 (s, 1H), 4.90 (s, 2H), 4.41-4.33 (m, 2H), 3.98-3.97 (m, 2H), 3.21 (s, 2H), 3.05 (s, 2H), 2.92-2.88 (m, 4H), 2.62 (m, 2H), 2.24-2.20 (m, 6H), 1.94-1.93 (m, 2H).

54
Example 3

N-(5-Cyano-4-thiomorpholinopyridin-2-yl)-7-formyl-6-((4-methyl-2-oxopiperazin-1-yl)methyl)-3,4-dihydro-1,8-naphthyridine-1 (2H)-carboxamide ("Compound 3")

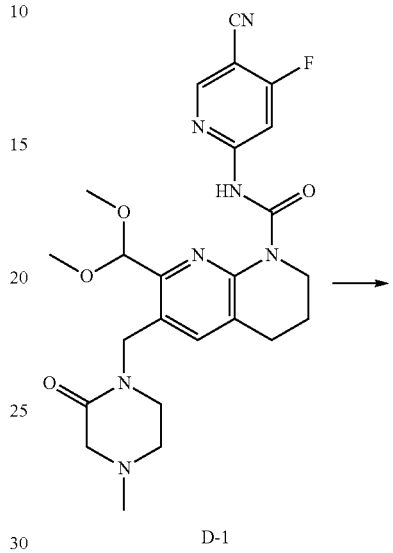

D-1

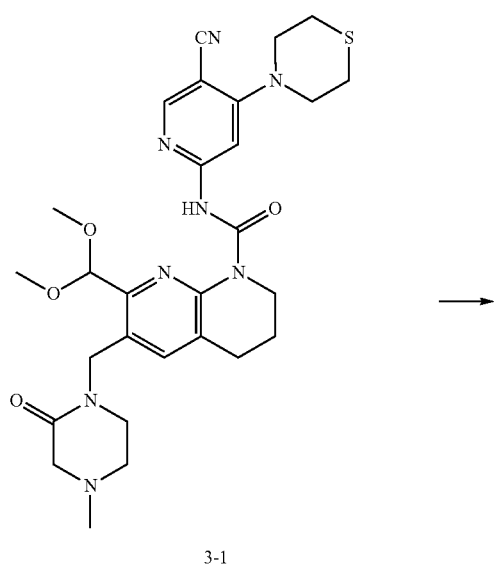

3-1

-continued

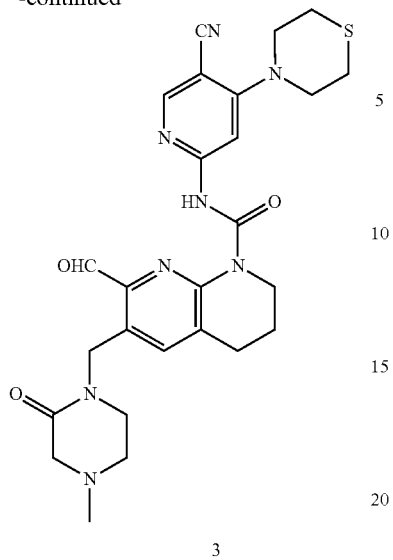

3

Compound D-1 (99 mg, 0.20 mmol), thiomorpholine (94 mg, 0.91 mmol) and K$_2$CO$_3$ (105 mg, 0.76 mmol) were mixed with DMF (4 mL). The reaction mixture was stirred for 3 hrs at room temperature, diluted with EtOAc (20 mL), and washed with saturated NaCl aqueous solution (20 mL×3). The organic phase was evaporated, and the residue was purified by TLC plate eluted with DCM/MeOH=10/1 (v/v) to obtain the compound 3-1 (100 mg, 0.17 mmol). MS m/z (ESI): 581 (M+H)$^+$.

The compound 3-1 (100 mg, 0.17 mmol) was dissolved in H$_2$O/THF (V/V=1:4, 2.5 mL), and concentrated hydrochloric acid (0.5 mL) was added dropwise. The reaction mixture was stirred for 1.5 h at room temperature. Saturated sodium bicarbonate aqueous solution was added to adjust the pH of the reaction mixture to 8. The resulting mixture extracted with DCM (20 mL×4). The organic phase was dried with anhydrous Na$_2$SO$_4$, and concentrated under reduced pressure. The residue was purified by HPLC to obtain the compound 3 (37 mg, 0.07 mmol). MS m/z (ESI): 535 (M+H)$^+$.

$^1$H NMR (400 MHz, DMSO-d$_6$) δ 13.63 (s, 1H), 10.10 (s, 1H), 8.46 (s, 1H), 7.77 (s, 1H), 7.54 (s, 1H), 4.89 (s, 2H), 3.97-3.96 (m, 2H), 3.75-3.73 (m, 4H), 3.27-3.26 (m, 2H), 3.05 (s, 2H), 2.95-2.92 (m, 2H), 2.80-2.77 (m, 4H), 2.62-2.60 (m, 2H), 2.24 (s, 3H), 1.94 (m, 2H).

Example 4

(R)—N-(5-Cyano-4-((1-(methylthio)propan-2-yl)amino)pyridin-2-yl)-7-formyl-6-((4-methyl-2-oxopiperazin-1-yl)methyl)-3,4-dihydro-1,8-naphthyridine-1 (2H)-carboxamide ("Compound 4")

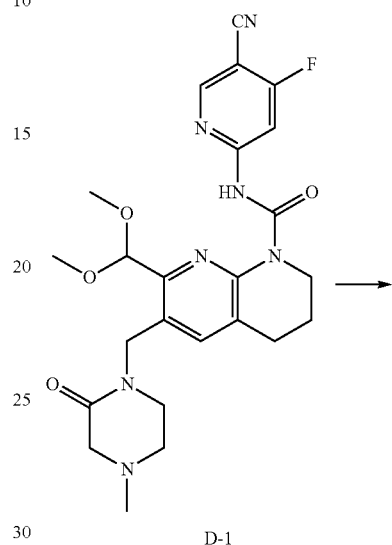

D-1

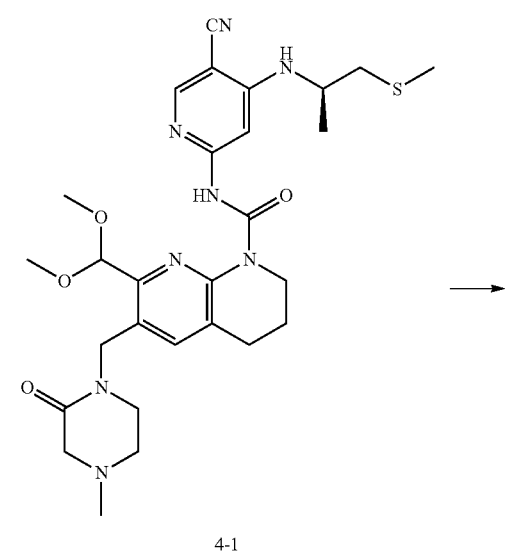

4-1

57

-continued

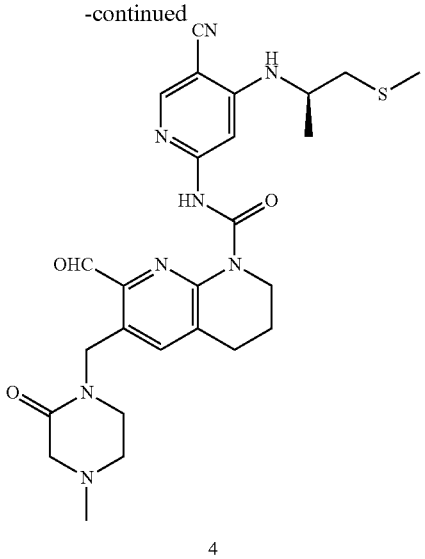

4

The compound D-1 (994 mg, 2.00 mmol), (R)-1-Methylthio-2-propylamine (432 mg, 4.11 mmol) and K$_2$CO$_3$ (893 mg, 6.46 mmol) were mixed with DMF (15 mL). The reaction mixture was stirred overnight at room temperature, diluted with EtOAc (100 mL), and washed with saturated NaCl aqueous solution (100 mL×3). The organic phase was evaporated, and the residue was purified by a silica gel column eluted with DCM/MeOH=98/2 (v/v) to obtain the compound 4-1 (783 mg, 1.34 mmol). MS m/z (ESI): 583 (M+H)$^+$.

The compound 4-1 (783 mg, 1.34 mmol) was dissolved in H$_2$O/THF (V/V=1:4, 7.5 mL), and concentrated hydrochloric acid (1.5 mL) was added dropwise. The reaction mixture was stirred for 0.5 h at room temperature. Saturated sodium bicarbonate aqueous solution was added to adjust the pH of the reaction mixture to 8. The resulting mixture was extracted with DCM (50 mL×3). The organic phase was dried with anhydrous Na$_2$SO$_4$, and concentrated under reduced pressure. The residue was purified by reverse preparation and purification to obtain the compound 4 (542 mg, 1.01 mmol). MS m/z (ESI): 537 (M+H)$^+$.

$^1$H NMR (400 MHz, DMSO-d$_6$) δ 13.47 (s, 1H), 10.07 (s, 1H), 8.26 (s, 1H), 7.55 (s, 1H), 7.52 (s, 1H), 6.76 (d, J=8.3 Hz, 1H), 4.89 (s, 2H), 3.96 (m, 2H), 3.87-3.74 (m, 1H), 3.28 (m, 2H), 3.06 (s, 2H), 2.93 (t, J=5.8 Hz, 2H), 2.82 (m, 1H), 2.64 (m, 3H), 2.24 (s, 3H), 2.13 (s, 3H), 1.93 (m, 2H), 1.29 (d, J=6.3 Hz, 3H).

58

Example 5

N-(5-cyano-4-((tetrahydrothiophene-3-yl)amino)pyridin-2-yl)-7-formyl-6-((4-methyl-2-oxopiperazin-1-yl)methyl)-3,4-dihydro-1,8-naphthyridine-1 (2H)-carboxamide ("Compound 5")

D-1

5-1

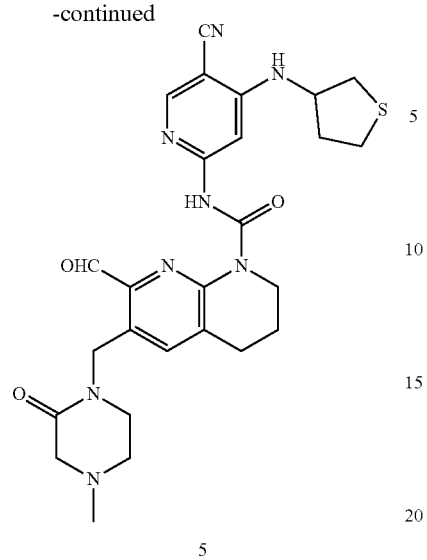

5

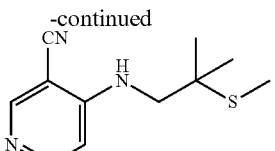

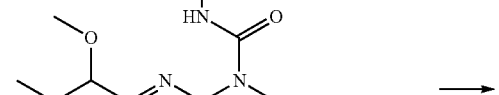

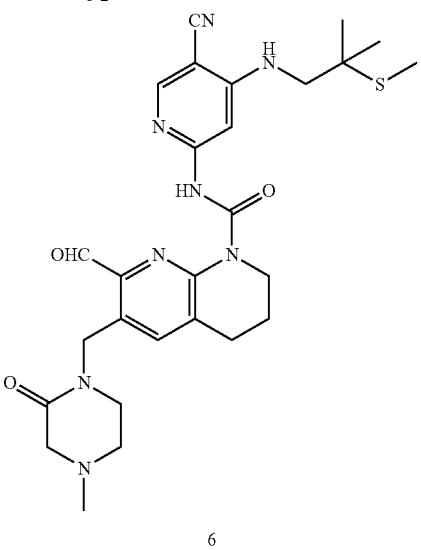

6

The compound D-1 (218 mg, 0.44 mmol), 3-Aminotetrahydrothiophene (168 mg, 1.63 mmol) and $K_2CO_3$ (192 mg, 1.39 mmol) were mixed with DMF (5 mL). The reaction mixture was stirred overnight at room temperature, diluted with EtOAc (30 mL), and washed with saturated NaCl aqueous solution (30 mL×3). The organic phase was evaporated. The residue was purified by TLC plate eluted with DCM/MeOH=20/1 (v/v) to obtain the compound 5-1 (254 mg, 0.44 mmol). MS m/z (ESI): 581 $(M+H)^+$.

The compound 5-1 (254 mg, 0.44 mmol) was dissolve in $H_2O/CH_3CN$ (V/V=1:3, 4 mL), and concentrated hydrochloric acid (1 mL) was added dropwise. The reaction mixture was stirred for 0.5 h at room temperature. Saturated sodium bicarbonate aqueous solution was added to the pH of the reaction mixture to 8. The resulting mixture was extracted with DCM (20 mL×3). The organic phase was dried over anhydrous $Na_2SO_4$, and concentrated under reduced pressure. The residue was purified by HPLC to obtain the compound 5 (100 mg, 0.19 mmol). MS m/z (ESI): 535 $(M+H)^+$.

$^1$H NMR (400 MHz, DMSO-$d_6$) δ 13.50 (s, 1H), 10.08 (s, 1H), 8.30 (s, 1H), 7.60 (s, 1H), 7.53 (s, 1H), 6.90-6.89 (d, 1H), 4.89 (s, 2H), 4.25-4.23 (m, 1H), 3.99-3.96 (m, 2H), 3.27-3.26 (m, 2H), 3.12-3.08 (m, 1H), 3.05 (s, 2H), 2.95-2.92 (m, 4H), 2.86-2.80 (m, 1H), 2.63-2.61 (m, 2H), 2.23 (s, 3H), 2.19-2.12 (m, 2H), 1.95-1.92 (m, 2H).

Example 6

N-(5-cyano-4-((2-methyl-2-(methylthio)propyl)amino)pyridin-2-yl)-7-formyl-6-((4-methyl-2-oxopiperazin-1-yl)methyl)-3,4-dihydro-1,8-naphthyridine-1 (2H)-carboxamide ("Compound 6")

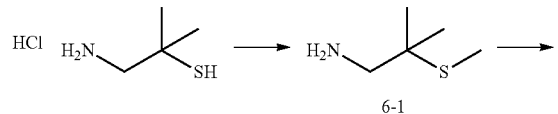

1-Amino-2-methylpropane-2-thiol hydrochloride (1.14 g, 8.05 mmol) was dissolved in EtOH (20 mL). The mixture was cooled on an ice-water bath, NaOH (1.38 g, 34.50 mmol) was added, and iodomethane was added dropwise. The reaction mixture was stirred for 3.5 hrs under ice-water bath condition, then filtered, and concentrated under reduced pressure. The residue was purified by a silica gel column to obtain the compound 6-1 (243 mg, 2.04 mmol). MS m/z (ESI): 120 $(M+H)^+$.

The compound D-1 (137 mg, 0.28 mmol), the compound 6-1 (67 mg, 0.56 mmol) and $K_2CO_3$ (134 mg, 0.97 mmol) were mixed with DMF (3 mL). The reaction mixture was stirred overnight at room temperature, then diluted with EtOAc (20 mL), and washed with saturated NaCl aqueous solution (20 mL×3). The organic phase was evaporated, and the residue was purified by TLC plate eluted with DCM/MeOH=10/1 (v/v) to obtain the compound 6-2 (127 mg, 0.21 mmol). MS: 597 (M+H)+.

The compound 6-2 (127 mg, 0.21 mmol) was dissolved into $H_2O/CH_3CN$ (V/V=1:2, 3 mL), and concentrated hydrochloric acid (1 mL) was added dropwise. The reaction mixture was stirred for 0.5 h at room temperature, and evaporated rotarily. The residue was purified by reverse preparation and purification to obtain the compound 6 (57 mg, 0.10 mmol). MS m/z (ESI): 551 (M+H)⁺.

¹H NMR (400 MHz, DMSO-d$_6$) δ 13.49 (s, 1H), 10.07 (s, 1H), 8.29 (s, 1H), 7.62 (s, 1H), 7.52 (s, 1H), 6.55 (s, 1H), 4.89 (s, 2H), 3.97 (m, 2H), 3.27 (m, 2H), 3.05 (s, 2H), 2.93 (m, 2H), 2.62 (m, 2H), 2.50 (m, 2H), 2.23 (s, 3H), 2.04 (s, 3H), 1.93 (d, J=5.6 Hz, 2H), 1.27 (s, 6H).

Example 7

(R)—N-(5-cyano-4-((1-(methylthio)propan-2-yl)amino)pyridin-2-yl)-7-formyl-6-((2-oxopyrrolidine-1-yl)methyl)-3,4-dihydro-1,8-naphthyridine-1 (2H)-carboxamide ("Compound 7")

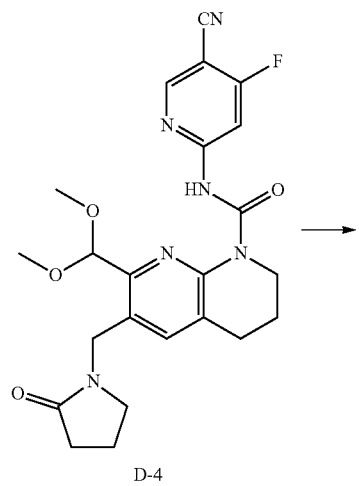

D-4

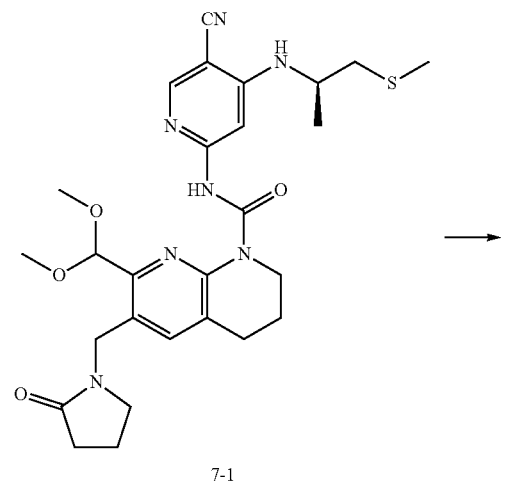

7-1

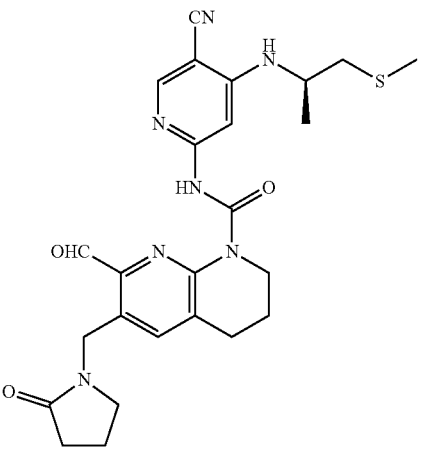

7

The compound D-4 (120 mg, 0.26 mmol), (R)-1-Methylthio-2-propylamine (68 mg, 0.65 mmol) and K$_2$CO$_3$ (129 mg, 0.93 mmol) were mixed with DMF (3 mL). The reaction mixture was stirred overnight at room temperature, then diluted with EtOAc (20 mL), washed with saturated NaCl aqueous solution (20 mL×3), and concentrated under reduced pressure. The residue was purified by TLC plate, to obtain the compound 7-1 (154 mg, 0.28 mmol). MS m/z (ESI): 554 (M+H)⁺.

The compound 7-1 (154 mg, 0.28 mmol) was dissolved in H$_2$O/CH$_3$CN (V/V=1:2, 3 mL), and concentrated hydrochloric acid (0.5 mL) was added dropwise. The reaction mixture was stirred for 0.5 h at room temperature. Saturated sodium bicarbonate aqueous solution was added to adjust the pH of the reaction mixture to 8. The resulting mixture was extracted with DCM (20 mL×3). The organic phase was dried over anhydrous Na$_2$SO$_4$, and concentrated under reduced pressure to obtain the compound 7 (108 mg, 0.21 mmol). MS m/z (ESI): 508 (M+H)⁺.

¹H NMR (400 MHz, DMSO-d$_6$) δ 13.50 (s, 1H), 10.08 (s, 1H), 8.29 (s, 1H), 7.59 (s, 1H), 7.52 (s, 1H), 7.16 (t, J=5.6 Hz, 1H), 4.75 (s, 2H), 4.01-3.91 (m, 2H), 3.41 (m, 2H), 2.94 (t, J=6.3 Hz, 2H), 2.71 (m, 2H), 2.56-2.46 (m, 2H), 2.32 (t, J=8.0 Hz, 2H), 2.16 (s, 3H), 2.02-1.88 (m, 4H).

The following compounds were synthesized according to the synthesis method of example 1:

| compound | Chemical structure | Formula | MS and H¹NMR |
|---|---|---|---|
| 8 | (R)-N-(5-cyano-4-((2-(methylthio)ethyl)amino)pyridin-2-yl)-7-formyl-6-((3-methoxy-2-oxopyrrolidin-1-yl)methyl)-3,4-dihydro-1,8-naphthyridine-1(2H)-carboxamide | | MS m/z (ESI): 524 (M + H)$^+$; $^1$H NMR (400 MHz, DMSO-d$_6$) δ 13.48 (s, 1H), 10.06 (s, 1H), 8.27 (s, 1H), 7.56 (s, 1H), 7.51 (s, 1H), 7.15 (s, 1H), 4.76 (s, 2H), 4.04 (s, 1H), 3.96 (m, 2H), 3.40 (s, 5H), 2.93 (m, 2H), 2.70 (m, 2H), 2.33 (m, 2H), 2.16 (s, 3H), 1.93-1.76 (m, 4H). |
| 9 | N-(5-cyano-4-(((R)-1-(methylthio)propan-2-yl)amino)pyridin-2-yl)-7-formyl-6-(((R)-3-methoxy-2-oxopyrrolidin-1-yl)methyl)-3,4-dihydro-1,8-naphthyridine-1(2H)-carboxamide | | MS m/z (ESI): 538 (M + H)$^+$. |
| 10 | N-(5-cyano-4-((2-(methylthio)phenyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 571 (M + H)$^+$. |

-continued

| compound | Chemical structure | Formula | MS and H¹NMR |
|---|---|---|---|
| 11 | (S)-N-(5-cyano-4-((1-(methylthio)propan-2-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 537 (M + H)+. |
| 12 | N-(5-cyano-4-((2-(cyclohexylthio)ethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 591 (M + H)+. |
| 13 | (S)-N-(5-cyano-4-((2-(methylthio)ethyl)amino)pyridin-2-yl)-7-formyl-6-((3-methoxy-2-oxopyrrolidin-1-yl)methyl)-3,4-dihydro-1,8-naphthyridine-1(2H)-carboxamide | | MS m/z (ESI): 524 (M + H)+. |

| compound | Chemical structure | Formula | MS and H¹NMR |
|---|---|---|---|
| 14 | N-(5-cyano-4-((2-(methylthio)ethyl)amino)pyridin-2-yl)-7-formyl-6-((5-oxo-6-oxa-4-azaspiro[2.4]heptan-4-yl)methyl)-3,4-dihydro-1,8-naphthyridine-1(2H)-carboxamide | | MS m/z (ESI): 522 (M + H)$^+$. |
| 15 | N-(5-cyano-4-((2-(methylthio)ethyl)amino)pyridin-2-yl)-6-((4-cyclopropyl-2-oxopiperazin-1-yl)methyl)-7-formyl-3,4-dihydro-1,8-naphthyridine-1(2H)-carboxamide | | MS m/z (ESI): 549 (M + H)$^+$. |
| 16 | N-(5-cyano-4-((2-(methylthio)ethyl)amino)pyridin-2-yl)-7-formyl-6-((2-oxo-1,3-oxazepan-3-yl)methyl)-3,4-dihydro-1,8-naphthyridine-1(2H)-carboxamide | | MS m/z (ESI): 524 (M + H)$^+$. |

-continued

| compound | Chemical structure | Formula | MS and H¹NMR |
|---|---|---|---|
| 17 | N-(5-cyano-4-((2-(ethylthio)-2-methylpropyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 565 (M + H)+. |
| 18 | N-(5-cyano-4-((2-(methylthio)ethyl)amino)pyridin-2-yl)-4,4-difluoro-7-formyl-6-((4-methyl-2-oxopiperazin-1-yl)methyl)-3,4-dihydro-1,8-naphthyridine-1(2H)-carboxamide | | MS m/z (ESI): 559 (M + H)+. |
| 19 | N-(5-cyano-4-((2-((methyl-d3)thio)ethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 526 (M + H)+. |

-continued

| compound | Chemical structure | Formula | MS and H¹NMR |
|---|---|---|---|
| 20 | N-(5-cyano-4-((tetrahydro-2H-thiopyran-4-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 549 (M + H)⁺. |
| 21 | N-(5-cyano-4-(thiazolidin-3-yl)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 521 (M + H)⁺. |
| 22 | N-(5-cyano-4-((2-(methylthio)propyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 537 (M + H)⁺. |

-continued

| compound | Chemical structure | Formula | MS and H¹NMR |
|---|---|---|---|
| 23 | N-(5-cyano-4-((2-(methylthio)ethyl)amino)pyridin-2-yl)-7-formyl-6-((2-oxopyrrolidin-1-yl)methyl)-3,4-dihydro-1,8-naphthyridine-1(2H)-carboxamide | | MS m/z (ESI): 494 (M + H)+. |
| 24 | N-(5-cyano-4-((2-(methylthio)ethyl)amino)pyridin-2-yl)-6-((1-(dimethylamino)-N-methylcyclopropane-1-carboxamido)methyl)-7-formyl-3,4-dihydro-1,8-naphthyridine-1(2H)-carboxamide | | MS m/z (ESI): 551 (M + H)+. |
| 25 | N-(5-cyano-4-((2-(methylthio)ethyl)amino)pyridin-2-yl)-7-formyl-6-((4-methyl-2-oxopiperazin-1-yl)methyl)-3,4-dihydro-1,8-naphthyridine-4,4-d2-1(2H)-carboxamide | | MS m/z (ESI): 525 (M + H)+. |

-continued

| compound | Chemical structure | Formula | MS and H¹NMR |
|---|---|---|---|
| 26 | N-(5-cyano-4-((2-(cyclo-proylthio)ethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 549 (M + H)+. |
| 27 | N-(5-cyano-4-((2-(methyl-sulfinyl)ethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 539 (M + H)+. |
| 28 | N-(5-cyano-4-((2-(cyclo-pentylthio)ethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 577 (M + H)+. |

-continued

| compound | Chemical structure | Formula | MS and H¹NMR |
|---|---|---|---|
| 29 | Methyl-2-((2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl)thio)acetate | 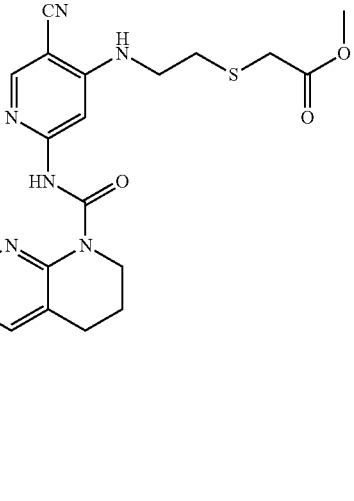 | MS m/z (ESI): 581 (M + H)⁺. |
| 30 | N-(5-cyano-4-((2-(methylthio)ethyl)amino)pyridin-2-yl)-7-formyl-4,4-dimethyl-6-((4-methyl-2-oxopiperazin-1-yl)methyl)-3,4-dihydro-1,8-naphthyridine-1(2H)-carboxamide | 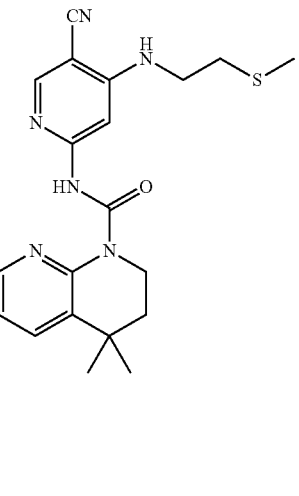 | MS m/z (ESI): 551 (M + H)⁺. |
| 31 | N-(5-cyano-4-((2-(methylthio)ethyl)amino)pyridin-2-yl)-7-formyl-6-((4-methyl-2-oxopiperazin-1-yl)methyl-d2)-3,4-dihydro-1,8-naphthyridine-1(2H)-carboxamide | 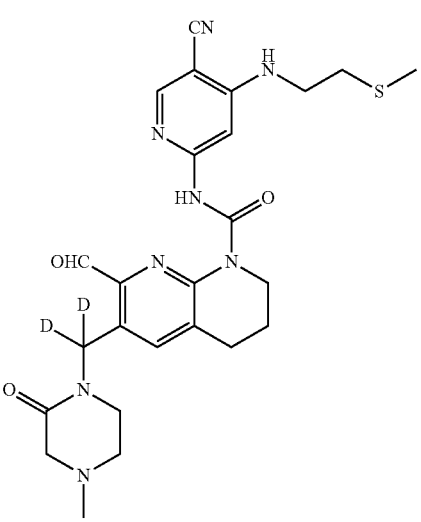 [SMILES: [2H]C([2H])(c1cc2c(nc1C=O)N(C(=O)Nc1cc(NCCSC)c(C#N)cn1)CCC2)N1CCN(C)CC1=O] | MS m/z (ESI): 525 (M + H)⁺. |

| compound | Chemical structure | Formula | MS and H¹NMR |
|---|---|---|---|
| 32 | N-(5-cyano-4-((2-(methyl-thio)ethyl)amino)pyridin-2-yl)-7-formyl-6-(1-(4-methyl-2-oxopiperazin-1-yl)ethyl)-3,4-dihydro-1,8-naphthyridine-1(2H)-carboxamide | | MS m/z (ESI): 537 (M + H)+. |
| 33 | N-(5-cyano-4-(((tetrahydro-thiophen-2-yl)methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 549 (M + H)+. |
| 34 | N-(5-cyano-4-((thietan-2-ylmethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 535 (M + H)+. |

-continued

| compound | Chemical structure | Formula | MS and H¹NMR |
|---|---|---|---|
| 35 | N-(5-cyano-4-(((tetrahydro-2H-thiopyran-2-yl)methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 563 (M + H)⁺. |
| 36 | N-(5-cyano-4-(1-thia-8-azaspiro[4.5]decan-8-yl)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 589 (M + H)⁺. |
| 37 | N-(5-cyano-4-(((tetrahydro-2H-thiopyran-4-yl)methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 563 (M + H)⁺. |

| compound | Chemical structure | Formula | MS and H¹NMR |
|---|---|---|---|
| 38 | N-(5-cyano-4-(((4-methyl-thiomorpholin-2-yl)methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 578 (M + H)+. |
| 39 | N-(4-(((1,4-oxathian-2-yl)methyl)amino)-5-cyanopyridin-2-yl)-7-formyl-6-((4-methyl-2-oxopiperazin-1-yl)methyl)-3,4-dihydro-1,8-naphthyridine-1(2H)-carboxamide | | MS m/z (ESI): 565 (M + H)+. |
| 40 | N-(5-cyano-4-((2-(methylthio)cyclopentyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 563 (M + H)+. |

| compound | Chemical structure | Formula | MS and H¹NMR |
|---|---|---|---|
| 41 | N-(5-cyano-4-((4-(methylthio)tetrahydrofuran-3-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 565 (M + H)⁺. |
| 42 | N-(5-cyano-4-(3-(methylthio)pyrrolidin-1-yl)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 549 (M + H)⁺. |
| 43 | N-(5-cyano-4-(((1-(methylthio)cyclopropyl)methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 549 (M + H)⁺. |

| compound | Chemical structure | Formula | MS and H¹NMR |
|---|---|---|---|
| 44 | N-(5-cyano-4-((1-((methyl-thio)methyl)cyclopropyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 549 (M + H)⁺. |
| 45 | N-(5-cyano-4-((4-(methyl-thio)tetrahydro-2H-pyran-3-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 579 (M + H)⁺. |
| 46 | N-(5-cyano-4-((3-(methyl-thio)tetrahydro-2H-pyran-4-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 579 (M + H)⁺. |

-continued

| compound | Chemical structure | Formula | MS and H¹NMR |
|---|---|---|---|
| 47 | N-(5-cyano-4-(thietan-3-yl-amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 521 (M + H)$^+$. |
| 48 | N-(5-cyano-4-(((1-(ethyl-thio)cyclopropyl)methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 563 (M + H)$^+$. |
| 49 | N-(5-cyano-4-((1-((ethyl-thio)methyl)cyclopropyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 563 (M + H)$^+$. |

| compound | Chemical structure | Formula | MS and H¹NMR |
|---|---|---|---|
| 50 | N-(5-cyano-4-((4-methoxy-tetrahydrothiophene-3-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 565 (M + H)⁺. |
| 51 | N-(5-cyano-4-((4-methoxy-tetrahydro-2H-thiopyran-3-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 579 (M + H)⁺. |
| 52 | N-(5-cyano-4-((3-methoxy-tetrahydro-2H-thiopyran-4-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 579 (M + H)⁺. |

-continued

| compound | Chemical structure | Formula | MS and H¹NMR |
|---|---|---|---|
| 53 | N-(5-cyano-4-(2-(ethylthio)ethoxy)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 538 (M + H)$^+$. |
| 54 | N-(5-cyano-4-((1-(methylthio)propan-2-yl)oxy)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 538 (M + H)$^+$. |
| 55 | N-(5-cyano-4-((thiazol-5-yl-methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 546 (M + H)$^+$. |

| compound | Chemical structure | Formula | MS and H¹NMR |
|---|---|---|---|
| 56 | N-(5-cyano-4-((thiazol-2-yl-methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 546 (M + H)⁺. |
| 57 | N-(5-cyano-4-((isothiazol-5-yl-methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 546 (M + H)⁺. |
| 58 | N-(5-cyano-4-(((5-methyl-thiophen-2-yl)methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 559 (M + H)⁺. |

| compound | Chemical structure | Formula | MS and H¹NMR |
|---|---|---|---|
| 59 | N-(5-Cyano-4-((thiazol-4-yl-methyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 546 (M + H)⁺. |
| 60 | N-(5-cyano-4-((1-(thiazol-2-yl)ethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 560 (M + H)⁺. |
| 61 | N-(5-cyano-4-((1-(5-methyl-thiophen-2-yl)ethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 573 (M + H)⁺. |

| compound | Chemical structure | Formula | MS and H¹NMR |
|---|---|---|---|
| 62 | N-(5-cyano-4-((2-((trifluoromethyl)thio)ethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 577 (M + H)$^+$; $^1$H NMR (400 MHz, DMSO-d$_6$) δ 13.51 (s, 1H), 10.08 (s, 1H), 8.31 (s, 1H), 7.53 (s, 1H), 7.51 (s, 1H), 7.28 (t, J = 5.6 Hz, 1H), 4.89 (s, 2H), 3.98 (dd, J = 16.4, 11.0 Hz, 2H), 3.54 (dd, J = 13.1, 6.4 Hz, 2H), 3.37-3.21 (m, 2H), 3.06 (s, 2H), 2.93 (t, J = 6.1 Hz, 2H), 2.64 (t, J = 5.3 Hz, 2H), 2.57-2.42 (m, 2H), 2.24 (s, 3H), 1.99-1.82 (m, 2H). |
| 63 | 2-((2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl)thio)acetic acid | | MS m/z (ESI): 567 (M + H)$^+$. |
| 64 | N-(5-cyano-4-((3-(methylthio)propyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 537 (M + H)$^+$; $^1$H NMR (400 MHz, DMSO-d$_6$) δ 13.47 (s, 1H), 10.07 (s, 1H), 8.26 (s, 1H), 7.52 (s, 1H), 7.49 (s, 1H), 7.13 (t, J = 5.4 Hz, 1H), 4.89 (s, 2H), 4.05-3.84 (m, 2H), 3.32 (m, 2H), 3.30-3.23 (m, 2H), 3.06 (s, 2H), 2.93 (t, J = 6.0 Hz, 2H), 2.62 (t, J = 5.3 Hz, 2H), 2.57-2.52 (m, 2H), 2.24 (s, 3H), 2.07 (s, 3H), 1.97-1.82 (m, 4H). |

| com-pound | Chemical structure | Formula | MS and H¹NMR |
|---|---|---|---|
| 65 | N-(5-cyano-4-((1,1-dioxidotetrahydrothiophen-3-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 567 (M + H)⁺; ¹H NMR (400 MHz, DMSO-d₆) δ 13.53 (s, 1H), 10.07 (s, 1H), 8.32 (s, 1H), 7.54 (d, J = 4.8 Hz, 2H), 7.27 (d, J = 7.4 Hz, 1H), 4.89 (s, 2H), 3.97 (m, 2H), 3.53 (m, 1H), 3.42-3.33 (m, 2H), 3.27 (m, 2H), 3.25-3.13 (m, 2H), 3.06 (m, 2H), 2.93 (m, 2H), 2.62 (m, 2H), 2.50 (m, 2H), 2.24 (s, 3H), 1.94 (m, 2H). |
| 66 | N-(5-Cyano-4-((2-(phenylthio)ethyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 585 (M + H)⁺; ¹H NMR (400 MHz, DMSO-d₆) δ 13.49 (s, 1H), 10.08 (s, 1H), 8.28 (s, 1H), 7.51 (d, J = 15.3 Hz, 2H), 7.41 (d, J = 7.3 Hz, 2H), 7.35 (t, J = 7.7 Hz, 2H), 7.27-7.18 (m, 2H), 4.89 (s, 2H), 4.04-3.92 (m, 2H), 3.43 (m, 2H), 3.27 (m, 2H), 3.24-3.17 (m, 2H), 3.06 (s, 2H), 2.94 (t, J = 5.9 Hz, 2H), 2.63 (t, J = 5.4 Hz, 2H), 2.24 (s, 3H), 1.98 (m, 2H). |
| 67 | N-(5-cyano-4-((2-(pyridin-3-yl-thio)ethyl)amino)pyridin-2-yl)-7-formyl-6-((4-methyl-2-oxopiperazin-1-yl)methyl)-3,4-dihydro-1,8-diazanonaphthalene-1(2H)-carboxamide | | MS m/z (ESI): 586 (M + H)⁺. |

-continued

| compound | Chemical structure | Formula | MS and H¹NMR |
|---|---|---|---|
| 68 | N-(5-Cyano-4-((isothiazol-3-yl-methyl)amino)pyridin-2-yl)-7-formyl-6-((4-methyl-2-oxopiperazin-1-yl)methyl)-3-1,4-dihydro-1,8-naphthyridine-1(2H)-carboxamide | | MS m/z (ESI): 546 (M + H)$^+$; $^1$H NMR (400 MHz, DMSO-d$_6$) δ 13.45 (s, 1H), 10.05 (s, 1H), 9.03 (d, J = 4.6 Hz, 1H), 8.30 (s, 1H), 7.68 (t, J = 6.0 Hz, 1H), 7.51 (s, 1H), 7.44 (s, 1H), 7.32 (d, J = 4.7 Hz, 1H), 4.88 (s, 2H), 4.59 (d, J = 6.0 Hz, 2H), 3.95-3.88 (m, 2H), 3.26 (t, J = 5.4 Hz, 2H), 3.05 (s, 2H), 2.91 (t, J = 6.1 Hz, 2H), 2.61 (t, J = 5.4 Hz, 2H), 2.53-2.48 (m, 2H), 2.23 (s, 3H). |
| 69 | N-(5-cyano-4-(((2R)-1-(methylsulfinyl)propan-2-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 553 (M + H)$^+$. |
| 70 | (R)-N-(5-cyano-4-((1-(methylthio)propan-2-yl)amino)pyridin-2-yl)-7-formyl-6-((2-oxo-1,3-oxozepan-3-yl)methyl)-3,4-dihydro-1,8-naphthyridine-1(2H)-carboxamide | | MS m/z (ESI): 538 (M + H)$^+$; $^1$H NMR (400 MHz, DMSO-d$_6$) δ 13.50 (s, 1H), 10.05 (s, 1H), 8.27 (s, 1H), 7.70 (s, 1H), 7.61-7.42 (s, 1H), 6.73 (t, J = 25.0 Hz, 1H), 4.78 (s, 2H), 4.08 (m, 2H), 3.97 (m, 2H), 3.88-3.75 (m, 1H), 3.27 (m, 2H), 2.96 (t, J = 5.7 Hz, 2H), 2.50 (m, 2H), 2.13 (s, 3H), 1.94 (m, 2H), 1.77 (m, 2H), 1.60 (m, 2H), 1.30 (d, J = 6.3 Hz, 3H). |

Example 71

N-(5-cyano-44 (2-(ethylthio)ethypamino)pyridin-2-yl)-7-formyl-64 (4-methyl-2-oxopiperazin-1-yl)methyl)-3,4-dihydro-1,8-naphthyridine-1 (2H)-carboxamide hydrochloride ("Compound 71")

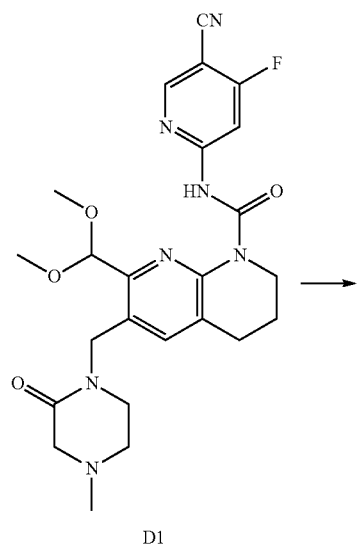

D1

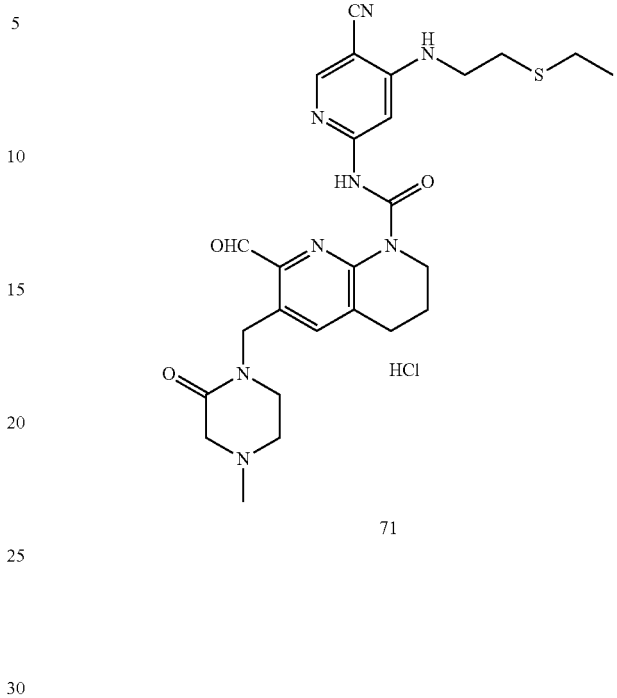

71

The compound 71-1 was synthesized according to the synthesis method of compound 1-2 of example 1.

Compound 71-1 (25 mg, 0.043 mmol) was dissolved in $H_2O/CH_3CN$ (V/V=1:2, 3 mL), and concentrated hydrochloric acid (1 mL) was added dropwise. The reaction mixture was stirred for 0.5 h at room temperature, and concentrated under reduced pressure to obtain the compound 71 (30 mg, 0.052 mmol). MS m/z (ESI): 537 (M+H)$^+$.

$^1$H NMR (400 MHz, DMSO-d$_6$) δ 13.64 (s, 1H), 11.76 (m, 1H), 10.08 (s, 1H), 8.32 (s, 1H), 7.89 (s, 1H), 7.46 (s, 1H), 7.34 (s, 1H), 5.17-5.12 (m, 1H), 4.82 (m, 1H), 3.99 (m, 4H), 3.67-3.42 (m, 6H), 2.86 (s, 3H), 2.76-2.73 (m, 2H), 2.63-2.58 (m, 2H), 1.93 (m, 2H), 1.21 (m, 3H).

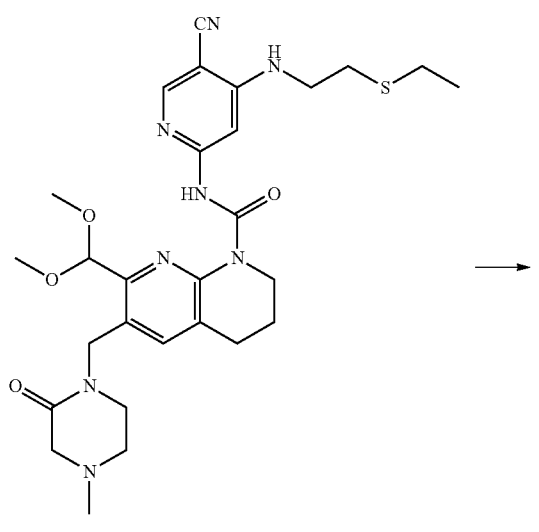

71-1

The following compounds were synthesized according to the synthesis method of example 71:

| Compound | Chemical structure | Formula | MS and H¹NMR |
|---|---|---|---|
| 72 | N-(5-cyano-4-((2-(methyl-sulfonyl)ethyl)amino)pyridin-2-yl)-7-formyl-6-((4-methyl-2-oxopiperazin-1-yl)methyl)-3,4-dihydro-1,8-naphthyridine-1(2H)-carboxamide hydrochloride | | MS m/z (ESI): 555 (M + H)⁺; ¹H NMR (400 MHz, DMSO-d₆) δ 13.76 (s, 1H), 12.23 (m, 1H), 10.10 (s, 1H), 8.39 (s, 1H), 7.98 (s, 1H), 7.46 (s, 1H), 7.43 (s, 1H), 5.23-5.18 (m, 1H), 4.78-4.71 (m, 1H), 3.73-3.68 (m, 4H), 3.50-3.47 (m, 4H), 3.08 (s, 2H), 3.08-2.95 (m, 7H), 2.84 (s, 3H), 1.94 (m, 2H). |
| 73 | N-(5-cyano-4-((2-(methylthio)ethyl)amino)pyridin-2-yl)-7-formyl-6-((N-methyltetrahydro-2H-pyran-4-carboxamido)methyl)-3,4-dihydro-1,8-naphthyridine-1(2H)-carboxamide hydrochloride | | MS m/z (ESI): 552 (M + H)⁺; ¹H NMR (400 MHz, DMSO-d₆) δ 14.06-13.81 (m, 1H), 10.14-10.11 (m, 1H), 8.39-8.37 (m, 1H), 7.72 (s, 1H), 7.51-7.49 (m, 1H), 7.41-7.36 (m, 1H), 5.05-4.88 (d, 2H), 3.97 (m, 2H), 3.89-3.86 (m, 2H), 3.50-3.48 (m, 2H), 3.41-3.40 (m, 2H), 3.38-3.37 (s, 2H), 3.07 (s, 3H), 2.99-2.91 (m, 4H), 2.83 (s, 1H), 2.76-2.72 (m, 2H), 2.15 (s, 3H), 1.94 (m, 2H), 1.62-1.56 (m, 2H). |
| 74 | (R)-N-(5-cyano-4-((2-(methylthio)ethyl)amino)pyridin-2-yl)-7-formyl-6-((N-methyltetrahydrofuran-2-carboxamido)methyl)-3,4-dihydro-1,8-naphthyridine-1(2H)-carboxamide hydrochloride | | MS m/z (ESI): 538 (M + H)⁺; ¹H NMR (400 MHz, DMSO-d₆) δ 14.02-13.77 (m, 1H), 10.18-10.09 (m, 1H), 8.38-8.36 (m, 1H), 7.66 (s, 1H), 7.57-7.55 (m, 1H), 7.42-7.37 (m, 1H), 5.14-5.03 (m, 1H), 4.94-4.79 (m, 2H), 3.97 (m, 3H), 3.83-3.78 (m, 2H), 3.50-3.48 (m, 2H), 3.05 (s, 2H), 2.94-2.91 (m, 2H), 2.75-2.72 (m, 2H), 2.15 (s, 3H), 2.13-2.09 (m, 2H), 1.94 (m, 2H), 1.88-1.85 (m, 2H). |

-continued

| Compound | Chemical structure | Formula | MS and H¹NMR |
|---|---|---|---|
| 75 | (S)-N-(5-cyano-4-((2-(methylthio)ethyl)amino)pyridin-2-yl)-7-formyl-6-((N-methyltetrahydrofuran-2-carboxamido)methyl)-3,4-dihydro-1,8-naphthyridine-1(2H)-carboxamide hydrochloride | 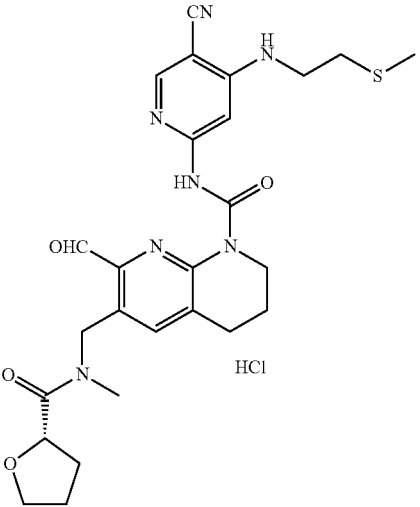 [SMILES: CSCCNc1cc(NC(=O)N2CCCc3cc(CN(C)C(=O)[C@@H]4CCCO4)c(C=O)nc32)ncc1C#N ; Cl] | MS m/z (ESI): 538 (M + H)$^+$; $^1$H NMR (400 MHz, DMSO-d$_6$) δ 14.07-13.80 (m, 1H), 10.15-10.09 (m, 1H), 8.39-8.38 (m, 1H), 7.74 (s, 1H), 7.57-7.56 (m, 1H), 7.41-7.36 (m, 1H), 5.14-5.03 (m, 1H), 4.99-4.79 (m, 2H), 3.97 (m, 3H), 3.81-3.77 (m, 2H), 3.50-3.47 (m, 2H), 3.74-3.66 (m, 2H) 3.06 (s, 2H), 2.97-2.91 (m, 2H), 2.76-2.70 (m, 2H), 2.15 (s, 3H), 2.09-2.03 (m, 2H), 1.96-1.83 (m, 4H). |
| 76 | N-(5-cyano-4-((2-(methylthio)ethyl)amino)pyridin-2-yl)-7-formyl-6-((N-methyltetrahydrofuran-3-carboxamido)methyl)-3,4-dihydro-1,8-naphthyridine-1(2H)-carboxamide hydrochloride | 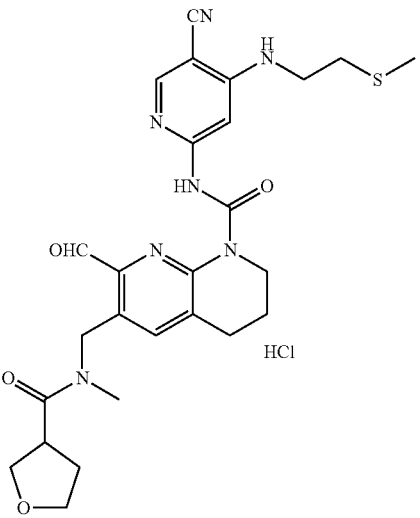 [SMILES: CSCCNc1cc(NC(=O)N2CCCc3cc(CN(C)C(=O)C4CCOC4)c(C=O)nc32)ncc1C#N ; Cl] | MS m/z (ESI): 538 (M + H)$^+$; $^1$H NMR (400 MHz, DMSO-d$_6$) δ 14.06-13.80 (m, 1H), 10.14-10.09 (m, 1H), 8.38-8.37 (m, 1H), 7.71 (s, 1H), 7.54 (m, 2H), 7.41-7.34 (m, 1H), 4.89 (s, 2H), 3.97-3.91 (m, 2H), 3.76-3.68 (m, 2H), 3.48-3.47 (m, 3H), 3.05 (s, 3H), 2.97-2.93 (m, 2H), 1.87 (m, 1H), 2.75-2.74 (m, 2H), 2.15 (s, 3H), 2.02-1.94 (m, 2H), 1.22 (m, 2H). |

The following compounds were synthesized by selecting appropriate raw materials:

| Compound | Chemical structure | Formula | MS and H¹NMR |
|---|---|---|---|
| 77 | N-(5-cyano-4-((1-mercapto-2-methylpropan-2-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 537 (M + H)⁺. |
| 78 | N-(5-cyano-4-(4-mercapto-4-methylpiperidin-1-yl)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 563 (M + H)⁺. |
| 79 | N-(5-cyano-4-((2-mercapto-2-methylpropyl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 537 (M + H)⁺. |

-continued

| Compound | Chemical structure | Formula | MS and H¹NMR |
|---|---|---|---|
| 80 | N-(5-cyano-4-(3,6-dihydro-2H-thiopyran-4-yl)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 532 (M + H)⁺. |
| 81 | Ethyl-2-((2-((5-cyano-2-(7-formyl-6-((4-methyl-2-oxopiperazin-1-yl)methyl)-1,2,3,4-tetrahydro-1,8-naphthyridine-1-carboxamide)pyridin-4-yl)amino)ethyl)thio)acetate | | MS m/z (ESI): 595 (M + H)⁺. |
| 82 | N-(5-cyano-4-((1-(methyl-thio)propan-2-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 537 (M + H)⁺. |

| Compound | Chemical structure | Formula | MS and H¹NMR |
|---|---|---|---|
| 83 | N-(5-cyano-4-(((2R)-1-(methyl-sulfonyl)propan-2-yl)amino)pyridin-2-yl)-7-formyl-6-((4-methyl-2-oxopiperazin-1-yl)methyl)-3,4-dihydro-1,8-naphthyridine-1(2H)-carboxamide | | MS m/z (ESI): 569 (M + H)+. |

Analysis of Pharmacological and Pharmacodynamic Experiment

Example A: FGFR4 Enzymatic Experiments

The FGFR4 kinase inhibition of compounds was tested by using mobility shift assay in this experiment, and the rate of FGFR4 kinase inhibition of compounds or half inhibitory concentration $IC_{50}$ thereof was obtained.

(1) The compounds to be tested were prepared to gradient concentration in 100% DMSO, and diluted with buffer solution (the pH of the buffer solution was 7.5, and the buffer solution contained 50 mM HEPES (N-(2-Hydroxyethyl) piperazine-N'-2-sulfonic acid), 0.00015% (ml/ml) Brij-35 (Dodecyl poly ethylene glycol ether) and the water) to the reacting solution with 10% DMSO. The reacting solution was added into the 384-well plate. For example, when the initial concentration of the compounds was 10 μM, 500 μM would be prepared with 100% DMSO, and diluted in gradient of 10 concentrations, and then diluted 10 times in gradient with buffer solution to prepare an intermediate dilution of the compound containing 10% DMSO. 5 μl of the intermediate dilution was transferred to 384-well plate;

(2) FGFR4 enzyme (Invitrogen, Cat. No PR4380A, Lot. No 1856505A) was diluted with the buffer solution (the pH of the buffer solution was 7.5, and the buffer solution contained 50 mM HEPES, 0.00015% (ml/ml) Brij-35, 2 mM DTT (Dithiothreitol) and the water) to obtain a FGFR enzyme solution with the optimum concentration (the final concentration of the FGFR enzyme solution was 12.5 nM). 10 μl FGFR enzyme solution was transferred to 384-well plate above mentioned in step (1), and incubated with the compounds to be tested for 10-15 minutes.

(3) The substrate (Peptide FAM-P22, GL Biochem, Cat. No. 112393, Lot. No. P180116-MJ112393) was diluted with buffer solution (the pH of the buffer solution was 7.5, and the buffer solution contained 50 mM HEPES, 0.00015% (ml/ml) Brij-35, 10 mM $MgCl_2$, adenosine triphosphate 6604 under Km and the water) to obtain a substrate solution with the optimum concentration of 10 nM. 10 μl the substrate solution was added into the 384-well plate above mentioned in step (2) to start the reaction, and the reaction was undergoing at 28° C. for 1 hour;

(4) the conversion rate was read with Caliper Reader, and the inhibition rate was the average of the two testing values.

(5) The $IC_{50}$ value was obtained by XL-fit software fitting, and the measured results are shown in Table 1 below:

TABLE 1

| Compound | FGFR4 ($IC_{50}$ nM) | Compound | FGFR4 ($IC_{50}$ nM) |
|---|---|---|---|
| Compound 1 | 1.5 | Compound 59 | 2.1 |
| Compound 4 | 1.4 | Compound 60 | 3.0 |
| Compound 5 | 2.0 | Compound 62 | 1.7 |
| Compound 6 | 2.1 | Compound 64 | 1.6 |
| Compound 7 | 1.5 | Compound 69 | 2.1 |
| Compound 8 | 0.42 | Compound 71 | 2.4 |
| Compound 9 | 2.0 | Compound 72 | 2.0 |
| Compound 16 | 2.2 | Compound 73 | 2.3 |
| Compound 20 | 4.4 | Compound 75 | 1.8 |
| Compound 27 | 2.4 | Compound 76 | 2.1 |
| Compound 55 | 3.0 | Compound 83 | 2.1 |
| Compound 56 | 1.6 | Reference compound (roblitinib) | 2.9 |
| Compound 58 | 2.1 | | |

The reference compound in the present invention has the following structure

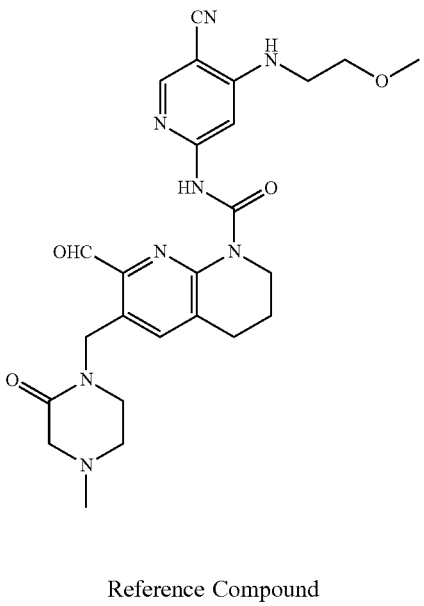

Reference Compound

From Table 1, it can be seen that most compounds in the table have better inhibitory effect on FGFR4 than the reference compound, such as, compound 1, compound 4, compound 5, compound 6, compound 7, compound 9, compound 16, compound 27, compound 56, compound 58, compound 59, compound 62, compound 64, compound 69, compound 71, compound 72, compound 73, compound 75, compound 76 and compound 83.

Example B: Hepatoma Cell Proliferation Inhibition Experiment

In this experiment, the MTS method was used to test the inhibitory effect of the compounds on the proliferation of Hepatoma cell Hep3B (high expression of FGFR4 and FGF19), and the half inhibitory concentration $IC_{50}$ of the compounds to Hep3B was obtained. The Hep3B cell line was purchased from ATCC, and the complete culture medium of the Hep3B cell line was MEM+10% FBS+1% PS. MEM cell culture medium, fetal bovine serum, and trypsin were purchased from Gibco, cell culture flasks were purchased from Greiner, and disposable Cell Counting Plate and Taittinger Blue Solution were purchased from Bio-Rad.

(1) 100 μl Hepatoma cell Hep3B suspension was seeded in a 96-well cell culture plate, and the density of each well was $2.0 \times 10^4$ cells/ml. The culture plate was incubated in incubator for 16-24 h (37° C., 5% $CO_2$);

(2) The compound solution to be tested with different concentration obtained by gradient dilution (15 mM or 7.5 mM of stock solution was prepared by dissolving the compounds in DMSO, then the stock solution was diluted to solution in eight different concentrations with DMSO in a 5-fold gradient. 1.6 μl compound+400 μl MEM (containing 1% PS), 100 μl/well, 3 wells per concentration.) was added into the culture plate, and the culture plate was incubated for 120 h in incubator (37° C., 5% $CO_2$).

(3) A mixture of MTS (3-(4,5-dimethylthiazol-2-yl)-5-(3-carboxymethoxyphenyl)-2-(4-sulfophenyl)-2H-tetrazolium)/PMS (phenazine methosulfate) was added into each well for coloration, and MTS/PMS in the mixture was at a ratio of 20:1 (ml:ml). 30 μl of the mixture was added into each well of the culture plate above mentioned in step (2), then the culture plate was incubated for 3 h in the incubator.

(4) The chemiluminescence signal value of each plate was measured at a wavelength of 492 nm using the enzyme-labeled instrument;

(5) The inhibition rate was calculated by the chemiluminescence signal value;

(6) According to the inhibition rate of the different concentrations, the $IC_{50}$ values of the compounds were obtained by curve fitting.

The measured results were as shown in the following table 2:

TABLE 2

| Compound | Hep3B($IC_{50}$ μM) | Compound | Hep3B($IC_{50}$ μM) |
| --- | --- | --- | --- |
| compound 1 | 0.023 | compound 64 | 0.018 |
| compound 2 | 0.028 | compound 68 | 0.026 |
| compound 4 | 0.014 | compound 69 | 0.067 |
| compound 6 | 0.049 | compound 71 | 0.049 |
| compound 7 | 0.011 | compound 72 | 0.282 |
| compound 8 | 0.008 | compound 73 | 0.039 |
| compound 9 | 0.009 | compound 74 | 0.060 |
| compound 11 | 0.035 | compound 75 | 0.028 |
| compound 16 | 0.029 | compound 76 | 0.006 |
| compound 20 | 0.021 | compound 82 | 0.020 |
| compound 27 | 0.282 | compound 83 | 0.068 |
| compound 56 | 0.013 | Reference Compound | 0.024 |
| compound 62 | 0.054 | | |

From the Table 2, it can be seen that most compounds in the table have better inhibitory effect on Hepatoma cell Hep3B highly expressed FGFR4 and FGF19 than the reference compound, such as compound 1, compound 20, compound 4, compound 7, compound 8, compound 9, compound 20, compound 56, compound 64, compound 76 and compound 82.

Example C: PK Analysis of Rats

In the present invention, the pharmacokinetics experiment of the compounds in rats was performed using the SD rats (Vitolihua).

(1) Mode of administration: single gavage administration and intravenous injection administration.

(2) Dosage: 10 mg/kg in the gavage administration, 3 mg/kg in the intravenous injection administration.

(3) Sampling time point:

Gavage administration: before administration, 15 min, 30 min, 1 h, 2 h, 4 h, 6 h, 8 h, 24 h;

Intravenous injection administration: before administration, 5 min, 15 min, 30 min, 1 h, 2 h, 4 h, 6 h, 8 h, 24 h;

(4) Sample processing: 200 μL of orbital blood was collected at each sampling time point. After anticoagulation with heparin, the blood was centrifuged at 5500 rpm for 10 min, and 60 μL of the supernatant was taken and put into the refrigerator at −80° C. for waiting for testing.

Samples obtained after administration of Compound 1 were tested using 4000 LC-MS/MS analyzer, wherein, the chromatographic separation conditions for testing were:

Chromatographic column: Xselect HSS T3 2.5 μm (2.1× 50 mm) (Compound 1);

The mobile phase A: 5% acetonitrile and 95% water (0.1% FA (formic acid));

The mobile phase B: 95% acetonitrile and 5% water (0.1% FA);

Flow rate: 0.6 ml/min;
Eluted time: 4.00 min;
Injection volume: 5 μL;
The elution gradient was shown in the Table 3:

TABLE 3

| Time | The mobile phase A (%) | The mobile phase B (%) |
|---|---|---|
| 0.00 | 95.0 | 5.00 |
| 0.20 | 95.0 | 5.00 |
| 1.00 | 0.00 | 100 |
| 2.20 | 0.00 | 100 |
| 2.21 | 95.0 | 5.00 |
| 4.00 | 95.0 | 5.00 |

Samples obtained after administration of Compound 7 were tested using 4000 LC-MS/MS analyzer, wherein, the chromatographic separation conditions for testing were:
Chromatographic column: Agilent ZORBAX 3.5 μm SB $C_{18}$ (2.1×50 mm) (Compound 7);
The mobile phase A: 5% acetonitrile and 95% water (0.1% FA);
The mobile phase B: 95% acetonitrile and 5% water (0.1% FA);
Flow rate: 0.6 ml/min;
Eluted time: 3.80 mins;
Injection volume: 3 μL;
The elution gradient was shown in the Table 4:

TABLE 4

| Time | The mobile phase A (%) | The mobile phase B (%) |
|---|---|---|
| 0.00 | 95.0 | 5.00 |
| 0.15 | 95.0 | 5.00 |
| 1.50 | 0.00 | 100 |
| 2.50 | 0.00 | 100 |
| 2.60 | 95.0 | 5.00 |
| 3.80 | 95.0 | 5.00 |

Samples obtained after administration of Compound 16 were tested using 4000 LC-MS/MS analyzer, wherein, the chromatographic separation conditions for testing were:
Chromatographic column: Agilent ZORBAX 3.5 μm SB $C_{18}$ (2.1×50 mm) (Compound 16);
The mobile phase A: 5% acetonitrile and 95% water (0.1% FA);
The mobile phase B: 95% acetonitrile and 5% water (0.1% FA);
Flow rate: 0.6 ml/min;
Eluted time: 3.80 mins;
Injection volume: 10 μL;
The elution gradient was shown in the Table 5:

TABLE 5

| Time | The mobile phase A (%) | The mobile phase B (%) |
|---|---|---|
| 0.00 | 95.0 | 5.00 |
| 0.15 | 95.0 | 5.00 |
| 1.50 | 0.00 | 100 |
| 2.50 | 0.00 | 100 |
| 2.60 | 95.0 | 5.00 |
| 3.80 | 95.0 | 5.00 |

Samples obtained after administration of compound 4, compound 5, compound 20, compound 56, compound 71 or reference compound were tested using 5500 LC-MS/MS analyzer, wherein, the chromatographic separation conditions for the test were:
Chromatographic column: Xselect HSS T3 2.5 μm (2.1×50 mm) (the chromatographic column using for compound 4, compound 5, compound 20, compound 56, compound 71); Phenomenex Kinetex 5 μm $C_{18}$ 100A (2.1×50 mm) (the chromatographic column using for reference compound);
The mobile phase A: 5% acetonitrile and 95% water (0.1% FA);
The mobile phase B: 95% acetonitrile and 5% water (0.1% FA);
Flow rate: 0.6 ml/min;
Eluted time: 3.00 mins;
Injection volume: 2 μL;
The elution gradient was shown in the Table 6:

TABLE 6

| Time | The mobile phase A (%) | The mobile phase B (%) |
|---|---|---|
| 0.00 | 95.0 | 5.00 |
| 0.30 | 95.0 | 5.00 |
| 1.80 | 5.00 | 95.0 |
| 2.50 | 5.00 | 95.0 |
| 2.51 | 95.0 | 5.00 |
| 3.00 | 95.0 | 5.00 |

Mass spectrometry analysis conditions of compound:
The setting conditions of 4000 LC-MS/MS mass spectrometer in mass analysis were shown in Table 7 below:

TABLE 7

| Compound | Q1 | Q3 | DP | EP | CE | CXP |
|---|---|---|---|---|---|---|
| Compound 1 | 523.252 | 175.100 | 96 | 10 | 35 | 16 |
| Compound 7 | 508.287 | 175.100 | 96 | 10 | 35 | 16 |
| Compound 16 | 538.278 | 175.000 | 111 | 10 | 37 | 12 |
| Verapamil | 455.216 | 165.100 | 91 | 10 | 37 | 12 |

The setting conditions of 5500 LC-MS/MS mass spectrometer in mass analysis were shown in Table 8 and Table 9 below:

TABLE 8

| Compound | Q1 | Q3 | DP | EP | CE | CXP |
|---|---|---|---|---|---|---|
| Compound 4 | 537.083 | 175.100 | 76 | 10 | 37 | 14 |
| Compound 5 | 535.095 | 174.900 | 71 | 10 | 39 | 12 |
| Compound 20 | 549.071 | 175.100 | 71 | 10 | 37 | 12 |
| Compound 56 | 546.026 | 175.100 | 36 | 10 | 35 | 12 |
| Compound 71 | 537.078 | 175.000 | 146 | 10 | 37 | 14 |
| Verapamil | 455.216 | 165.100 | 91 | 10 | 37 | 12 |

TABLE 9

| Compound | Q1 | Q3 | DP | EP | CE | CXP |
|---|---|---|---|---|---|---|
| Reference compound | 507.252 | 175.100 | 56 | 10 | 25 | 14 |
| Dexamethasone | 393.171 | 373.000 | 96 | 10 | 13 | 10 |

Note: Q1, Q3, DP, EP, CE and CXP in the table respectively refer that Q1: parent ion; Q3: product ion; DP: declustering voltage; EP: inlet voltage; CE: collision energy; CXP: collision cell outlet voltage.

The results measured according to the above experimental steps were shown in Table 10 below:

Table 10

| Compound | p.o. (10 mg/kg) | |
|---|---|---|
| | Drug concentration in blood $C_{max}$ (ng/mL) | Curve area $AUC_{0-24\,h}$ (h × ng/mL) |
| Compound 1 | 833 | 2369 |
| Compound 4 | 1450 | 4671 |
| Compound 5 | 1400 | 6727 |
| Compound 7 | 736 | 2846 |
| Compound 16 | 936 | 3666 |
| Compound 20 | 514 | 1996 |
| Compound 56 | 548 | 2014 |
| Compound 71 | 657 | 1947 |
| Reference Compound | 350 | 1590 |

In Table 10, p.o. refers to oral administration.

From Table 10, it can be seen that, all of the compounds in the table showed better metabolic properties compared with the reference compound. The exposure amount $AUC_{0-24\,h}$ and the maximum drug concentration in blood $C_{max}$ were significantly higher than the reference compound, such as compound 1, compound 4, compound 5, compound 7, compound 16, compound 20, compound 56, and compound 71.

Example D: PK/PD of NOD-SCID Mouse

This experiment conducted when the pharmacological experiment in vivo was performed by gavage administration, wherein, the blood samples and tumor samples were taken at different time points to detect drug concentration in blood and drug concentrations in tumors.

(1) Mode of administration: gavage administration;
(2) Dosage: 50 mg/kg in the gavage administration;
(3) Sampling time point:

Sampling time point of blood samples: the sampling point of compound 4 and reference compound were before administration, at 1 h, 2 h, 4 h, 6 h. Three mice were sampled at each sampling point;

Sampling time point of tumor samples: the sampling point of compound 4 and reference compound were at 4 h, 6 h. Three mice were sampled at each sampling point;

(4) Blood sample collection: 200 μL of orbital blood was collected at sampling time point for each blood sample. After anticoagulation with heparin, the blood was centrifuged at 5500 rpm for 10 mins. 60 μL of the supernatant was taken and put it into the refrigerator at −80° C. for waiting for testing.

Tumour sample collection: 200-300 mg of each tumor tissue was taken. The tumor weight was marked, quickly freezed in liquid nitrogen and placed into a refrigerator at −80° C. for waiting for testing.

PK Detection:

Tumour sample processing: pure water was added into the tumor sample according to a ratio of 1 mg:3 mL between the weight of the tumor sample and the volume of pure water and then it was homogenized. The homogenate was stored at −90° C. to −60° C. until the sample was analyzed. After 5 μL of acetonitrile/water (v/v=1:1) was added into 50 μL of tumor sample homogenate, 200 μL of acetonitrile (containing Dexamethasone 100 ng/ml as internal standard, or containing Verapamil 2 ng/ml as internal standard) was added. After protein precipitation, the resulting mixture was vortexed for 2 mins at 4° C. with 4600 g, and then centrifuged for 15 mins to obtain the supernatant. 100 μL of the supernatant was taken and added into 200 μL of deionized water. 5500 LC/MS/MS analyser was used for sample injection and analysis, after vortexing for homogeneity. The conditions for chromatographic separation and mass spectrometric analysis were as follows:

Chromatographic column: Xselect HSS T3 2.5 μm (2.1× 50 mm) (compound 4); Phenomenex Kinetex 5 μm $C_{18}$ 100A (2.1×50 mm) (reference compound);

The mobile phase A: 5% acetonitrile and 95% water (0.1% FA);

The mobile phase B: 95% acetonitrile and 5% water (0.1% FA);

Flow rate: 0.6 ml/min;

Eluted time: 3.00 mins;

Injection volume: 2 μL;

The elution gradient was shown in the Table 11:

TABLE 11

| Time | The mobile phase A (%) | The mobile phase B (%) |
|---|---|---|
| 0.00 | 95.0 | 5.00 |
| 0.30 | 95.0 | 5.00 |
| 1.80 | 5.00 | 95.0 |
| 2.50 | 5.00 | 95.0 |
| 2.51 | 95.0 | 5.00 |
| 3.00 | 95.0 | 5.00 |

The setting conditions of the mass spectrometer in the mass spectrometry analysis were shown in Table 12 and Table 13 below:

TABLE 12

| Compound | Q1 | Q3 | DP | EP | CE | CXP |
|---|---|---|---|---|---|---|
| Reference compound | 507.252 | 175.100 | 56 | 10 | 25 | 14 |
| Dexamethasone | 393.171 | 373.000 | 96 | 10 | 13 | 10 |

TABLE 13

| Compound | Q1 | Q3 | DP | EP | CE | CXP |
|---|---|---|---|---|---|---|
| Compound 4 | 537.083 | 175.100 | 76 | 10 | 37 | 14 |
| Verapamil | 455.216 | 165.100 | 91 | 10 | 37 | 12 |

Note: Q1, Q3, DP, EP, CE and CXP in the table respectively refer that Q1: parent ion; Q3: product ion; DP: declustering voltage; EP: inlet voltage; CE: collision energy; CXP: collision cell outlet voltage.

The results measured according to the above experimental steps were shown in Table 14 below:

TABLE 14

| Compound | Model | p.o. (50 mg/kg) | | | | | Drug concentration in tumor(ng/g) | |
|---|---|---|---|---|---|---|---|---|
| | | $T_{1/2}$ (h) | $T_{max}$ (h) | $C_{max}$ (ng/ml) | $AUC_{0-6\,h}$ (h × ng/ml) | $AUC_{Inf}$ (h × ng/ml) | 4 h | 6 h |
| Reference compound | Hep3B | 3.13 | 1 | 6203 | 20193 | 29081 | 64.4 | 44.1 |
| | SNU878 | NA | 4 | 5430 | 20356 | NA | 3560 | 1030 |
| Compound 4 | Hep3B | 1.48 | 2 | 1021 | 3025 | 3358 | 1212 | 673 |
| | SNU878 | 2.3 | 1 | 1233 | 3531 | 4265 | 2336 | 1951 |

In Table 14, p.o. refers to oral administration.

From Table 14, it can be seen: the content of compound 4 at 6 h in tumor tissue was about twice than the reference compound in the SNU878 model in vivo, and the content of compound 4 at 4 h or 6 h in tumor tissue was more than 15 times than the reference compound in the Hep3B model in vivo. The above result indicated that compound 4 has better tumor-targeting property.

Example E: Pharmacodynamic In Vivo 5.1 Reagents and Materials

The Hep3B cell line was purchased from ATCC; MEM cell culture medium, fetal bovine serum, and trypsin were purchased from Gibco; cell culture flasks were purchased from Greiner; and disposable Cell Counting Plate and taittinger Blue Solution Purchased from Bio-Rad. The disposable sterile syringe was purchased from Changzhou Jinlong Medical Plastic Instrument Co., Ltd, eye surgical scissors and eye surgical forceps were purchased from Shanghai Medical Instrument (Group) Co., Ltd. Surgical Instrument Factory, and 6-8 week old female NOD-SCID mice were purchased from Vitalivar.

5.2 Cell Culture and Preparation of Cell Suspension a. One strain of Hep3B cells was taken out from the cell bank and MEM medium (MEM+10% FBS+1% PS) was used to recover the cells. The resuscitated cells were placed in a cell culture flask (the wall the flask was marked with the cell type, date, cultivator's name), and the cell culture flask was placed in a $CO_2$ incubator (the temperature of the incubator was 37° C. and the $CO_2$ concentration of the incubator was 5%);

b. When the cells covered about 90% of the bottom of the culture flask, passage was conducted. the cells were continued to cultivate in a $CO_2$ incubator after passage. The above process was repeated until the number of the cell satisfied the requirements of pharmacodynamic in vivo;

c. The cultured cells were collected and counted using a BIO-Rad TC20 cell counter. According to the counting results, the cultured cells were resuspended with PBS and matrix gel (1:1) to obtain a cell suspension (density $5\times10^7$/ml), and the cell suspension was placed in an ice box for later use.

5.3 Cell Inoculation and Tumor Measurement a. The cells were mixed well before seeding, and 0.5 ml of cell suspension was taken with a 1 ml syringe and bubbles in the cell suspension were removed. The syringe with the cell suspension was place on an ice pack for later use.

b. The NOD-SCID mice were set with the left hand, and the skin on the right back of the mice was disinfected with 75% alcohol. The inoculation was beginning after 30 seconds.

c. During inoculation, 1 mL syringe was on the right hand, and the cell suspension of Hep3B was inoculated subcutaneously into the right shoulder of the right back of the mouse at 0.1 mL/mouse. At inoculation interval, the syringe was placed on an ice pack and the mice were inoculated sequentially.

d. According to the tumor growth, the tumor was measured and the tumor size was calculated on the 12-15 days after inoculation.

Tumor volume calculation: tumor volume ($mm^3$)=length (mm)×width (mm)×width (mm)/2 e. When the tumors grew to an average volume of 100-150 $mm^3$, the mice were randomly divided into two groups according to tumor size and the weight of the mouse. There were 9 mice in either group, and one was the control group and the other was the treatment group.

f. The method of administration was gavage, and the control group was administered with 10% DMSO+90% dd$H_2O$ and the treatment group was respectively administered with the compound 4 at a dosage of 15/30/60 mg/kg once a day, the compound 4 at a dosage of 15 mg/kg twice a day, and the reference compound at a dosage of 60 mg/kg once a day. The solvent of the compound 4 was 10% DMSO+90% dd$H_2O$, and the solvent of the reference compound was 100% dd$H_2O$. Tumors were measured and the mice were weighed twice a week after administration.

g. The experiment was finished until the tumor volume of the control group was about 1500 $mm^3$.

The results of the compound's inhibition of tumors were shown in Table 15 below:

TABLE 15

| Groups | TGI % |
|---|---|
| Compound 4 15 mg/kg BID | 96.7 |
| Reference Compound 60 mg/kg QD | 97.7 |

Note: TGI (Tumor growth inhibition) %=(1−Tumor weight of treatment group/Tumor weight of control group)× 100%.

QD: once a day, BID: Twice a day.

From Table 15, it can be seen that the compound 4 of the present invention has an excellent antitumor effect, and the effect of 15 mg/kg BID of the compound 4 is equivalent to the effect of 60 mg/kg QD of the reference compound in the Hep3B model. The compound 4 achieved the same efficacy compared with the reference compound although the dose of the compound 4 was reduced by half, Therefore, the toxic side effects is fewer and the safety is higher.

What is claimed is:

1. A compound or a pharmaceutically acceptable salt thereof, wherein the compound is (R)—N-(5-cyano-4-((1-(methylthio) propan-2-yl)amino)pyridin-2-yl)-7-formyl-6-

((4-methyl-2-oxopiperazin-1-yl)methyl)-3,4-dihydro-1,8-naphthyridine-1(2H)-carboxamide.

2. A pharmaceutical composition comprising the compound or the pharmaceutically acceptable salt thereof according to claim 1, and at least one pharmaceutically acceptable excipient.

\* \* \* \* \*